US009718881B2

(12) United States Patent
Gromada et al.

(10) Patent No.: US 9,718,881 B2
(45) Date of Patent: Aug. 1, 2017

(54) ANTI-ACTIVIN A ANTIBODIES AND USES THEREOF

(71) Applicant: Regeneron Pharmaceuticals, Inc., Tarrytown, NY (US)

(72) Inventors: Jesper Gromada, Scarsdale, NY (US); Esther Latres, New York, NY (US); Andrew Murphy, Croton-on-Hudson, NY (US); George Yancopoulos, Yorktown Heights, NY (US); Lori Morton, Chappaqua, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 14/447,444

(22) Filed: Jul. 30, 2014

(65) Prior Publication Data
US 2015/0037339 A1  Feb. 5, 2015

Related U.S. Application Data

(60) Provisional application No. 61/859,926, filed on Jul. 30, 2013, provisional application No. 61/864,036, filed on Aug. 9, 2013, provisional application No. 61/911,834, filed on Dec. 4, 2013, provisional application No. 61/913,885, filed on Dec. 9, 2013.

(51) Int. Cl.
*A61K 39/395* (2006.01)
*C07K 16/22* (2006.01)
*A61K 39/00* (2006.01)

(52) U.S. Cl.
CPC ............ *C07K 16/22* (2013.01); *A61K 39/395* (2013.01); *A61K 39/3955* (2013.01); *A61K 2039/505* (2013.01); *A61K 2039/507* (2013.01); *C07K 2316/96* (2013.01); *C07K 2317/31* (2013.01); *C07K 2317/33* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,500,362 A | 3/1996 | Robinson et al. | |
| 5,821,337 A | 10/1998 | Carter et al. | |
| 6,096,506 A | 8/2000 | Lee et al. | |
| 6,368,597 B1 | 4/2002 | Strassmann et al. | |
| 6,468,535 B1 | 10/2002 | Lee et al. | |
| 6,858,208 B2 | 2/2005 | Lee et al. | |
| 7,070,784 B1 | 7/2006 | Halkier et al. | |
| 7,241,444 B2 | 7/2007 | Goetsch et al. | |
| 7,261,893 B2 | 8/2007 | Veldman et al. | |
| 7,320,789 B2 | 1/2008 | Aghajanian et al. | |
| 7,534,432 B2 | 5/2009 | Lee et al. | |
| 7,632,499 B2 | 12/2009 | Davies et al. | |
| 7,635,760 B2 | 12/2009 | Han et al. | |
| 7,655,763 B2 | 2/2010 | Veldman et al. | |
| 7,731,961 B1 | 6/2010 | Aghajanian et al. | |
| 7,745,583 B2 | 6/2010 | Han et al. | |
| 7,785,587 B2 | 8/2010 | Whittemore et al. | |
| 7,807,159 B2 | 10/2010 | Chin et al. | |
| 7,807,631 B2 | 10/2010 | Knopf et al. | |
| 7,888,486 B2 | 2/2011 | Walsh et al. | |
| 7,892,561 B2 | 2/2011 | Junker et al. | |
| 7,910,107 B2 | 3/2011 | Walsh et al. | |
| 8,309,082 B2 | 11/2012 | Han et al. | |
| 8,586,713 B2 | 11/2013 | Davis et al. | |
| 8,840,894 B2 | 9/2014 | Stitt et al. | |
| 8,871,209 B2 | 10/2014 | Stitt et al. | |
| 9,260,515 B2 | 2/2016 | Stitt et al. | |
| 2004/0142382 A1 | 7/2004 | Veldman et al. | |
| 2005/0175612 A1 | 8/2005 | Lee et al. | |
| 2006/0034831 A1 | 2/2006 | Tobin | |
| 2007/0178095 A1 | 8/2007 | Smith et al. | |

(Continued)

FOREIGN PATENT DOCUMENTS

EP      2594280       5/2013
WO   2004/037861 A2   5/2004

(Continued)

OTHER PUBLICATIONS

Abbott et al. Current approaches to fine mapping of antigen-antibody interactions. Immunology. Aug. 2014;142(4):526-35.*
Boder et al. Directed evolution of antibody fragments with monovalent femtomolar antigen-binding affinity. Proc Natl Acad Sci U S A. Sep. 26, 2000;97(20):10701-5.*
Cook et al. Structural basis for a functional antagonist in the transforming growth factor beta superfamily. J Biol Chem. Dec. 2, 2005;280(48):40177-86. Epub Sep. 26, 2005.*
Lin et al. The structural basis of TGF-beta, bone morphogenetic protein, and activin ligand binding. Reproduction. Aug. 2006;132(2):179-90.*
Thompson et al. Structures of an ActRIIB:activin A complex reveal a novel binding mode for TGF-beta ligand:receptor interactions. EMBO J. Apr. 1, 2003;22(7):1555-66.*
Xia et al. The biology of activin: recent advances in structure, regulation and function. J Endocrinol. Jul. 2009;202(1):1-12. Epub Mar. 9, 2009.*

(Continued)

Primary Examiner — David Romeo
(74) Attorney, Agent, or Firm — Merchant & Gould, P.C.

(57) ABSTRACT

The present invention provides antibodies that bind to Activin A and methods of using the same. According to certain embodiments of the invention, the antibodies are fully human antibodies that bind to Activin A with high affinity. The antibodies of the invention are useful for the treatment of diseases and disorders characterized by decreased muscle mass or strength, such as sarcopenia, cachexia, muscle injury, muscle wasting/atrophy, cancer, fibrosis, and weight loss. The antibodies of the invention are also useful in combination with GDF8 binding proteins for the treatment of diseases and disorders characterized by decreased muscle mass or strength. The antibodies of the invention are also useful for the prevention, treatment, or amelioration of disorders and diseases caused by, promoted by, exacerbated by, and/or aggravated by Activin A, such as renal fibrosis.

44 Claims, 4 Drawing Sheets

(56) References Cited

U.S. PATENT DOCUMENTS

| | | |
|---|---|---|
| 2007/0280945 A1 | 12/2007 | Stevens et al. |
| 2008/0187543 A1 | 8/2008 | Kambadur et al. |
| 2008/0299126 A1 | 12/2008 | Han et al. |
| 2009/0136481 A1 | 5/2009 | Kambadur et al. |
| 2009/0148436 A1 | 6/2009 | Lavallie et al. |
| 2009/0227497 A1 | 9/2009 | Sun et al. |
| 2009/0311252 A1 | 12/2009 | Knopf et al. |
| 2010/0080811 A1 | 4/2010 | Davies et al. |
| 2010/0166764 A1 | 7/2010 | Sayers et al. |
| 2010/0272734 A1 | 10/2010 | Berger et al. |
| 2010/0322942 A1 | 12/2010 | Whittemore et al. |
| 2011/0008375 A1 | 1/2011 | Hq et al. |
| 2011/0020330 A1 | 1/2011 | Aghajanian et al. |
| 2011/0256132 A1 | 10/2011 | Ashman et al. |
| 2011/0293630 A1 | 12/2011 | Stitt et al. |
| 2012/0015877 A1 | 1/2012 | Seehra et al. |
| 2012/0237521 A1 | 9/2012 | Berger et al. |
| 2013/0336982 A1 | 12/2013 | Mader et al. |
| 2015/0037339 A1 | 2/2015 | Gromada et al. |
| 2016/0304595 A1 | 10/2016 | Pordy et al. |
| 2016/0340421 A1 | 11/2016 | Stitt et al. |

FOREIGN PATENT DOCUMENTS

| | | |
|---|---|---|
| WO | 2005/094446 A2 | 10/2005 |
| WO | 2005/103081 A2 | 11/2005 |
| WO | 2006/116269 A2 | 11/2006 |
| WO | 2007/044411 A2 | 4/2007 |
| WO | 2007/047112 A2 | 4/2007 |
| WO | 2008/031061 A2 | 3/2008 |
| WO | 2009/058346 A1 | 5/2009 |
| WO | 2009/059943 A1 | 5/2009 |
| WO | 2010/070094 A1 | 6/2010 |
| WO | 2011/063018 | 5/2011 |
| WO | 2011/150008 A1 | 12/2011 |
| WO | 2012/064771 | 5/2012 |
| WO | 2013/074557 A1 | 5/2013 |

OTHER PUBLICATIONS

International Search Report mailed Jan. 8, 2015 for Corresponding PCT application PCT/US2014/048957.

Dufner et al., "Harnessing Phage and Ribosome Display for Antibody Optimization", Trends in Biotechnology, 24(11):523-529 (Nov. 1, 2006).

Canziani et al., "Characterization of Neutralizing Affinity-Matured Human Respiratory Syncytial Virus F Binding Antibodies in the Sub-Picomolar Affinity Range"; J of Molecular Recognition, 25(3):136-146 (Mar. 28, 2012).

Hanes et al., "Picomolar Affinity Antibodies from a Fully Synthetic Naïve Library Selected and Evolved by Ribosome Display"; Nature Biotechnology, 18(12):1287-1292 (Dec. 1, 2000).

Hoogenboom, "Selecting and Screening Recombinant Antibody Libraries", Nature Biotechnology, 23(9):1105-1116 (Sep. 1, 2005).

Orcutt et al., "Engineering an Antibody with Picomoloar Affinity to DOTA Chelates of Multiple Radionuclides for Pretargeted Radioimmunotherapy and Imaging", Nuclear Medicine and Biology, 38(2):223-233 (Aug. 31, 2010).

Rajpal et al., "A General Method for Greatly Improving the Affinity of Antibodies by Using Combinatorial Libraries", Proceedings of the National Academy of Sciences, 102(24):8466-8477 (Jun. 1, 2005).

Tornetta et al., "Antibody Fab Display and Selection Through Fusion to the pIX Coat pProtein of Filamentous Phage", J of Immunological Methods, 360(1-2):39-46 (Aug. 31, 2010).

Wark et al., "Latest Technologies for the Enhancement of Antibody Affinity", Science Direct, 58(5-6):547-670 (Aug. 7, 2006).

Al-Lazikani et al., "Standard Conformations for the Canonical Structures of Immunoglobulins"; J Mol Biol; 273(4):927-948 (1997).

Altschul et al., "Basic local alignment search tool"; J Mol Biol; 215(3):403-410 (1990).

Altschul et al., "Gapped BLAST and PSI-BLAST: a new generation of protein database search programs"; Nucleic Acids Res; 25(17):3389-33402 (1997).

Angal et al., "A single amino acid substitution abolishes the heterogeneity of chimeric mouse/human (IgG4) antibody"; Molecular Immunology; 30(1):105-108 (Jan. 1993).

Brown et al., "Tolerance of single, but Not Multiple, Amino Acid Replacements in Antibody $V_H$ CDR2: A Means of Minimizing B Cell Wastage from Somatic Hypermutation?"; The J of Immunology; 156(9):3285-3291 (May 1, 1996).

Chilean Substantive Report issued on Oct. 10, 2014, in corresponding Chilean Patent Application 3283-2012.

Clynes et al., "Fc receptors are required in passive and active immunity to melanoma"; Immunology, Proc. Nat'l. Acad. Sci. USA; 95:652-656 (Jan. 1998).

Cochrane et al., "Renal Structural and Functional Repair in a Mouse Model of Reversal of Ureteral Obstruction"; J Am Soc Nephrol; 16(12):3623-3630 (Dec. 1, 2005).

Colombian Office Action mailed Aug. 19, 2014 for related Colombian patent application 12233131.

Davies et al., "Affinity improvement of single antibody VH domains: residues in all three hypervariable regions affect antigen binding" Immunotechnology; 2(3):169-179 (Sep. 1996).

Ehring, "Hydrogen Exchange/electrospray Ionizatino Mass Spectrometry Sudies of Structural Features of Proteins and Protein/Protein Interactions"; Analytical Biochemistry; 267(2):252-259 (Feb. 15, 1999).

Engen et al., "Investigating protein structure and dynamics by hydrogen exchange MS"; Anal. Chem.; 73(9):256A-265A (May 1, 2001).

Giusti et al., "Somatic diversification of S107 from an antiphosphocholine to an anti-DNA autoantibody is due to a single base change in its heavy chain variable region"; PNAS, USA; 84(9):2926-2930 (May 1987).

Gonnet et al., "Exhaustive Matching of the Entire Protein Sequence Database"; Science; 256(5062):1443-1445 (Jun. 5, 1992).

Goodson, "Dental applications"; Medical Applications of Controlled Release; 2:115-138 (1984).

He et al., "Activin A inhibits formation of skeletal muscle during chick development"; Anat. Embryol (Berl); 209(5):401-407 (Jun. 2005).

Holt et al., "Domain antibodies: proteins for therapy"; Trends in Biotechnology; 21(11):484-490 (Nov. 2003).

International Search Report mailed Sep. 21, 2011, in corresponding PCT/US2011/037837.

International Search Report mailed May 23, 2013, in corresponding PCT/US2012/064911.

Junghans et al., "Anti-Tac-H, a Humanized Antibody to the Interleukin 2 Receptor with New Features for Immunotherapy in Malignant and Immune Disorders"; Cancer Res.; 50:1495-1502 (Mar. 1, 1990).

Kabat, "Sequences of Proteins of Immunological Interest"; National Institutes of Health (U.S.); 6 pages (1991).

Kazane et al., "Self-Assembled Antibody Multimers through Peptide Nucleic Acid Conjugation"; J Am Chem Soc.; 135(1):340-346 (Jan. 9, 2013).

Khurana et al., "Pharmacological Strategies for Muscular Dystrophy"; Nature Reviews/Druq Discovery; 2.379-390 (2003).

Klein et al., "Progress in overcoming the chain association issue in bispecific heterodimeric IgG antibodies"; mAbs; 4(6):653-663 (Nov./Dec. 2012).

Kufer et al.; "A revival of bispecific antibodies"; Trends Biotechnol; 22(5):238-244 (May 2004).

Kussie et al., "A Single Engineered Amino Acid Substitution Changes Antibody Fine Specificity"; J of Immunology; 152:146-152 (1994).

Langer, "New Methods of Drug Delivery"; Science; 249:1527-1533 (Sep. 23, 1990).

Lee et al., "Regulation of muscle growth by multiple ligands signaling through Activin type II receptors"; PNAS USA; 102(50):18117-18122 (Dec. 13, 2005) (Epub Dec. 5, 2005).

(56) References Cited

OTHER PUBLICATIONS

Lee et al., "Regulation of GDF-11 and myostatin activity by GASP-1 and GASP-2"; PNAS USA.; 110(3):E3713-E3722 (Sep. 9, 2013).
Liu et al., "Fine mapping of the antigen-antibody interaction of scFv215, a recombinant antibody inhibiting RNA polymerase II from *Drosophila melanogaster*"; J of Molecular Recognition; 12(2):103-111 (1999).
MacCallum et al., "Antibody-Antigen Interactions: Contact Analysis and Binding Site Topography"; J. Mol. Biol.; 262(5):732-745 (Oct. 11, 1996).
Martin et al., "Modeling antibody hypervariable loops: A combined algorithm"; PNAS USA; 86(23):9268-9272 (Dec. 1, 1989).
Maynard et al., "Antibody Engineering"; Annu. Rev. Biomed. Eng.; 02:339-376 (2000).
McPherron et al., "Regulation of skeletal muscle mass in mice by a new TGF-p superfamily member"; Nature; 387(6628):83-90 (May 1, 1997).
McPherron et al., "Redundancy of myostatin and growth/differentiation factor 11 function"; BMC Dev Biol; 9:24 (9 pgs) (Mar. 19, 2009).
Mordenti et al., "Interspecies Scaling of Clearance and Volume of Distribution Data for Five Therapeutic Proteins"; Pharm Res; 8(11):1351-1359 (Nov. 1991).
Munoz et al., "Biologicals Targeting Myostatin/GDF-11/Activins Prevent Burn-Induced Muscle Loss in Mice"; Journal of Surgical Research; 186(2) (abstract 34.6):591-592 (Feb. 2014).
Pearson, "Using the FASTA program to search protein and DNA sequence databases"; Methods Mol Biol,; 24(Ch 26): 307-331 (1994).
Pearson, "Flexible sequence similarity searching with the FASTA3 program package"; Methods Mol Biol; 132: 185-219 (2000).
Pini et al., "Design and Use of a Phage Display Library: Human Antibodies with Subnanomolar Affinity Against a Marker of Angiogenesis Eluted from a Two-Dimentional Gel"; J Biol Chem; 273(34): 21769-21776 (Aug. 21, 1998).
Powell et al., "Compendium of Excipients for Parenteral Formulations"; J of Pharm Science & Technology; 52(5):238-311 (Sep.-Oct. 1998).
Rajpal et al., "A general method for greatly improving the affinity of antibodies by using combinatorial libraries"; PNAS US; 102(24)8466-8471 (Jun. 1, 2005).
Reddy et al., "Elimination of Fc Receptor-Dependent Effector Functions of a Modified IgG4 Monoclonal Antibody to Human CD4"; J Immunol; 164:1925-1933 (2000).
Reineke, "Antibody epitope mapping using arrays of synthetic peptides"; Methods Mol Biol; 248(26):443-463 (2004).
Rudikoff et al., "Single amino acid substitution altering antigen-binding specificity"; PNAS, USA; 79:1979-1983 (Mar. 1982).
Schildbach, et al., "Heavy Chain Position 50 is a Determinant of Affinity and Specificity for the Anti-digoxin Antibody 26-10"; J Biol Chem; 268(29):21739-21747 (Oct. 15, 1993).
Schildbach et al., "Contribution of a single heavy chain residue to specificity of an anti-digoxin monoclonal antibody"; Protein Science; 3(5):737-749 (1994).
Sefton, "Implantable Pumps"; CRC Crit. Ref. Biomed. Eng.; 14:201-240 (1987).
Shield et al., "Lack of fucose on human IgG1 N-linked oligosaccharide improves binding to human Fcgamma RIII and antibody-dependent cellular toxicity"; J Biol Chem; 277(30):26733-26740 (Jul. 26, 2002).

Souza et al., "Proteomic identification and functional validation of activins and bone morphogenetic protein 11 as candidate novel muscle mass regulators"; Mol Endocrinol; 22(12):2689-2702 (Dec. 22, 2008).
Sozzani et al., "The yin and yang of Activin A"; Blood; 117(19):5013-5015 (May 12, 2011).
Sutcliffe et al., "Antibodies that React with Predetermined Sites on Proteins"; Science; 219:660-666(Feb. 11, 1983).
Taylor et al., "A Transgenic Mouse that Expresses a Diversity of Human Sequence Heavy and Light Chain Immunoglobulins"; Nucleic Acids Research; 20(23):6287-6295 (1992).
Tomer, Hochleitner et al., "Characterization of a discontinuous epitope of the human immunodeficiency virus (HIV) core protein p24 by epitope excision and differential chemical modification followed by mass spectrometric peptide mapping analysis"; Protein Science; 9:487-496 (2000).
Tsuchida et al., "Activin signaling as an emerging target for therapeutic interventions"; Cell Commun Signal; 7:15 (Jun. 18, 2009).
Tutt et al., "Trispecific F(ab')3 derivatives that use cooperative signaling via the TCR/CD3 complex and CD2 to activiate and redirect resting cytotoxic T cells"; J Immunol; 147(1):60-69 (1991).
Vajdos et al., "Comprehensive Functional Maps of the Antigen-Binding Site of an Anti-ErbB2 Antibody Obtained with Shotgun Scanning Mutagenesis"; J. Mol. Biol.; 320(2):415-428 (Jul. 2002).
Whittemore et al., "Inhibition of myostatin in adult mice increases skeletal muscle mass and strength"; Biochem, Biophys. Res. Commun; 300:965-971 (2003).
Wu et al., "Receptor-Mediated in Vitro Gene Transformation by a Soluble DNA Carrier System"; J Biol Chem; 262(10):4429-4432 (1987).
Wu et al., "Humanization of a Murine Monoclonal Antibody by Simultaneous Optimization of Framework and CDR Residues", J. Mol. Biol.; 294(1): 151-162 (Nov. 19, 1999).
Xiang et al., "Study of B72.3 combining sites by molecular modeling and site-directed mutagenesis"; Protein Eng.; 13(5):339-344 (May 2000).
International Search Report and Written Opinion mailed Jun. 30, 2016 in WO 2016/168613, 22 pages total.
Wagner et al., "A phase I/II trial of MYO-29 in adult subjects with muscular dystrophy," Annals of Neurology, vol. 63, No. 5, May 1, 2008, pp. 561-571.
LeBrasseur et al., "Myostatin inhibition enhances the effects of exercise on performance and metabolic outcomes in aged mice," Journals of Gerontology, Series A, Biological Sciences and Medical Sciences, vol. 64A, No. 9, Sep. 1, 2009, pp. 940-948.
Padhi et al., Pharmacological inhibition of myostatin and changes in lean body mass and lower extremity muscle size in patients receiving androgen deprivation therapy for prostate cancer, Journal of Clinical Endocrinology and Metabolism, vol. 99, No. 10, Oct. 1, 2014, pp. E1967-E1975.
Sharp et al., "The effects of a myostatin inhibitor on lean body mass, strength, and power in resistance trained males," Journal of the International Society of Sports Nutrition, vol. 11, No. Suppl 1, Dec. 1, 2014, p. P42.
Smith et al., "Myostatin inhibitors as therapies for muscle wasting associated with cancer and other disorders," Current Opinion in Supportive and Palliative Care, vol. 7, No. 4, Dec. 2013, p. 352-360.
Allen et al., "Expression and function of myostatin in obesity, diabetes, and exercise adaptation," Medicine and Science in Sports and Exercise, vol. 43, No. 10, Oct. 1, 2011, pp. 1828-1835.
Cadena et al., "Administration of a soluble activin type IIB receptor promotes muscle growth independent of fiber type," Journal of Applied Physiology, vol. 109, pp. 635-642 (2010).
Search Report and Written Opinion for Singapore patent application No. 11201600731W, dated Mar. 1, 2017, 12 pages total.

\* cited by examiner

Figure 1

SEQUENCE LISTING

<160> NUMBER OF SEQ ID NOS: 228

<210> SEQ ID NO 1
<211> LENGTH: 366
<212> TYPE: DNA
<213> ORGANISM: Artificial Sequence
<220> FEATURE:
<223> OTHER INFORMATION: Synthetic

<400> SEQUENCE: 1

```
caggtacagc tgcagcagtc aggtccagga ctgctgaagc cctcgcagac cctctcactc      60
acctgtgcca tctccgggga cagtgtctct agcaacagtg ctgcttggag ttggatcagg     120
cagtccccat cgagaggcct tgagtggctg gaaggacat attacaggc caactggttt       180
aatgattatg cactttctgt gaaaagtcga ataaccatca acccagtcac atccacgaac    240
cacttctccc tgcagctgca ctctgtgact cccgaggaca cggctgtgta ttactgtgca    300
agagaagggg ctctgggata ctactttgac tcctggggcc agggaaccct ggtcaccgtc    360
tcctca                                                                366
```

<210> SEQ ID NO 2
<211> LENGTH: 122
<212> TYPE: PRT
<213> ORGANISM: Artificial Sequence
<220> FEATURE:
<223> OTHER INFORMATION: Synthetic

<400> SEQUENCE: 2

Gln Val Gln Leu Gln Gln Ser Gly Pro Gly Leu Leu Lys Pro Ser Gln
 1               5                  10                  15

Thr Leu Ser Leu Thr Cys Ala Ile Ser Gly Asp Ser Val Ser Ser Asn
             20                  25                  30

Ser Ala Ala Trp Ser Trp Ile Arg Gln Ser Pro Ser Arg Gly Leu Glu
         35                  40                  45

Trp Leu Gly Arg Thr Tyr Tyr Arg Ala Asn Trp Phe Asn Asp Tyr Ala
     50                  55                  60

Leu Ser Val Lys Ser Arg Ile Thr Ile Asn Pro Val Thr Ser Thr Asn
 65                  70                  75                  80

His Phe Ser Leu Gln Leu His Ser Val Thr Pro Glu Asp Thr Ala Val
                 85                  90                  95

Tyr Tyr Cys Ala Arg Glu Gly Ala Leu Gly Tyr Tyr Phe Asp Ser Trp
            100                 105                 110

Gly Gln Gly Thr Leu Val Thr Val Ser Ser
        115                 120

<210> SEQ ID NO 3
<211> LENGTH: 30
<212> TYPE: DNA
<213> ORGANISM: Artificial Sequence
<220> FEATURE:
<223> OTHER INFORMATION: Synthetic

<400> SEQUENCE: 3

```
ggggacagtg tctctagcaa cagtgctgct                                       30
```

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Gly Asp Ser Val Ser Ser Asn Ser Ala Ala
1               5                   10

<210> SEQ ID NO 5
<211> LENGTH: 27
<212> TYPE: DNA
<213> ORGANISM: Artificial Sequence
<220> FEATURE:
<223> OTHER INFORMATION: Synthetic

<400> SEQUENCE: 5
acatattaca gggccaactg gtttaat                                          27

<210> SEQ ID NO 6
<211> LENGTH: 9
<212> TYPE: PRT
<213> ORGANISM: Artificial Sequence
<220> FEATURE:
<223> OTHER INFORMATION: Synthetic

<400> SEQUENCE: 6

Thr Tyr Tyr Arg Ala Asn Trp Phe Asn
1               5

<210> SEQ ID NO 7
<211> LENGTH: 36
<212> TYPE: DNA
<213> ORGANISM: Artificial Sequence
<220> FEATURE:
<223> OTHER INFORMATION: Synthetic

<400> SEQUENCE: 7
gcaagagaag gggctctggg atactacttt gactcc                                36

<210> SEQ ID NO 8
<211> LENGTH: 12
<212> TYPE: PRT
<213> ORGANISM: Artificial Sequence
<220> FEATURE:
<223> OTHER INFORMATION: Synthetic

<400> SEQUENCE: 8

Ala Arg Glu Gly Ala Leu Gly Tyr Tyr Phe Asp Ser
1               5                   10

<210> SEQ ID NO 9
<211> LENGTH: 339
<212> TYPE: DNA
<213> ORGANISM: Artificial Sequence
<220> FEATURE:
<223> OTHER INFORMATION: Synthetic

<400> SEQUENCE: 9
gacatcgtga tgacccagtc tccagactcc ctggctgtgt ctctgggcga gagggccacc      60
atcaactgca agtccagtca agtgttttta tacagctcca acaataagaa ttatttagct     120
tggtaccaac agaaaccagg gcagcctcct acactgctca tttactgggc atctacccgg     180
gaatccgggg tccctgaccg attcagtggc agcgggtctg ggacagattt cactctcacc     240
atcagcagcc tgcaggcgga agatgtggca atttattact gtcaccaata ttttattact     300
ccactcactt tcggcggagg gaccaaggtg gagatcaaa                            339

```
<210> SEQ ID NO 10
<211> LENGTH: 113
<212> TYPE: PRT
<213> ORGANISM: Artificial Sequence
<220> FEATURE:
<223> OTHER INFORMATION: Synthetic

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Thr Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Ile Tyr Tyr Cys His Gln
                85                  90                  95

Tyr Phe Ile Thr Pro Leu Thr Phe Gly Gly Gly Thr Lys Val Glu Ile
            100                 105                 110

Lys

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
caaagtgttt tatacagctc caacaataag aattat                              36

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gln Ser Val Leu Tyr Ser Ser Asn Asn Lys Asn Tyr
1               5                   10

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 tgggcatct                                                            9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14
```

Trp Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caccaatatt ttattactcc actcact        27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

His Gln Tyr Phe Ile Thr Pro Leu Thr
1               5

<210> SEQ ID NO 17
<211> LENGTH: 378
<212> TYPE: DNA
<213> ORGANISM: Artificial Sequence
<220> FEATURE:
<223> OTHER INFORMATION: Synthetic

<400> SEQUENCE: 17
caggtgcagc tggtggagtc tgggggaggc gtggtccagc ctggggaggtc cctgagactc        60 tcctgtgcag cgtctggatt caccttcagt agctatggca tgcactgggt ccgccaggct       120
ccaggcaagg ggctggagtg ggtggcagtt atatggtatg atggaagtaa taaatacaat       180
gcagactccg tgaagggccg attcaccatc tccagagaca attccaagaa cacggtgtat       240
ctgcaaatga acagcctgag agccgaggac acggctgtgt attactgtgc gagagcccgg       300
aattacgata ttttgactgg ttattataac ctcggtatgg acgtctgggg ccaagggacc       360
acggtcaccg tctcctca       378

<210> SEQ ID NO 18
<211> LENGTH: 126
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Asn Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Arg Ala Arg Asn Tyr Asp Ile Leu Thr Gly Tyr Tyr Asn Leu Gly
            100                 105                 110

Met Asp Val Trp Gly Gln Gly Thr Thr Val Thr Val Ser Ser
        115                 120                 125

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcacct tcagtagcta tggc                                      24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Ser Ser Tyr Gly
1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
atatggtatg atggaagtaa taaa                                      24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Trp Tyr Asp Gly Ser Asn Lys
1               5

<210> SEQ ID NO 23
<211> LENGTH: 57
<212> TYPE: DNA
<213> ORGANISM: Artificial Sequence
<220> FEATURE:
<223> OTHER INFORMATION: Synthetic

<400> SEQUENCE: 23
gcgagagccc ggaattacga tattttgact ggttattata acctcggtat ggacgtc    57

<210> SEQ ID NO 24
<211> LENGTH: 19
<212> TYPE: PRT
<213> ORGANISM: Artificial Sequence
<220> FEATURE:
<223> OTHER INFORMATION: Synthetic

<400> SEQUENCE: 24

Ala Arg Ala Arg Asn Tyr Asp Ile Leu Thr Gly Tyr Tyr Asn Leu Gly
1               5                   10                  15

Met Asp Val

<210> SEQ ID NO 25
<211> LENGTH: 321
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccatcctcc ctgtctgcat ctgtaggaga cagagtcacc     60
atcacttgcc gggcaagtca gggcattaga aatgatttag ctggtatcaa acagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtacac ttttggccag    300
gggaccaagc tggagatcaa a                                              321

<210> SEQ ID NO 26
<211> LENGTH: 107
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Tyr
                85                  90                  95

Thr Phe Gly Gln Gly Thr Lys Leu Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
cagggcatta gaaatgat                                                   18

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Gly Ile Arg Asn Asp
1               5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc                                                          9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
ctacagcata atagttaccc gtacact                                      27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Leu Gln His Asn Ser Tyr Pro Tyr Thr
1               5

<210> SEQ ID NO 33
<211> LENGTH: 375
<212> TYPE: DNA
<213> ORGANISM: Artificial Sequence
<220> FEATURE:
<223> OTHER INFORMATION: Synthetic

<400> SEQUENCE: 33
gaagtgcagc tggtggagtc tgggggaaac ttggtacagt ctggcaggtc cctgagactc     60
tcctgtacag cctctggatt cgcctttgat gattttgcca tgcactgggt ccggcaagtt    120
ccagggaagg gcctggagtg ggtctcaggt attagttgga atagtgatac catcggctat    180
gcggactctg tgaagggccg attcaccatt tccagagaca cgcccagaa ctccctgttt     240 ctgcaaatgg acagtctgag agctgaggac acggccttgt attactgtgt aaaagatatg    300
gttcggggac ttataggcta ctactactac ggtatggacg tctggggcca agggaccacg    360
gtcaccgtct cctca                                                    375

```
<210> SEQ ID NO 34
<211> LENGTH: 125
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Asn Leu Val Gln Ser Gly Arg
 1               5                  10                  15

Ser Leu Arg Leu Ser Cys Thr Ala Ser Gly Phe Ala Phe Asp Asp Phe
            20                  25                  30

Ala Met His Trp Val Arg Gln Val Pro Gly Lys Gly Leu Glu Trp Val
        35                  40                  45

Ser Gly Ile Ser Trp Asn Ser Asp Thr Ile Gly Tyr Ala Asp Ser Val
    50                  55                  60

Lys Gly Arg Phe Thr Ile Ser Arg Asp Asn Ala Gln Asn Ser Leu Phe
65                  70                  75                  80

Leu Gln Met Asp Ser Leu Arg Ala Glu Asp Thr Ala Leu Tyr Tyr Cys
                85                  90                  95

Val Lys Asp Met Val Arg Gly Leu Ile Gly Tyr Tyr Tyr Gly Met
            100                 105                 110

Asp Val Trp Gly Gln Gly Thr Thr Val Thr Val Ser Ser
        115                 120                 125

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35
ggattcgcct ttgatgattt tgcc                                          24

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Ala Phe Asp Asp Phe Ala
 1               5

<210> SEQ ID NO 37
<211> LENGTH: 24
<212> TYPE: DNA
<213> ORGANISM: Artificial Sequence
<220> FEATURE:
<223> OTHER INFORMATION: Synthetic

<400> SEQUENCE: 37
attagttgga atagtgatac catc                                          24

<210> SEQ ID NO 38
<211> LENGTH: 8
<212> TYPE: PRT
<213> ORGANISM: Artificial Sequence
<220> FEATURE:
<223> OTHER INFORMATION: Synthetic

<400> SEQUENCE: 38
```

Ile Ser Trp Asn Ser Asp Thr Ile
1               5

<210> SEQ ID NO 39
<211> LENGTH: 54
<212> TYPE: DNA
<213> ORGANISM: Artificial Sequence
<220> FEATURE:
<223> OTHER INFORMATION: Synthetic

<400> SEQUENCE: 39
gtaaaagata tggttcgggg acttataggc tactactact acggtatgga cgtc      54

<210> SEQ ID NO 40
<211> LENGTH: 18
<212> TYPE: PRT
<213> ORGANISM: Artificial Sequence
<220> FEATURE:
<223> OTHER INFORMATION: Synthetic

<400> SEQUENCE: 40

Val Lys Asp Met Val Arg Gly Leu Ile Gly Tyr Tyr Tyr Tyr Gly Met
1               5                   10                  15

Asp Val

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41
gaaatagtgt tgacgcagtc tccagccatc ctgtctttgt ctccagggga aagagccatc      60
ctctcctgca gggccagtca gagtatttac acctacttat cctggtacca acagacacct     120
ggccgggctc ccaggctcct catctatgag acatccagca gggccactgg catcccagcc     180
aggttcattg gcagtgggtc tgggacagac ttcactctca ccatcagtag cctagagcct     240
gaagattttg catttattac tgtcagcac cgtagcgact ggcctccac ttttggccag     300 gggaccaagc tggagatcaa a                                               321

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Glu Ile Val Leu Thr Gln Ser Pro Ala Ile Leu Ser Leu Ser Pro Gly
1               5                   10                  15

Glu Arg Ala Ile Leu Ser Cys Arg Ala Ser Gln Ser Ile Tyr Thr Tyr
            20                  25                  30

Leu Ser Trp Tyr Gln Gln Thr Pro Gly Arg Ala Pro Arg Leu Leu Ile
        35                  40                  45

Tyr Glu Thr Ser Ser Arg Ala Thr Gly Ile Pro Ala Arg Phe Ile Gly
    50                  55                  60

Ser Gly Ser Gly Thr Asp Phe Thr Leu Thr Ile Ser Ser Leu Glu Pro
65                  70                  75                  80

Glu Asp Phe Ala Phe Tyr Tyr Cys Gln His Arg Ser Asp Trp Pro Pro

```
                85                  90                  95

Thr Phe Gly Gln Gly Thr Lys Leu Glu Ile Lys
            100                 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
cagagtattt acacctac                                                  18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Ser Ile Tyr Thr Tyr
 1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gagacatcc                                                             9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Glu Thr Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
cagcaccgta gcgactggcc tcccact                                        27

<210> SEQ ID NO 48
<211> LENGTH: 9
<212> TYPE: PRT
<213> ORGANISM: Artificial Sequence
<220> FEATURE:
<223> OTHER INFORMATION: Synthetic

<400> SEQUENCE: 48

Gln His Arg Ser Asp Trp Pro Pro Thr
 1               5
```

<210> SEQ ID NO 49
<211> LENGTH: 351
<212> TYPE: DNA
<213> ORGANISM: Artificial Sequence
<220> FEATURE:
<223> OTHER INFORMATION: Synthetic

<400> SEQUENCE: 49

```
caggtgcagc tggtggagtc ggggggaggc gtggtccagc ctgggaggtc cctgagactc    60
tcctgtgtag cgtctggatt caccgtcagt agttatggca ttcactgggt ccgccaggct   120
ccaggcaagg gactggagtg ggtgtcagtt atatggtatg atggaagaaa taaagactat   180
gcagactccg tgaagggccg attcaccatc tccagagaca attccaagaa cacggtgtat   240
ttggaaatga aaggcctgag agccgaggac acggctcttt attattgtgc gagagacaaa   300
actggggatt ttgactcctg gggccaggga accctggtca ccgtctcctc a            351
```

<210> SEQ ID NO 50
<211> LENGTH: 117
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Val Glu Ser Gly Gly Gly Val Val Gln Pro Gly Arg
  1               5                  10                  15

Ser Leu Arg Leu Ser Cys Val Ala Ser Gly Phe Thr Val Ser Ser Tyr
             20                  25                  30

Gly Ile His Trp Val Arg Gln Ala Pro Gly Lys Gly Leu Glu Trp Val
         35                  40                  45

Ser Val Ile Trp Tyr Asp Gly Arg Asn Lys Asp Tyr Ala Asp Ser Val
     50                  55                  60

Lys Gly Arg Phe Thr Ile Ser Arg Asp Asn Ser Lys Asn Thr Val Tyr
 65                  70                  75                  80

Leu Glu Met Lys Gly Leu Arg Ala Glu Asp Thr Ala Leu Tyr Tyr Cys
                 85                  90                  95

Ala Arg Asp Lys Thr Gly Asp Phe Asp Ser Trp Gly Gln Gly Thr Leu
            100                 105                 110

Val Thr Val Ser Ser
        115
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggattcaccg tcagtagtta tggc                                            24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

```
<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
atatggtatg atggaagaaa taaa                                          24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54
```

Ile Trp Tyr Asp Gly Arg Asn Lys
 1               5

```
<210> SEQ ID NO 55
<211> LENGTH: 30
<212> TYPE: DNA
<213> ORGANISM: Artificial Sequence
<220> FEATURE:
<223> OTHER INFORMATION: Synthetic

<400> SEQUENCE: 55
gcgagagaca aaactgggga ttttgactcc                                    30

<210> SEQ ID NO 56
<211> LENGTH: 10
<212> TYPE: PRT
<213> ORGANISM: Artificial Sequence
<220> FEATURE:
<223> OTHER INFORMATION: Synthetic

<400> SEQUENCE: 56
```

Ala Arg Asp Lys Thr Gly Asp Phe Asp Ser
 1               5                  10

```
<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccatcctcc ctgtctgcat ctgtaggtga cagagtcacc    60
atcacttgcc gggcaagtca gaacattaac agcttttta gttggtatca gcagaaacca   120
ggaaaagccc ctaagttcct gatctatgat gcttccagta tacaaagtgg ggccccatcg   180
aggttcagtg gcagtggatc tgggacagat ttcactctca ccatcagtag tctgcaacct   240
gaagattttg caacttacta ctgtcaacag agttacagtt ccccgttcac ttttggccag   300
gggaccaagc tggagatcaa a                                             321

<210> SEQ ID NO 58
<211> LENGTH: 107
<212> TYPE: PRT
```

```
<213> ORGANISM: Artificial Sequence
<220> FEATURE:
<223> OTHER INFORMATION: Synthetic

<400> SEQUENCE: 58

Asp Ile Gln Met Thr Gln Ser Pro Ser Leu Ser Ala Ser Val Gly
1               5                   10                  15

Asp Arg Val Thr Ile Thr Cys Arg Ala Ser Gln Asn Ile Asn Ser Phe
            20                  25                  30

Leu Ser Trp Tyr Gln Gln Lys Pro Gly Lys Ala Pro Lys Phe Leu Ile
        35                  40                  45

Tyr Asp Ala Ser Ser Ile Gln Ser Gly Ala Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Ser Pro Phe
                85                  90                  95

Thr Phe Gly Gln Gly Thr Lys Leu Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59
cagaacatta acagcttt                                                   18

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

Gln Asn Ile Asn Ser Phe
1               5

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61 gatgcttcc                                                              9

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Asp Ala Ser
1

<210> SEQ ID NO 63
```

```
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagagtt acagttcccc gttcact                                              27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Ser Tyr Ser Ser Pro Phe Thr
 1               5

<210> SEQ ID NO 65
<211> LENGTH: 375
<212> TYPE: DNA
<213> ORGANISM: Artificial Sequence
<220> FEATURE:
<223> OTHER INFORMATION: Synthetic

<400> SEQUENCE: 65
gaagtgcagc tggtggagtc tgggggaggc ttggtacagc ctggcaggtc cctgagactc           60
tcctgtaaag cctctggatt cgcctttgat gatttcgcca tgcactgggt ccggcaagct          120
ccagggaagg gcctggagtg ggtctcaggt attgtttgga acagtggtga cataggctat          180
gcggactctg tgaagggccg attcaccatc tccagagaca acgccaagaa ctccctgtat          240
ctgcaactga atagtctgag aactgaggac acggccttgt atttctgtgt aaaagatatg          300
gttcggggac ttatgggctt caactattac ggtatggacg tctggggcca agggaccacg          360
gtcaccgtct cctca                                                          375

<210> SEQ ID NO 66
<211> LENGTH: 125
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Arg
 1               5                  10                  15

Ser Leu Arg Leu Ser Cys Lys Ala Ser Gly Phe Ala Phe Asp Asp Phe
            20                  25                  30

Ala Met His Trp Val Arg Gln Ala Pro Gly Lys Gly Leu Glu Trp Val
        35                  40                  45

Ser Gly Ile Val Trp Asn Ser Asp Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Thr Glu Asp Thr Ala Leu Tyr Phe Cys
                85                  90                  95

Val Lys Asp Met Val Arg Gly Leu Met Gly Phe Asn Tyr Tyr Gly Met
            100                 105                 110

Asp Val Trp Gly Gln Gly Thr Thr Val Thr Val Ser Ser
```

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggattcgcct ttgatgattt cgcc                                           24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Ala Phe Asp Asp Phe Ala
1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
attgtttgga acagtggtga cata                                           24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Val Trp Asn Ser Gly Asp Ile
1               5

<210> SEQ ID NO 71
<211> LENGTH: 54
<212> TYPE: DNA
<213> ORGANISM: Artificial Sequence
<220> FEATURE:
<223> OTHER INFORMATION: Synthetic

<400> SEQUENCE: 71
gtaaaagata tggttcgggg acttatgggc ttcaactatt acggtatgga cgtc          54

<210> SEQ ID NO 72
<211> LENGTH: 18
<212> TYPE: PRT
<213> ORGANISM: Artificial Sequence
<220> FEATURE:
<223> OTHER INFORMATION: Synthetic

<400> SEQUENCE: 72

Val Lys Asp Met Val Arg Gly Leu Met Gly Phe Asn Tyr Tyr Gly Met
1               5                   10                  15

Asp Val

<210> SEQ ID NO 73
<211> LENGTH: 321
<212> TYPE: DNA
<213> ORGANISM: Artificial Sequence
<220> FEATURE:
<223> OTHER INFORMATION: Synthetic

<400> SEQUENCE: 73

```
gaaattgtgt tgacgcagtc tccagccacc ctgtctttgt ctccagggga aagagccacc      60
ctctcctgca gggccagtca aactattagt acttatttag tctggtaccg acagagacct     120
ggccaggctc ccagtctcct catttatgat gcatccaaca gggccactga catcccagcc     180
aggttcagtg gcagtgggtc tgggacagac ttcactctca ccatcagcag ccttgagcct     240
gaagattttg cagtttatta ctgtcagcag cgtagcaact ggccgatcac cttcggccaa     300
gggacacgac tggagattaa a                                               321
```

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Thr Ile Ser Thr Tyr
            20                  25                  30

Leu Val Trp Tyr Arg Gln Arg Pro Gly Gln Ala Pro Ser Leu Leu Ile
        35                  40                  45

Tyr Asp Ala Ser Asn Arg Ala Thr Asp Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Ile
                85                  90                  95

Thr Phe Gly Gln Gly Thr Arg Leu Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75

```
caaactatta gtacttat                                                    18
```

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

Gln Thr Ile Ser Thr Tyr
1               5

```
<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gatgcatcc                                                                  9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Asp Ala Ser
 1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
cagcagcgta gcaactggcc gatcacc                                             27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Arg Ser Asn Trp Pro Ile Thr
 1               5

<210> SEQ ID NO 81
<211> LENGTH: 369
<212> TYPE: DNA
<213> ORGANISM: Artificial Sequence
<220> FEATURE:
<223> OTHER INFORMATION: Synthetic

<400> SEQUENCE: 81
gaagtgcagc tggtggagtc tgggggaggc ttggtacagc ctggcaggtc cctgacactc          60
tcctgtgcag tctctggatt caccttttgat gatcatgcca tgcactgggt ccggcaagct       120
ccagggaagg gcctggagtg ggtctcaggt attagttgga atagtgtaag tataggctat        180
gcggactctg tgaagggccg attcacgatc tccagagaca acgccaagac ctccctctat        240
ctgcaaatga acagtctgag agttgacgac acggcttat attactgtgt gcaagattta         300
aacgatattt tgactggtta tcccctcttt gacttttggg ccagggaac cctggtcacc         360 gtctcctca                                                                369

<210> SEQ ID NO 82
<211> LENGTH: 123
<212> TYPE: PRT
<213> ORGANISM: Artificial Sequence
<220> FEATURE:
```

<223> OTHER INFORMATION: Synthetic

<400> SEQUENCE: 82

Glu Val Gln Leu Val Glu Ser Gly Gly Gly Leu Val Gln Pro Gly Arg
1               5                   10                  15

Ser Leu Thr Leu Ser Cys Ala Val Ser Gly Phe Thr Phe Asp Asp His
            20                  25                  30

Ala Met His Trp Val Arg Gln Ala Pro Gly Lys Gly Leu Glu Trp Val
        35                  40                  45

Ser Gly Ile Ser Trp Asn Ser Val Ser Ile Gly Tyr Ala Asp Ser Val
    50                  55                  60

Lys Gly Arg Phe Thr Ile Ser Arg Asp Asn Ala Lys Ser Leu Tyr
65                  70                  75                  80

Leu Gln Met Asn Ser Leu Arg Val Asp Asp Thr Ala Leu Tyr Tyr Cys
                85                  90                  95

Val Gln Asp Leu Asn Asp Ile Leu Thr Gly Tyr Pro Leu Phe Asp Phe
            100                 105                 110

Trp Gly Gln Gly Thr Leu Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83
ggattcacct ttgatgatca tgcc                                          24

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Phe Thr Phe Asp Asp His Ala
1               5

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85
attagttgga atagtgtaag tata                                          24

<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Ile Ser Trp Asn Ser Val Ser Ile
1               5

<210> SEQ ID NO 87
<211> LENGTH: 48
<212> TYPE: DNA
<213> ORGANISM: Artificial Sequence
<220> FEATURE:
<223> OTHER INFORMATION: Synthetic

<400> SEQUENCE: 87
gtgcaagatt taaacgatat tttgactggt tatccctct ttgactttt                    48

<210> SEQ ID NO 88
<211> LENGTH: 16
<212> TYPE: PRT
<213> ORGANISM: Artificial Sequence
<220> FEATURE:
<223> OTHER INFORMATION: Synthetic

<400> SEQUENCE: 88

Val Gln Asp Leu Asn Asp Ile Leu Thr Gly Tyr Pro Leu Phe Asp Phe
 1               5                  10                  15

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccatcctcc ctgtctgcat ctgtaggaga cagagtcacc        60
atcacttgcc gggcaagtca gagcattagc agctatttaa attggtatca gcagaaacca      120
gggaaagccc ctaagctcct gatctatgct gcatccagtt tgcaaagtgg ggtcccgtca      180
aggttcagtg gcagtggatc tgggacagat ttcactctca ccatcagcag tctgcaacct      240
gaagattttg caacttacta ctgtcaacag agttacagta cccctccgat caccttcggc      300
caagggacac gactggagat taaa                                             324

<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105

<210> SEQ ID NO 91

<211> LENGTH: 18
<212> TYPE: DNA
<213> ORGANISM: Artificial Sequence
<220> FEATURE:
<223> OTHER INFORMATION: Synthetic

<400> SEQUENCE: 91
cagagcatta gcagctat                                                       18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Ser Ile Ser Ser Tyr
 1               5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc                                                                  9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
 1

<210> SEQ ID NO 95
<211> LENGTH: 30
<212> TYPE: DNA
<213> ORGANISM: Artificial Sequence
<220> FEATURE:
<223> OTHER INFORMATION: Synthetic

<400> SEQUENCE: 95
caacagagtt acagtacccc tccgatcacc                                          30

<210> SEQ ID NO 96
<211> LENGTH: 10
<212> TYPE: PRT
<213> ORGANISM: Artificial Sequence
<220> FEATURE:
<223> OTHER INFORMATION: Synthetic

<400> SEQUENCE: 96

Gln Gln Ser Tyr Ser Thr Pro Pro Ile Thr
 1               5                  10

<210> SEQ ID NO 97
<211> LENGTH: 369
<212> TYPE: DNA
<213> ORGANISM: Artificial Sequence
<220> FEATURE:

<223> OTHER INFORMATION: Synthetic

<400> SEQUENCE: 97

```
gaagtgcagc tggtggagtc tgggggaggc ttggtacagg ctggcaggtc cctaagactc      60
tcctgtgaag cctctggatt cacctttgat gattatggca tgcactgggt ccggcaaggt     120
ccagggaagg gcctggagtg ggtctcaggt attagttgga atagtggtaa catagactat     180
gcggactctg tgaagggccg attcaccatc tccagagaca acgccaagac ctccctgtat     240
ctgcaaatga acagtctgaa aactgacgac acggccttgt atttctgtgc aaaagatgct     300
gtggggttta actggaacta ctttctcttt gactactggg gccagggaac cctggtcacc     360
gtctcctca                                                             369
```

<210> SEQ ID NO 98
<211> LENGTH: 123
<212> TYPE: PRT
<213> ORGANISM: Artificial Sequence
<220> FEATURE:
<223> OTHER INFORMATION: Synthetic

<400> SEQUENCE: 98

```
Glu Val Gln Leu Val Glu Ser Gly Gly Gly Leu Val Gln Ala Gly Arg
 1               5                  10                  15

Ser Leu Arg Leu Ser Cys Glu Ala Ser Gly Phe Thr Phe Asp Asp Tyr
            20                  25                  30

Gly Met His Trp Val Arg Gln Gly Pro Gly Lys Gly Leu Glu Trp Val
        35                  40                  45

Ser Gly Ile Ser Trp Asn Ser Gly Asn Ile Asp Tyr Ala Asp Ser Val
    50                  55                  60

Lys Gly Arg Phe Thr Ile Ser Arg Asp Asn Ala Lys Thr Ser Leu Tyr
65                  70                  75                  80

Leu Gln Met Asn Ser Leu Lys Thr Asp Asp Thr Ala Leu Tyr Phe Cys
                85                  90                  95

Ala Lys Asp Ala Val Gly Phe Asn Trp Asn Tyr Phe Leu Phe Asp Tyr
            100                 105                 110

Trp Gly Gln Gly Thr Leu Val Thr Val Ser Ser
        115                 120
```

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggattcacct ttgatgatta tggc                                             24
```

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

```
Gly Phe Thr Phe Asp Asp Tyr Gly
 1               5
```

<210> SEQ ID NO 101

```
<211> LENGTH: 24
<212> TYPE: DNA
<213> ORGANISM: Artificial Sequence
<220> FEATURE:
<223> OTHER INFORMATION: Synthetic

<400> SEQUENCE: 101
attagttgga atagtggtaa cata                                          24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Trp Asn Ser Gly Asn Ile
 1               5

<210> SEQ ID NO 103
<211> LENGTH: 48
<212> TYPE: DNA
<213> ORGANISM: Artificial Sequence
<220> FEATURE:
<223> OTHER INFORMATION: Synthetic

<400> SEQUENCE: 103
gcaaaagatg ctgtggggtt aactggaac tactttctct ttgactac                 48

<210> SEQ ID NO 104
<211> LENGTH: 16
<212> TYPE: PRT
<213> ORGANISM: Artificial Sequence
<220> FEATURE:
<223> OTHER INFORMATION: Synthetic

<400> SEQUENCE: 104

Ala Lys Asp Ala Val Gly Phe Asn Trp Asn Tyr Phe Leu Phe Asp Tyr
 1               5                  10                  15

<210> SEQ ID NO 105
<211> LENGTH: 351
<212> TYPE: DNA
<213> ORGANISM: Artificial Sequence
<220> FEATURE:
<223> OTHER INFORMATION: Synthetic

<400> SEQUENCE: 105
caggtgcagc tggtggagtc tggggggaggc gtggtccagc ctggagggtc cctgagactc    60
acctgtgtag cgtctggatt caccgtcagt agtyatggaa tgcactgggt ccgccaggcc   120
ccaggcaagg ggctggagtg ggtggcagtt atgttttatg atgaaagtaa aaatattat   180 gcagactccg tgaagggccg attcaccatc tccagagaca attccaagaa cacgctgtat   240
ctgcaaatga acagcctgag agtcgaggac acggctgtgt attactgtgc gagagatgaa   300
cagctcgact ttgaatactg gggccaggga accctggtca ccgtctcctc a           351

<210> SEQ ID NO 106
<211> LENGTH: 117
<212> TYPE: PRT
<213> ORGANISM: Artificial Sequence
<220> FEATURE:
<223> OTHER INFORMATION: Synthetic

<400> SEQUENCE: 106
```

Gln Val Gln Leu Val Glu Ser Gly Gly Val Val Gln Pro Gly Arg
1               5                   10                  15

Ser Leu Arg Leu Thr Cys Val Ala Ser Gly Phe Thr Val Ser Ser Tyr
            20                  25                  30

Gly Met His Trp Val Arg Gln Ala Pro Gly Lys Gly Leu Glu Trp Val
        35                  40                  45

Ala Val Met Phe Tyr Asp Glu Ser Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Asp Glu Gln Leu Asp Phe Glu Tyr Trp Gly Gln Gly Thr Leu
            100                 105                 110

Val Thr Val Ser Ser
        115

<210> SEQ ID NO 107
<211> LENGTH: 24
<212> TYPE: DNA
<213> ORGANISM: Artificial Sequence
<220> FEATURE:
<223> OTHER INFORMATION: Synthetic

<400> SEQUENCE: 107
ggattcaccg tcagtagtta tgga                                    24

<210> SEQ ID NO 108
<211> LENGTH: 8
<212> TYPE: PRT
<213> ORGANISM: Artificial Sequence
<220> FEATURE:
<223> OTHER INFORMATION: Synthetic

<400> SEQUENCE: 108

Gly Phe Thr Val Ser Ser Tyr Gly
1               5

<210> SEQ ID NO 109
<211> LENGTH: 24
<212> TYPE: DNA
<213> ORGANISM: Artificial Sequence
<220> FEATURE:
<223> OTHER INFORMATION: Synthetic

<400> SEQUENCE: 109
atgttttatg atgaaagtaa aaaa                                    24

<210> SEQ ID NO 110
<211> LENGTH: 8
<212> TYPE: PRT
<213> ORGANISM: Artificial Sequence
<220> FEATURE:
<223> OTHER INFORMATION: Synthetic

<400> SEQUENCE: 110

Met Phe Tyr Asp Glu Ser Lys Lys
1               5

<210> SEQ ID NO 111
<211> LENGTH: 30
<212> TYPE: DNA

<210> SEQ ID NO 111  
<211> LENGTH: 30  
<212> TYPE: DNA  
<213> ORGANISM: Artificial Sequence
<220> FEATURE:
<223> OTHER INFORMATION: Synthetic

<400> SEQUENCE: 111
gcgagagatg aacagctcga ctttgaatac                                30

<210> SEQ ID NO 112
<211> LENGTH: 10
<212> TYPE: PRT
<213> ORGANISM: Artificial Sequence
<220> FEATURE:
<223> OTHER INFORMATION: Synthetic

<400> SEQUENCE: 112

Ala Arg Asp Glu Gln Leu Asp Phe Glu Tyr
 1               5                  10

<210> SEQ ID NO 113
<211> LENGTH: 369
<212> TYPE: DNA
<213> ORGANISM: Artificial Sequence
<220> FEATURE:
<223> OTHER INFORMATION: Synthetic

<400> SEQUENCE: 113
gaagtgcagc tggtggagtc tgggggaggc ttggtacagc ctggcaggtc cctgagactc      60
tcctgtgcag cctctggatt cacctttgat gattatgcca tgcactgggt ccggcaagct     120
ccagggaagg gcctggagtg ggtctcaggt attagttgga atagtggtag cataggctat     180
gcggactctg tgaagggccg attcaccatc tccagagaca cgccaagaa ctccctgtat      240 ctgcaaatga acagtctgag agctgaggac acggccttgt attactgtgc aaaagatata     300
atggggaact gggactactt ctacggtatg gacgtctggg gccaagggac cacggtcacc     360
gtctcctca                                                             369

<210> SEQ ID NO 114
<211> LENGTH: 123
<212> TYPE: PRT
<213> ORGANISM: Artificial Sequence
<220> FEATURE:
<223> OTHER INFORMATION: Synthetic

<400> SEQUENCE: 114

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Met Gly Asn Trp Asp Tyr Phe Tyr Gly Met Asp Val
            100                 105                 110

Trp Gly Gln Gly Thr Thr Val Thr Val Ser Ser
        115                 120

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggattcacct ttgatgatta tgcc                                               24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Phe Thr Phe Asp Asp Tyr Ala
1               5

<210> SEQ ID NO 117
<211> LENGTH: 24
<212> TYPE: DNA
<213> ORGANISM: Artificial Sequence
<220> FEATURE:
<223> OTHER INFORMATION: Synthetic

<400> SEQUENCE: 117
attagttgga atagtggtag cata                                               24

<210> SEQ ID NO 118
<211> LENGTH: 8
<212> TYPE: PRT
<213> ORGANISM: Artificial Sequence
<220> FEATURE:
<223> OTHER INFORMATION: Synthetic

<400> SEQUENCE: 118

Ile Ser Trp Asn Ser Gly Ser Ile
1               5

<210> SEQ ID NO 119
<211> LENGTH: 48
<212> TYPE: DNA
<213> ORGANISM: Artificial Sequence
<220> FEATURE:
<223> OTHER INFORMATION: Synthetic

<400> SEQUENCE: 119
gcaaaagata taatggggaa ctgggactac ttctacggta tggacgtc                    48

<210> SEQ ID NO 120
<211> LENGTH: 16
<212> TYPE: PRT
<213> ORGANISM: Artificial Sequence
<220> FEATURE:
<223> OTHER INFORMATION: Synthetic

<400> SEQUENCE: 120

Ala Lys Asp Ile Met Gly Asn Trp Asp Tyr Phe Tyr Gly Met Asp Val
1               5                   10                  15

<210> SEQ ID NO 121
<211> LENGTH: 369
<212> TYPE: DNA

```
<213> ORGANISM: Artificial Sequence
<220> FEATURE:
<223> OTHER INFORMATION: Synthetic

<400> SEQUENCE: 121
gaagtgcagc tggtggagtc tgggggaggc ttggtacagc ctggcaggtc cctgagactc      60
tcctgtgcag cctctggatt cacctttgat gataatgcca tgcactgggt ccggcaacct     120
ccagggaagg gcctggagtg ggtctcaggt attagttgga atagtggaag cataggctat     180
gcggactctg tgaagggccg attcaccatc tccagagaca acgccaagaa ctccctgtat     240
ctgcaaatga acagtctgag agctgaggac acggccttgt attactgtgc aaaagatata     300
aacgatattt tgactggtta tcctctttt gattactggg gccagggaac cctggtcacc     360
gtctcctca                                                             369

<210> SEQ ID NO 122
<211> LENGTH: 123
<212> TYPE: PRT
<213> ORGANISM: Artificial Sequence
<220> FEATURE:
<223> OTHER INFORMATION: Synthetic

<400> SEQUENCE: 122

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asp Asp Asn
            20                  25                  30

Ala Met His Trp Val Arg Gln Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Asp Ile Asn Asp Ile Leu Thr Gly Tyr Pro Leu Phe Asp Tyr
            100                 105                 110

Trp Gly Gln Gly Thr Leu Val Thr Val Ser Ser
        115                 120

<210> SEQ ID NO 123
<211> LENGTH: 24
<212> TYPE: DNA
<213> ORGANISM: Artificial Sequence
<220> FEATURE:
<223> OTHER INFORMATION: Synthetic

<400> SEQUENCE: 123
ggattcacct ttgatgataa tgcc                                              24

<210> SEQ ID NO 124
<211> LENGTH: 8
<212> TYPE: PRT
<213> ORGANISM: Artificial Sequence
<220> FEATURE:
<223> OTHER INFORMATION: Synthetic

<400> SEQUENCE: 124

Gly Phe Thr Phe Asp Asp Asn Ala
 1               5
```

<210> SEQ ID NO 125
<211> LENGTH: 24
<212> TYPE: DNA
<213> ORGANISM: Artificial Sequence
<220> FEATURE:
<223> OTHER INFORMATION: Synthetic

<400> SEQUENCE: 125
attagttgga atagtggaag cata                                         24

<210> SEQ ID NO 126
<211> LENGTH: 8
<212> TYPE: PRT
<213> ORGANISM: Artificial Sequence
<220> FEATURE:
<223> OTHER INFORMATION: Synthetic

<400> SEQUENCE: 126

Ile Ser Trp Asn Ser Gly Ser Ile
 1               5

<210> SEQ ID NO 127
<211> LENGTH: 48
<212> TYPE: DNA
<213> ORGANISM: Artificial Sequence
<220> FEATURE:
<223> OTHER INFORMATION: Synthetic

<400> SEQUENCE: 127
gcaaaagata taaacgatat tttgactggt tatcctcttt ttgattac              48

<210> SEQ ID NO 128
<211> LENGTH: 16
<212> TYPE: PRT
<213> ORGANISM: Artificial Sequence
<220> FEATURE:
<223> OTHER INFORMATION: Synthetic

<400> SEQUENCE: 128

Ala Lys Asp Ile Asn Asp Ile Leu Thr Gly Tyr Pro Leu Phe Asp Tyr
 1               5                  10                  15

<210> SEQ ID NO 129
<211> LENGTH: 378
<212> TYPE: DNA
<213> ORGANISM: Artificial Sequence
<220> FEATURE:
<223> OTHER INFORMATION: Synthetic

<400> SEQUENCE: 129
gaagtgcagc tggtggagtc tgggggaggc gtggtacagc ctggggggtc cctgagactc   60
tcctgtgcag cctctacatt caccttttgat gattttgcca tgcactgggt ccgtcaagct  120
ccagggaagg gtctggagtg ggtctctctt attactgggg atggtggtag cacatactat  180
gcagaccctg tgaagggccg attcaccatc tccagagaca cagcaaaaa ctccctgtat   240 ctgcaaatga acagtctgag aactgaggac accgccttgt attactgtgt aaaagattgg  300
tggatagcag ctcgtccgga ctactactac tacggtatgg acgtctgggg ccaagggacc  360
acggtcaccg tctcctca                                               378

<210> SEQ ID NO 130
<211> LENGTH: 126
<212> TYPE: PRT
<213> ORGANISM: Artificial Sequence

```
<220> FEATURE:
<223> OTHER INFORMATION: Synthetic

<400> SEQUENCE: 130

Glu Val Gln Leu Val Glu Ser Gly Gly Gly Val Val Gln Pro Gly Gly
 1               5                  10                  15

Ser Leu Arg Leu Ser Cys Ala Ala Ser Thr Phe Thr Phe Asp Asp Phe
            20                  25                  30

Ala Met His Trp Val Arg Gln Ala Pro Gly Lys Gly Leu Glu Trp Val
        35                  40                  45

Ser Leu Ile Thr Gly Asp Gly Gly Ser Thr Tyr Tyr Ala Asp Pro Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Val Lys Asp Trp Trp Ile Ala Ala Arg Pro Asp Tyr Tyr Tyr Tyr Gly
            100                 105                 110

Met Asp Val Trp Gly Gln Gly Thr Thr Val Thr Val Ser Ser
        115                 120                 125

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
acattcacct ttgatgattt tgcc                                        24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Thr Phe Thr Phe Asp Asp Phe Ala
 1               5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
attactgggg atggtggtag caca                                        24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Ile Thr Gly Asp Gly Gly Ser Thr
 1               5
```

<210> SEQ ID NO 135
<211> LENGTH: 57
<212> TYPE: DNA
<213> ORGANISM: Artificial Sequence
<220> FEATURE:
<223> OTHER INFORMATION: Synthetic

<400> SEQUENCE: 135
gtaaaagatt ggtggatagc agctcgtccg gactactact actacggtat ggacgtc     57

<210> SEQ ID NO 136
<211> LENGTH: 19
<212> TYPE: PRT
<213> ORGANISM: Artificial Sequence
<220> FEATURE:
<223> OTHER INFORMATION: Synthetic

<400> SEQUENCE: 136

Val Lys Asp Trp Trp Ile Ala Ala Arg Pro Asp Tyr Tyr Tyr Gly
 1               5                  10                  15

Met Asp Val

<210> SEQ ID NO 137
<211> LENGTH: 378
<212> TYPE: DNA
<213> ORGANISM: Artificial Sequence
<220> FEATURE:
<223> OTHER INFORMATION: Synthetic

<400> SEQUENCE: 137
caggtgcagc tgcaggagtc gggcccagga ctggtgaagc cctcggagac cctgtccatc      60
acctgcactg tctctggtgg ctccttcagt agtcacttct ggacctggat ccggcagccc     120
ccaggaaagg gactggaatg gattggatat ctccattata gtgggggcac cagctacaac     180
ccctccctca gagtcgagt catcatatca gtggacacgt ccaagaacca gttctccctg     240
aaactgaact ctgtgaccgc tgcggacacg gccgtgtatt actgtgcgag agctagatcg     300
gggattactt ttgggggact tatcgtccct ggttcttttg atatctgggg ccaagggaca     360
atggtcaccg tctcttca                                                   378

<210> SEQ ID NO 138
<211> LENGTH: 126
<212> TYPE: PRT
<213> ORGANISM: Artificial Sequence
<220> FEATURE:
<223> OTHER INFORMATION: Synthetic

<400> SEQUENCE: 138

Gln Val Gln Leu Gln Glu Ser Gly Pro Gly Leu Val Lys Pro Ser Glu
 1               5                  10                  15

Thr Leu Ser Ile Thr Cys Thr Val Ser Gly Gly Ser Phe Ser Ser His
                20                  25                  30

Phe Trp Thr Trp Ile Arg Gln Pro Pro Gly Lys Gly Leu Glu Trp Ile
            35                  40                  45

Gly Tyr Leu His Tyr Ser Gly Gly Thr Ser Tyr Asn Pro Ser Leu Lys
        50                  55                  60

Ser Arg Val Ile Ile Ser Val Asp Thr Ser Lys Asn Gln Phe Ser Leu
 65                  70                  75                  80

Lys Leu Asn Ser Val Thr Ala Ala Asp Thr Ala Val Tyr Tyr Cys Ala
                85                  90                  95

Arg Ala Arg Ser Gly Ile Thr Phe Gly Gly Leu Ile Val Pro Gly Ser
            100                 105                 110

Phe Asp Ile Trp Gly Gln Gly Thr Met Val Thr Val Ser Ser
        115                 120                 125

<210> SEQ ID NO 139
<211> LENGTH: 24
<212> TYPE: DNA
<213> ORGANISM: Artificial Sequence
<220> FEATURE:
<223> OTHER INFORMATION: Synthetic

<400> SEQUENCE: 139
ggtggctcct tcagtagtca cttc                                          24

<210> SEQ ID NO 140
<211> LENGTH: 8
<212> TYPE: PRT
<213> ORGANISM: Artificial Sequence
<220> FEATURE:
<223> OTHER INFORMATION: Synthetic

<400> SEQUENCE: 140

Gly Gly Ser Phe Ser Ser His Phe
 1               5

<210> SEQ ID NO 141
<211> LENGTH: 21
<212> TYPE: DNA
<213> ORGANISM: Artificial Sequence
<220> FEATURE:
<223> OTHER INFORMATION: Synthetic

<400> SEQUENCE: 141
ctccattata gtgggggcac c                                             21

<210> SEQ ID NO 142
<211> LENGTH: 7
<212> TYPE: PRT
<213> ORGANISM: Artificial Sequence
<220> FEATURE:
<223> OTHER INFORMATION: Synthetic

<400> SEQUENCE: 142

Leu His Tyr Ser Gly Gly Thr
 1               5

<210> SEQ ID NO 143
<211> LENGTH: 60
<212> TYPE: DNA
<213> ORGANISM: Artificial Sequence
<220> FEATURE:
<223> OTHER INFORMATION: Synthetic

<400> SEQUENCE: 143
gcgagagcta gatcggggat tactttgggg ggacttatcg tccctggttc ttttgatatc   60

<210> SEQ ID NO 144
<211> LENGTH: 20
<212> TYPE: PRT
<213> ORGANISM: Artificial Sequence
<220> FEATURE:
<223> OTHER INFORMATION: Synthetic

<400> SEQUENCE: 144

Ala Arg Ala Arg Ser Gly Ile Thr Phe Gly Gly Leu Ile Val Pro Gly

<210> SEQ ID NO 145
<211> LENGTH: 324
<212> TYPE: DNA
<213> ORGANISM: Artificial Sequence
<220> FEATURE:
<223> OTHER INFORMATION: Synthetic

<400> SEQUENCE: 145

```
gaaatagttt tgacacagag tcccggcaca ctgtcactct ctcccgggga aagagccacc    60
ttgtcatgta gagcaagtca gtcagtctct agctcttatc tcgcctggta ccagcagaag   120
ccgggacagg ccctagact gctgatctac ggggcaagtt ccagggccac cggaatcccc    180
gaccggttca gtggaagcgg aagcggaacc gatttactt tgacgatttc tagactggag    240
ccagaggatt tcgccgttta ctattgtcaa cagtacggaa gcagcccgtg acgtttggc    300
cagggcacga aggtagaaat caag                                           324
```

<210> SEQ ID NO 146
<211> LENGTH: 108
<212> TYPE: PRT
<213> ORGANISM: Artificial Sequence
<220> FEATURE:
<223> OTHER INFORMATION: Synthetic

<400> SEQUENCE: 146

```
Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Ser Ser Ser
             20                  25                  30
Tyr Leu Ala Trp Tyr Gln Gln Lys Pro Gly Gln Ala Pro Arg Leu Leu
         35                  40                  45
Ile Tyr Gly Ala Ser Ser Arg Ala Thr Gly Ile Pro Asp Arg Phe Ser
     50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Trp Thr Phe Gly Gln Gly Thr Lys Val Glu Ile Lys
            100                 105
```

<210> SEQ ID NO 147
<211> LENGTH: 21
<212> TYPE: DNA
<213> ORGANISM: Artificial Sequence
<220> FEATURE:
<223> OTHER INFORMATION: Synthetic

<400> SEQUENCE: 147

```
cagtcagtct ctagctctta t                                              21
```

<210> SEQ ID NO 148
<211> LENGTH: 7
<212> TYPE: PRT
<213> ORGANISM: Artificial Sequence
<220> FEATURE:
<223> OTHER INFORMATION: Synthetic

<400> SEQUENCE: 148

Gln Ser Val Ser Ser Ser Tyr
 1               5

<210> SEQ ID NO 149
<211> LENGTH: 9
<212> TYPE: DNA
<213> ORGANISM: Artificial Sequence
<220> FEATURE:
<223> OTHER INFORMATION: Synthetic

<400> SEQUENCE: 149 ggggcaagt                                                                   9

<210> SEQ ID NO 150
<211> LENGTH: 3
<212> TYPE: PRT
<213> ORGANISM: Artificial Sequence
<220> FEATURE:
<223> OTHER INFORMATION: Synthetic

<400> SEQUENCE: 150

Gly Ala Ser
 1

<210> SEQ ID NO 151
<211> LENGTH: 27
<212> TYPE: DNA
<213> ORGANISM: Artificial Sequence
<220> FEATURE:
<223> OTHER INFORMATION: Synthetic

<400> SEQUENCE: 151
caacagtacg gaagcagccc gtggacg                                              27

<210> SEQ ID NO 152
<211> LENGTH: 9
<212> TYPE: PRT
<213> ORGANISM: Artificial Sequence
<220> FEATURE:
<223> OTHER INFORMATION: Synthetic

<400> SEQUENCE: 152

Gln Gln Tyr Gly Ser Ser Pro Trp Thr
 1               5

<210> SEQ ID NO 153
<211> LENGTH: 378
<212> TYPE: DNA
<213> ORGANISM: Artificial Sequence
<220> FEATURE:
<223> OTHER INFORMATION: Synthetic

<400> SEQUENCE: 153
caggtgcagc tgcaggagtc gggcccagga ctggtgaagc cttcggagac cctgtccctc          60
atttgttctg tctctggtgg ctccttcagt agtcacttct ggagttggat ccggcagccc         120
ccagggaagg gactggagtg gattgggtat gtcctttaca gtgggggcac caattacaac         180
ccctccctca agagtcgagt caccatatca gtagacacgt ccaagaatca gttcttcctg         240
aaactgagct ctgtgaccgc tgcggacacg gccgattatt actgtgcgag agctatatcg         300
gggattacgt ttgggggaat tatcgtccct ggttcttttg atatctgggg ccaagggaca         360
atggtcaccg tctcttca                                                       378

<210> SEQ ID NO 154
<211> LENGTH: 126
<212> TYPE: PRT
<213> ORGANISM: Artificial Sequence
<220> FEATURE:
<223> OTHER INFORMATION: Synthetic

<400> SEQUENCE: 154

```
Gln Val Gln Leu Gln Glu Ser Gly Pro Gly Leu Val Lys Pro Ser Glu
 1               5                  10                  15
Thr Leu Ser Leu Ile Cys Ser Val Ser Gly Gly Ser Phe Ser Ser His
            20                  25                  30
Phe Trp Ser Trp Ile Arg Gln Pro Pro Gly Lys Gly Leu Glu Trp Ile
        35                  40                  45
Gly Tyr Val Leu Tyr Ser Gly Gly Thr Asn Tyr Asn Pro Ser Leu Lys
    50                  55                  60
Ser Arg Val Thr Ile Ser Val Asp Thr Ser Lys Asn Gln Phe Phe Leu
65                  70                  75                  80
Lys Leu Ser Ser Val Thr Ala Ala Asp Thr Ala Asp Tyr Tyr Cys Ala
                85                  90                  95
Arg Ala Ile Ser Gly Ile Thr Phe Gly Gly Ile Ile Val Pro Gly Ser
            100                 105                 110
Phe Asp Ile Trp Gly Gln Gly Thr Met Val Thr Val Ser Ser
        115                 120                 125
```

<210> SEQ ID NO 155
<211> LENGTH: 24
<212> TYPE: DNA
<213> ORGANISM: Artificial Sequence
<220> FEATURE:
<223> OTHER INFORMATION: Synthetic

<400> SEQUENCE: 155
ggtggctcct tcagtagtca cttc                                          24

<210> SEQ ID NO 156
<211> LENGTH: 8
<212> TYPE: PRT
<213> ORGANISM: Artificial Sequence
<220> FEATURE:
<223> OTHER INFORMATION: Synthetic

<400> SEQUENCE: 156

```
Gly Gly Ser Phe Ser Ser His Phe
 1               5
```

<210> SEQ ID NO 157
<211> LENGTH: 21
<212> TYPE: DNA
<213> ORGANISM: Artificial Sequence
<220> FEATURE:
<223> OTHER INFORMATION: Synthetic

<400> SEQUENCE: 157
gtcctttaca gtgggggcac c                                             21

<210> SEQ ID NO 158
<211> LENGTH: 7
<212> TYPE: PRT
<213> ORGANISM: Artificial Sequence
<220> FEATURE:
<223> OTHER INFORMATION: Synthetic

<400> SEQUENCE: 158

Val Leu Tyr Ser Gly Gly Thr
 1               5

<210> SEQ ID NO 159
<211> LENGTH: 60
<212> TYPE: DNA
<213> ORGANISM: Artificial Sequence
<220> FEATURE:
<223> OTHER INFORMATION: Synthetic

<400> SEQUENCE: 159
gcgagagcta tatcggggat tacgtttggg ggaattatcg tccctggttc ttttgatatc        60

<210> SEQ ID NO 160
<211> LENGTH: 20
<212> TYPE: PRT
<213> ORGANISM: Artificial Sequence
<220> FEATURE:
<223> OTHER INFORMATION: Synthetic

<400> SEQUENCE: 160

Ala Arg Ala Ile Ser Gly Ile Thr Phe Gly Gly Ile Ile Val Pro Gly
 1               5                  10                  15

Ser Phe Asp Ile
            20

<210> SEQ ID NO 161
<211> LENGTH: 378
<212> TYPE: DNA
<213> ORGANISM: Artificial Sequence
<220> FEATURE:
<223> OTHER INFORMATION: Synthetic

<400> SEQUENCE: 161
caggtgcagc tgcaggagtc gggcccagga ctggtgaagc cctcggagac cctgtccctc        60
acctgcactg tctctggtgg ctccttcagt agtcacttct ggagctggat ccggcagccc       120
ccagggaagg gactggagtg gattggatat atcttataca ctgggggcac cagcttcaac       180
ccctccctca agagtcgagt ctccatgtca gtgggcacgt ccaagaacca gttctccctg       240
aaattgagct ctgtgaccgc tgcggacacg gccgtatatt actgtgcgag agctagatcg       300
gggataacgt ttacgggtat tatcgtccct ggctcttttg atatctgggg ccaagggaca       360
atggtcaccg tctcttca                                                    378

<210> SEQ ID NO 162
<211> LENGTH: 126
<212> TYPE: PRT
<213> ORGANISM: Artificial Sequence
<220> FEATURE:
<223> OTHER INFORMATION: Synthetic

<400> SEQUENCE: 162

Gln Val Gln Leu Gln Glu Ser Gly Pro Gly Leu Val Lys Pro Ser Glu
 1               5                  10                  15

Thr Leu Ser Leu Thr Cys Thr Val Ser Gly Gly Ser Phe Ser His
                20                  25                  30

Phe Trp Ser Trp Ile Arg Gln Pro Pro Gly Lys Gly Leu Glu Trp Ile
            35                  40                  45

Gly Tyr Ile Leu Tyr Thr Gly Gly Thr Ser Phe Asn Pro Ser Leu Lys
        50                  55                  60

Ser Arg Val Ser Met Ser Val Gly Thr Ser Lys Asn Gln Phe Ser Leu

```
                65                  70                  75                  80
Lys Leu Ser Ser Val Thr Ala Ala Asp Thr Ala Val Tyr Tyr Cys Ala
                        85                  90                  95

Arg Ala Arg Ser Gly Ile Thr Phe Thr Gly Ile Ile Val Pro Gly Ser
                    100                 105                 110

Phe Asp Ile Trp Gly Gln Gly Thr Met Val Thr Val Ser Ser
                115                 120                 125
```

<210> SEQ ID NO 163
<211> LENGTH: 24
<212> TYPE: DNA
<213> ORGANISM: Artificial Sequence
<220> FEATURE:
<223> OTHER INFORMATION: Synthetic

<400> SEQUENCE: 163
ggtggctcct tcagtagtca cttc                                          24

<210> SEQ ID NO 164
<211> LENGTH: 8
<212> TYPE: PRT
<213> ORGANISM: Artificial Sequence
<220> FEATURE:
<223> OTHER INFORMATION: Synthetic

<400> SEQUENCE: 164

Gly Gly Ser Phe Ser Ser His Phe
1               5

<210> SEQ ID NO 165
<211> LENGTH: 21
<212> TYPE: DNA
<213> ORGANISM: Artificial Sequence
<220> FEATURE:
<223> OTHER INFORMATION: Synthetic

<400> SEQUENCE: 165
atcttataca ctgggggcac c                                             21

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Ile Leu Tyr Thr Gly Gly Thr
1               5

<210> SEQ ID NO 167
<211> LENGTH: 60
<212> TYPE: DNA
<213> ORGANISM: Artificial Sequence
<220> FEATURE:
<223> OTHER INFORMATION: Synthetic

<400> SEQUENCE: 167
gcgagagcta gatcggggat aacgtttacg ggtattatcg tccctggctc ttttgatatc   60

<210> SEQ ID NO 168
<211> LENGTH: 20
<212> TYPE: PRT
<213> ORGANISM: Artificial Sequence
<220> FEATURE:

<223> OTHER INFORMATION: Synthetic

<400> SEQUENCE: 168

Ala Arg Ala Arg Ser Gly Ile Thr Phe Thr Gly Ile Ile Val Pro Gly
 1               5                  10                  15

Ser Phe Asp Ile
            20

<210> SEQ ID NO 169
<211> LENGTH: 378
<212> TYPE: DNA
<213> ORGANISM: Artificial Sequence
<220> FEATURE:
<223> OTHER INFORMATION: Synthetic

<400> SEQUENCE: 169
caggtgcagc tgcaggagtc gggcccagga ctggtgaagc cttcggagac cctgtccctc      60
acttgttctg tctctggtgg ctccttcagt agtcacttct ggagctggat ccggcagccc     120
ccagggaagg gactggagtg gattggatat atccattaca gtgggggcac caattacaac     180
ccctccctca agagtcgagt caccatatca gtagacacgt ccaagaacca gttctccctt     240
aaactgactt ctgtgaccgc tgcggacacg gccgattatt actgtgcgag agctatatcg     300
gggattacgt ttgggggaat gatcgtccct ggttcttttg atgtctgggg cgaagggaca     360
atggtcaccg tctcttca                                                   378

<210> SEQ ID NO 170
<211> LENGTH: 126
<212> TYPE: PRT
<213> ORGANISM: Artificial Sequence
<220> FEATURE:
<223> OTHER INFORMATION: Synthetic

<400> SEQUENCE: 170

Gln Val Gln Leu Gln Glu Ser Gly Pro Gly Leu Val Lys Pro Ser Glu
 1               5                  10                  15

Thr Leu Ser Leu Thr Cys Ser Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile His Tyr Ser Gly Gly Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Asp Tyr Tyr Cys Ala
                85                  90                  95

Arg Ala Ile Ser Gly Ile Thr Phe Gly Gly Met Ile Val Pro Gly Ser
            100                 105                 110

Phe Asp Val Trp Gly Glu Gly Thr Met Val Thr Val Ser Ser
        115                 120                 125

<210> SEQ ID NO 171
<211> LENGTH: 24
<212> TYPE: DNA
<213> ORGANISM: Artificial Sequence
<220> FEATURE:
<223> OTHER INFORMATION: Synthetic

<400> SEQUENCE: 171
ggtggctcct tcagtagtca cttc                                             24

<210> SEQ ID NO 172
<211> LENGTH: 8
<212> TYPE: PRT
<213> ORGANISM: Artificial Sequence
<220> FEATURE:
<223> OTHER INFORMATION: Synthetic

<400> SEQUENCE: 172

Gly Gly Ser Phe Ser Ser His Phe
 1               5

<210> SEQ ID NO 173
<211> LENGTH: 21
<212> TYPE: DNA
<213> ORGANISM: Artificial Sequence
<220> FEATURE:
<223> OTHER INFORMATION: Synthetic

<400> SEQUENCE: 173
atccattaca gtgggggcac c                                             21

<210> SEQ ID NO 174
<211> LENGTH: 7
<212> TYPE: PRT
<213> ORGANISM: Artificial Sequence
<220> FEATURE:
<223> OTHER INFORMATION: Synthetic

<400> SEQUENCE: 174

Ile His Tyr Ser Gly Gly Thr
 1               5

<210> SEQ ID NO 175
<211> LENGTH: 60
<212> TYPE: DNA
<213> ORGANISM: Artificial Sequence
<220> FEATURE:
<223> OTHER INFORMATION: Synthetic

<400> SEQUENCE: 175
gcgagagcta tatcgggat tacgtttggg ggaatgatcg tccctggttc ttttgatgtc    60

<210> SEQ ID NO 176
<211> LENGTH: 20
<212> TYPE: PRT
<213> ORGANISM: Artificial Sequence
<220> FEATURE:
<223> OTHER INFORMATION: Synthetic

<400> SEQUENCE: 176

Ala Arg Ala Ile Ser Gly Ile Thr Phe Gly Gly Met Ile Val Pro Gly
 1               5                  10                  15

Ser Phe Asp Val
             20

<210> SEQ ID NO 177
<211> LENGTH: 378
<212> TYPE: DNA
<213> ORGANISM: Artificial Sequence
<220> FEATURE:
<223> OTHER INFORMATION: Synthetic

<400> SEQUENCE: 177
caggtgcagc tgcaggagtc gggcccagga ctggtgaagc cttcggagac cctgtccctc    60

```
acctgcactg tctctggtgg caccttcagt agtcacttct ggagctggat ccggcagccc    120
ccaggaaagg gactggagtg gattggatat atcttttaca ctgggggcac caaccacaac    180
ccctccctca agagtcgagt caccatatca atagacacgt ccaagaacca gttctccctg    240
aaactgacct ctgtgaccgc tgcggacacg gccgtgtatt actgtgcgag agctagatcg    300
gggattacgt ttgggggagt tatcgtccct ggttcttttg atatctgggg ccaagggaca    360
atggtcaccg tctcttca                                                  378
```

<210> SEQ ID NO 178
<211> LENGTH: 126
<212> TYPE: PRT
<213> ORGANISM: Artificial Sequence
<220> FEATURE:
<223> OTHER INFORMATION: Synthetic

<400> SEQUENCE: 178

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Thr Phe Ser Ser His
            20                  25                  30

Phe Trp Ser Trp Ile Arg Gln Pro Pro Gly Lys Gly Leu Glu Trp Ile
        35                  40                  45

Gly Tyr Ile Phe Tyr Thr Gly Gly Thr Asn His Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Ala Arg Ser Gly Ile Thr Phe Gly Gly Val Ile Val Pro Gly Ser
            100                 105                 110

Phe Asp Ile Trp Gly Gln Gly Thr Met Val Thr Val Ser Ser
        115                 120                 125

<210> SEQ ID NO 179
<211> LENGTH: 24
<212> TYPE: DNA
<213> ORGANISM: Artificial Sequence
<220> FEATURE:
<223> OTHER INFORMATION: Synthetic

<400> SEQUENCE: 179

```
ggtggcacct tcagtagtca cttc                                            24
```

<210> SEQ ID NO 180
<211> LENGTH: 8
<212> TYPE: PRT
<213> ORGANISM: Artificial Sequence
<220> FEATURE:
<223> OTHER INFORMATION: Synthetic

<400> SEQUENCE: 180

Gly Gly Thr Phe Ser Ser His Phe
1               5

<210> SEQ ID NO 181
<211> LENGTH: 21
<212> TYPE: DNA
<213> ORGANISM: Artificial Sequence
<220> FEATURE:
<223> OTHER INFORMATION: Synthetic

<400> SEQUENCE: 181
atcttttaca ctgggggcac c                                          21

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Ile Phe Tyr Thr Gly Gly Thr
1               5

<210> SEQ ID NO 183
<211> LENGTH: 60
<212> TYPE: DNA
<213> ORGANISM: Artificial Sequence
<220> FEATURE:
<223> OTHER INFORMATION: Synthetic

<400> SEQUENCE: 183
gcgagagcta gatcggggat tacgtttggg ggagttatcg tccctggttc ttttgatatc    60

<210> SEQ ID NO 184
<211> LENGTH: 20
<212> TYPE: PRT
<213> ORGANISM: Artificial Sequence
<220> FEATURE:
<223> OTHER INFORMATION: Synthetic

<400> SEQUENCE: 184

Ala Arg Ala Arg Ser Gly Ile Thr Phe Gly Gly Val Ile Val Pro Gly
1               5                   10                  15

Ser Phe Asp Ile
            20

<210> SEQ ID NO 185
<211> LENGTH: 378
<212> TYPE: DNA
<213> ORGANISM: Artificial Sequence
<220> FEATURE:
<223> OTHER INFORMATION: Synthetic

<400> SEQUENCE: 185
caggtgcagc tgcaggagtc gggcccagga ctggtgaaac cttcggagac cctgtccctc    60
acctgcactg tctctggtgg ctccttcagc agtcacttct ggaactggat ccggcagtcc   120
ccagggaggg gactggaatg gattggatat atctattaca gtgggggcac caactataac   180
ccctccttca agagtcgagt caccatgtca gtagacacgt ccaagaacca gttctccctg   240
aaactgagct ctgtgaccgc tgcggacacg gccgtgtttt actgtgcgag agctagatcg   300
gggataacgt ttgggggagt tctcgtccct ggttcttttg atatttgggg ccaagggaca   360
atggtcaccg tctcttca                                                378

<210> SEQ ID NO 186
<211> LENGTH: 126
<212> TYPE: PRT
<213> ORGANISM: Artificial Sequence
<220> FEATURE:
<223> OTHER INFORMATION: Synthetic

<400> SEQUENCE: 186

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30

Phe Trp Asn Trp Ile Arg Gln Ser Pro Gly Arg Gly Leu Glu Trp Ile
        35                  40                  45

Gly Tyr Ile Tyr Tyr Ser Gly Gly Thr Asn Tyr Asn Pro Ser Phe Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Phe Tyr Cys Ala
                85                  90                  95

Arg Ala Arg Ser Gly Ile Thr Phe Gly Val Leu Val Pro Gly Ser
            100                 105                 110

Phe Asp Ile Trp Gly Gln Gly Thr Met Val Thr Val Ser Ser
        115                 120                 125
```

<210> SEQ ID NO 187
<211> LENGTH: 24
<212> TYPE: DNA
<213> ORGANISM: Artificial Sequence
<220> FEATURE:
<223> OTHER INFORMATION: Synthetic

<400> SEQUENCE: 187
ggtggctcct tcagcagtca cttc                                              24

<210> SEQ ID NO 188
<211> LENGTH: 8
<212> TYPE: PRT
<213> ORGANISM: Artificial Sequence
<220> FEATURE:
<223> OTHER INFORMATION: Synthetic

<400> SEQUENCE: 188

```
Gly Gly Ser Phe Ser Ser His Phe
1               5
```

<210> SEQ ID NO 189
<211> LENGTH: 21
<212> TYPE: DNA
<213> ORGANISM: Artificial Sequence
<220> FEATURE:
<223> OTHER INFORMATION: Synthetic

<400> SEQUENCE: 189
atctattaca gtgggggcac c                                                 21

<210> SEQ ID NO 190
<211> LENGTH: 7
<212> TYPE: PRT
<213> ORGANISM: Artificial Sequence
<220> FEATURE:
<223> OTHER INFORMATION: Synthetic

<400> SEQUENCE: 190

```
Ile Tyr Tyr Ser Gly Gly Thr
1               5
```

<210> SEQ ID NO 191
<211> LENGTH: 60
<212> TYPE: DNA
<213> ORGANISM: Artificial Sequence
<220> FEATURE:
<223> OTHER INFORMATION: Synthetic

<400> SEQUENCE: 191
gcgagagcta gatcggggat aacgtttggg ggagttctcg tccctggttc ttttgatatt    60

<210> SEQ ID NO 192
<211> LENGTH: 20
<212> TYPE: PRT
<213> ORGANISM: Artificial Sequence
<220> FEATURE:
<223> OTHER INFORMATION: Synthetic

<400> SEQUENCE: 192

Ala Arg Ala Arg Ser Gly Ile Thr Phe Gly Gly Val Leu Val Pro Gly
1               5                   10                  15

Ser Phe Asp Ile
            20

<210> SEQ ID NO 193
<211> LENGTH: 378
<212> TYPE: DNA
<213> ORGANISM: Artificial Sequence
<220> FEATURE:
<223> OTHER INFORMATION: Synthetic

<400> SEQUENCE: 193
caggtgcagc tgcaggagtc gggcccagga ctggtgaagc cttcggagac cctgtccctc    60
acctgcactg tctctggtgg ctccttcagt agtcacttct ggagctggat ccggcagccc   120
ccaggaaagg gactggagtg gattgggtat atctattaca gtggggggcac ccactacaac   180 ccctccctcg agagtcgagt caccatatca gtagacacgt ccaagaacca gttctccctg   240
aaactgaact ctgtgaccgc tgcggacacg gccgtttatt actgtgcgag agctagatcg   300
gggattactt ttgggggact tatcgtccct ggttcttttg atatctgggg ccaagggaca   360
atggtcaccg tctcttca                                                 378

<210> SEQ ID NO 194
<211> LENGTH: 126
<212> TYPE: PRT
<213> ORGANISM: Artificial Sequence
<220> FEATURE:
<223> OTHER INFORMATION: Synthetic

<400> SEQUENCE: 194

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Phe Ser Ser His
            20                  25                  30

Phe Trp Ser Trp Ile Arg Gln Pro Pro Gly Lys Gly Leu Glu Trp Ile
        35                  40                  45

Gly Tyr Ile Tyr Tyr Ser Gly Gly Thr His Tyr Asn Pro Ser Leu Glu
    50                  55                  60

Ser Arg Val Thr Ile Ser Val Asp Thr Ser Lys Asn Gln Phe Ser Leu
65                  70                  75                  80

Lys Leu Asn Ser Val Thr Ala Ala Asp Thr Ala Val Tyr Tyr Cys Ala
                85                  90                  95

Arg Ala Arg Ser Gly Ile Thr Phe Gly Gly Leu Ile Val Pro Gly Ser
            100                 105                 110

Phe Asp Ile Trp Gly Gln Gly Thr Met Val Thr Val Ser Ser

<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195
ggtggctcct tcagtagtca cttc                                          24

<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Gly Ser Phe Ser Ser His Phe
 1               5

<210> SEQ ID NO 197
<211> LENGTH: 21
<212> TYPE: DNA
<213> ORGANISM: Artificial Sequence
<220> FEATURE:
<223> OTHER INFORMATION: Synthetic

<400> SEQUENCE: 197
atctattaca gtgggggcac c                                             21

<210> SEQ ID NO 198
<211> LENGTH: 7
<212> TYPE: PRT
<213> ORGANISM: Artificial Sequence
<220> FEATURE:
<223> OTHER INFORMATION: Synthetic

<400> SEQUENCE: 198

Ile Tyr Tyr Ser Gly Gly Thr
 1               5

<210> SEQ ID NO 199
<211> LENGTH: 60
<212> TYPE: DNA
<213> ORGANISM: Artificial Sequence
<220> FEATURE:
<223> OTHER INFORMATION: Synthetic

<400> SEQUENCE: 199
gcgagagcta gatcggggat tactttttggg ggacttatcg tccctggttc ttttgatatc    60

<210> SEQ ID NO 200
<211> LENGTH: 20
<212> TYPE: PRT
<213> ORGANISM: Artificial Sequence
<220> FEATURE:
<223> OTHER INFORMATION: Synthetic

<400> SEQUENCE: 200

Ala Arg Ala Arg Ser Gly Ile Thr Phe Gly Gly Leu Ile Val Pro Gly
 1               5                  10                  15

Ser Phe Asp Ile
            20

<210> SEQ ID NO 201
<211> LENGTH: 375
<212> TYPE: DNA
<213> ORGANISM: Artificial Sequence
<220> FEATURE:
<223> OTHER INFORMATION: Synthetic

<400> SEQUENCE: 201
cgggtgcaac tggtgcagtc tgggtctgag gtgaagaagc ctggggcctc agtgaaggtc 60
tcctgcaggg cttctggata catcttcacc agttatgata tcaattgggt gcgacaggcc 120
actggacaag ggcttgagtg gatgggatgg atgaacccta ataatggtaa cacagcctat 180
acacagaagt tccagggcag agtcaccatg accaggaaca cctccataag cacagcctac 240
atggagctga gcagcctgag atctgaggac acggccgtgt attactgtgc gagaaaggga 300
ttactatggt tcgggaagtt attagggtac ggtatggacg tctggggcca agggaccacg 360
gtcaccgtct cctca 375

<210> SEQ ID NO 202
<211> LENGTH: 125
<212> TYPE: PRT
<213> ORGANISM: Artificial Sequence
<220> FEATURE:
<223> OTHER INFORMATION: Synthetic

<400> SEQUENCE: 202

Arg Val Gln Leu Val Gln Ser Gly Ser Glu Val Lys Lys Pro Gly Ala
1 5 10 15

Ser Val Lys Val Ser Cys Arg Ala Ser Gly Tyr Ile Phe Thr Ser Tyr
20 25 30

Asp Ile Asn Trp Val Arg Gln Ala Thr Gly Gln Gly Leu Glu Trp Met
35 40 45

Gly Trp Met Asn Pro Asn Asn Gly Asn Thr Ala Tyr Thr Gln Lys Phe
50 55 60

Gln Gly Arg Val Thr Met Thr Arg Asn Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Lys Gly Leu Leu Trp Phe Gly Lys Leu Leu Gly Tyr Gly Met
100 105 110

Asp Val Trp Gly Gln Gly Thr Thr Val Thr Val Ser Ser
115 120 125

<210> SEQ ID NO 203
<211> LENGTH: 24
<212> TYPE: DNA
<213> ORGANISM: Artificial Sequence
<220> FEATURE:
<223> OTHER INFORMATION: Synthetic

<400> SEQUENCE: 203
ggatacatct tcaccagtta tgat 24

<210> SEQ ID NO 204
<211> LENGTH: 8
<212> TYPE: PRT
<213> ORGANISM: Artificial Sequence
<220> FEATURE:
<223> OTHER INFORMATION: Synthetic

<400> SEQUENCE: 204

Gly Tyr Ile Phe Thr Ser Tyr Asp
1               5

<210> SEQ ID NO 205
<211> LENGTH: 24
<212> TYPE: DNA
<213> ORGANISM: Artificial Sequence
<220> FEATURE:
<223> OTHER INFORMATION: Synthetic

<400> SEQUENCE: 205
atgaacccta ataatggtaa caca                                          24

<210> SEQ ID NO 206
<211> LENGTH: 8
<212> TYPE: PRT
<213> ORGANISM: Artificial Sequence
<220> FEATURE:
<223> OTHER INFORMATION: Synthetic

<400> SEQUENCE: 206

Met Asn Pro Asn Asn Gly Asn Thr
1               5

<210> SEQ ID NO 207
<211> LENGTH: 54
<212> TYPE: DNA
<213> ORGANISM: Artificial Sequence
<220> FEATURE:
<223> OTHER INFORMATION: Synthetic

<400> SEQUENCE: 207
gcgagaaagg gattactatg gttcgggaag ttattagggt acggtatgga cgtc         54

<210> SEQ ID NO 208
<211> LENGTH: 18
<212> TYPE: PRT
<213> ORGANISM: Artificial Sequence
<220> FEATURE:
<223> OTHER INFORMATION: Synthetic

<400> SEQUENCE: 208

Ala Arg Lys Gly Leu Leu Trp Phe Gly Lys Leu Leu Gly Tyr Gly Met
1               5                   10                  15

Asp Val

<210> SEQ ID NO 209
<211> LENGTH: 324
<212> TYPE: DNA
<213> ORGANISM: Artificial Sequence
<220> FEATURE:
<223> OTHER INFORMATION: Synthetic

<400> SEQUENCE: 209
gaaattgtgt tgacgcagtc tccaggcacc ctgtctttgt ctccagggga aagagccacc   60
ctctcctgca gggccagtca gagtgttagc agcagctact tagcctggta ccagcagaaa  120
cctggccagg ctcccaggct cctcatctat ggtgcatcca gcagggccac tggcatccca  180
gacaggttca gtggcagtgg gtctgggaca gacttcactc tcaccatcag cagactggag  240
cctgaagatt ttgcagtgta ttactgtcag cagtatggta gctcaccttg gacgttcggc  300
caagggacca aggtggaaat caaa                                         324

<210> SEQ ID NO 210
<211> LENGTH: 108
<212> TYPE: PRT
<213> ORGANISM: Artificial Sequence
<220> FEATURE:
<223> OTHER INFORMATION: Synthetic

<400> SEQUENCE: 210

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 211
<211> LENGTH: 21
<212> TYPE: DNA
<213> ORGANISM: Artificial Sequence
<220> FEATURE:
<223> OTHER INFORMATION: Synthetic

<400> SEQUENCE: 211
cagagtgtta gcagcagcta c                                           21

<210> SEQ ID NO 212
<211> LENGTH: 7
<212> TYPE: PRT
<213> ORGANISM: Artificial Sequence
<220> FEATURE:
<223> OTHER INFORMATION: Synthetic

<400> SEQUENCE: 212

```
Gln Ser Val Ser Ser Ser Tyr
1               5
```

<210> SEQ ID NO 213
<211> LENGTH: 9
<212> TYPE: DNA
<213> ORGANISM: Artificial Sequence
<220> FEATURE:
<223> OTHER INFORMATION: Synthetic

<400> SEQUENCE: 213 ggtgcatcc                                                          9

<210> SEQ ID NO 214
<211> LENGTH: 3
<212> TYPE: PRT
<213> ORGANISM: Artificial Sequence
<220> FEATURE:
<223> OTHER INFORMATION: Synthetic

<400> SEQUENCE: 214

Gly Ala Ser

-continued

<210> SEQ ID NO 215
<211> LENGTH: 27
<212> TYPE: DNA
<213> ORGANISM: Artificial Sequence
<220> FEATURE:
<223> OTHER INFORMATION: Synthetic

<400> SEQUENCE: 215
cagcagtatg gtagctcacc ttggacg                                        27

<210> SEQ ID NO 216
<211> LENGTH: 9
<212> TYPE: PRT
<213> ORGANISM: Artificial Sequence
<220> FEATURE:
<223> OTHER INFORMATION: Synthetic

<400> SEQUENCE: 216

Gln Gln Tyr Gly Ser Ser Pro Trp Thr
 1               5

<210> SEQ ID NO 217
<211> LENGTH: 120
<212> TYPE: PRT
<213> ORGANISM: Artificial Sequence
<220> FEATURE:
<223> OTHER INFORMATION: Synthetic

<400> SEQUENCE: 217

Glu Val Gln Val Leu Glu Ser Gly Gly Asp Leu Val Gln Pro Gly Gly
 1               5                  10                  15

Ser Leu Arg Leu Ser Cys Ala Ala Ser Gly Phe Thr Phe Ser Ala Tyr
             20                  25                  30

Ala Met Thr Trp Val Arg Gln Ala Pro Gly Lys Gly Leu Glu Trp Val
         35                  40                  45

Ser Ala Ile Ser Gly Ser Gly Gly Ser Ala Tyr Tyr Ala Asp Ser Val
     50                  55                  60

Lys Gly Arg Phe Thr Ile Ser Arg Asp Asn Ser Lys Asn Thr Val Tyr
 65                  70                  75                  80

Leu Gln Met Asn Ser Leu Arg Ala Glu Asp Thr Ala Val Tyr Tyr Cys
                 85                  90                  95

Ala Lys Asp Gly Ala Trp Lys Met Ser Gly Leu Asp Val Trp Gly Gln
            100                 105                 110

Gly Thr Thr Val Ile Val Ser Ser
        115                 120

<210> SEQ ID NO 218
<211> LENGTH: 8
<212> TYPE: PRT
<213> ORGANISM: Artificial Sequence
<220> FEATURE:
<223> OTHER INFORMATION: Synthetic

<400> SEQUENCE: 218

Gly Phe Thr Phe Ser Ala Tyr Ala
 1               5

<210> SEQ ID NO 219
<211> LENGTH: 8
<212> TYPE: PRT
<213> ORGANISM: Artificial Sequence
<220> FEATURE:
<223> OTHER INFORMATION: Synthetic

<400> SEQUENCE: 219

Ile Ser Gly Ser Gly Gly Ser Ala
1               5

<210> SEQ ID NO 220
<211> LENGTH: 13
<212> TYPE: PRT
<213> ORGANISM: Artificial Sequence
<220> FEATURE:
<223> OTHER INFORMATION: Synthetic

<400> SEQUENCE: 220

Ala Lys Asp Gly Ala Trp Lys Met Ser Gly Leu Asp Val
1               5                   10

<210> SEQ ID NO 221
<211> LENGTH: 107
<212> TYPE: PRT
<213> ORGANISM: Artificial Sequence
<220> FEATURE:
<223> OTHER INFORMATION: Synthetic

<400> SEQUENCE: 221

Asp Ile Gln Met Thr Gln Ser Pro Ala Ser Leu Ser Ala Ser Val Gly
1               5                   10                  15

Asp Arg Val Thr Ile Thr Cys Arg Ala Ser Gln Asp Ile Ser Asp Tyr
            20                  25                  30

Leu Ala Trp Tyr Gln Gln Lys Pro Gly Lys Ile Pro Arg Leu Leu Ile
        35                  40                  45

Tyr Thr Thr Ser Thr Leu Gln Ser Gly Val Pro Ser Arg Phe Arg Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asp Ser Ala Pro Leu
                85                  90                  95

Thr Phe Gly Gly Gly Thr Lys Val Glu Ile Lys
            100                 105

<210> SEQ ID NO 222
<211> LENGTH: 6
<212> TYPE: PRT
<213> ORGANISM: Artificial Sequence
<220> FEATURE:
<223> OTHER INFORMATION: Synthetic

<400> SEQUENCE: 222

Gln Asp Ile Ser Asp Tyr
1               5

<210> SEQ ID NO 223
<211> LENGTH: 3
<212> TYPE: PRT
<213> ORGANISM: Artificial Sequence
<220> FEATURE:
<223> OTHER INFORMATION: Synthetic

<400> SEQUENCE: 223

Thr Thr Ser
1

```
<210> SEQ ID NO 224
<211> LENGTH: 9
<212> TYPE: PRT
<213> ORGANISM: Artificial Sequence
<220> FEATURE:
<223> OTHER INFORMATION: Synthetic

<400> SEQUENCE: 224

Gln Lys Tyr Asp Ser Ala Pro Leu Thr
 1               5

<210> SEQ ID NO 225
<211> LENGTH: 109
<212> TYPE: PRT
<213> ORGANISM: Homo sapiens

<400> SEQUENCE: 225

Asp Phe Gly Leu Asp Cys Asp Glu His Ser Thr Glu Ser Arg Cys Cys
 1               5                  10                  15

Arg Tyr Pro Leu Thr Val Asp Phe Glu Ala Phe Gly Trp Asp Trp Ile
             20                  25                  30

Ile Ala Pro Lys Arg Tyr Lys Ala Asn Tyr Cys Ser Gly Glu Cys Glu
         35                  40                  45

Phe Val Phe Leu Gln Lys Tyr Pro His Thr His Leu Val His Gln Ala
     50                  55                  60

Asn Pro Arg Gly Ser Ala Gly Pro Cys Cys Thr Pro Thr Lys Met Ser
 65                  70                  75                  80

Pro Ile Asn Met Leu Tyr Phe Asn Gly Lys Glu Gln Ile Ile Tyr Gly
                 85                  90                  95

Lys Ile Pro Ala Met Val Val Asp Arg Cys Gly Cys Ser
            100                 105

<210> SEQ ID NO 226
<211> LENGTH: 426
<212> TYPE: PRT
<213> ORGANISM: Homo sapiens

<400> SEQUENCE: 226

Met Pro Leu Leu Trp Leu Arg Gly Phe Leu Leu Ala Ser Cys Trp Ile
 1               5                  10                  15

Ile Val Arg Ser Ser Pro Thr Pro Gly Ser Glu Gly His Ser Ala Ala
             20                  25                  30

Pro Asp Cys Pro Ser Cys Ala Leu Ala Ala Leu Pro Lys Asp Val Pro
         35                  40                  45

Asn Ser Gln Pro Glu Met Val Glu Ala Val Lys Lys His Ile Leu Asn
     50                  55                  60

Met Leu His Leu Lys Lys Arg Pro Asp Val Thr Gln Pro Val Pro Lys
 65                  70                  75                  80

Ala Ala Leu Leu Asn Ala Ile Arg Lys Leu His Val Gly Lys Val Gly
                 85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160
```

```
Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Glu Glu Glu Gly Glu Gly Lys Lys Lys
                260                 265                 270

Gly Gly Gly Glu Gly Gly Ala Gly Ala Asp Glu Glu Lys Glu Gln Ser
            275                 280                 285

His Arg Pro Phe Leu Met Leu Gln Ala Arg Gln Ser Glu Asp His Pro
        290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
                340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
        370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425
```

<210> SEQ ID NO 227
<211> LENGTH: 340
<212> TYPE: PRT
<213> ORGANISM: Artificial Sequence
<220> FEATURE:
<223> OTHER INFORMATION: Synthetic

<400> SEQUENCE: 227

```
Glu Ala Glu Thr Arg Glu Cys Ile Tyr Tyr Asn Ala Asn Trp Glu Leu
1               5                   10                  15

Glu Arg Thr Asn Gln Ser Gly Leu Glu Arg Cys Glu Gly Glu Gln Asp
            20                  25                  30

Lys Arg Leu His Cys Tyr Ala Ser Trp Ala Asn Ser Ser Gly Thr Ile
        35                  40                  45

Glu Leu Val Lys Lys Gly Cys Trp Leu Asp Asp Phe Asn Cys Tyr Asp
    50                  55                  60

Arg Gln Glu Cys Val Ala Thr Glu Glu Asn Pro Gln Val Tyr Phe Cys
65                  70                  75                  80

Cys Cys Glu Gly Asn Phe Cys Asn Glu Arg Phe Thr His Leu Pro Glu
                85                  90                  95
```

```
Ala Gly Gly Pro Glu Val Thr Tyr Glu Pro Pro Thr Ala Pro Ser
            100                 105                 110

Gly Asp Lys Thr His Thr Cys Pro Cys Pro Ala Pro Glu Leu Leu
            115                 120                 125

Gly Gly Pro Ser Val Phe Leu Phe Pro Pro Lys Pro Lys Asp Thr Leu
            130                 135                 140

Met Ile Ser Arg Thr Pro Glu Val Thr Cys Val Val Asp Val Ser
145                 150                 155                 160

His Glu Asp Pro Glu Val Lys Phe Asn Trp Tyr Val Asp Gly Val Glu
                    165                 170                 175

Val His Asn Ala Lys Thr Lys Pro Arg Glu Glu Gln Tyr Asn Ser Thr
                    180                 185                 190

Tyr Arg Val Val Ser Val Leu Thr Val Leu His Gln Asp Trp Leu Asn
            195                 200                 205

Gly Lys Glu Tyr Lys Cys Lys Val Ser Asn Lys Ala Leu Pro Ala Pro
            210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Asp Glu Leu Thr Lys Asn Gln Val
                    245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
            275                 280                 285

Pro Val Leu Asp Ser Asp Gly Ser Phe Phe Leu Tyr Ser Lys Leu Thr
            290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                    325                 330                 335

Ser Pro Gly Lys
            340

<210> SEQ ID NO 228
<211> LENGTH: 407
<212> TYPE: PRT
<213> ORGANISM: Homo Sapiens

<400> SEQUENCE: 228

Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
            20                  25                  30

Pro Pro Thr Pro Ala Ala Gln Pro Pro Pro Pro Gly Ser Pro
            35                  40                  45

Gly Gly Ser Gln Asp Thr Cys Thr Ser Cys Gly Gly Phe Arg Arg Pro
            50                  55                  60

Glu Glu Leu Gly Arg Val Asp Gly Asp Phe Leu Glu Ala Val Lys Arg
65                  70                  75                  80

His Ile Leu Ser Arg Leu Gln Met Arg Gly Arg Pro Asn Ile Thr His
                    85                  90                  95

Ala Val Pro Lys Ala Ala Met Val Thr Ala Leu Arg Lys Leu His Ala
            100                 105                 110

Gly Lys Val Arg Glu Asp Gly Arg Val Glu Ile Pro His Leu Asp Gly
            115                 120                 125
```

-continued

```
His Ala Ser Pro Gly Ala Asp Gly Gln Glu Arg Val Ser Glu Ile Ile
    130                 135                 140

Ser Phe Ala Glu Thr Asp Gly Leu Ala Ser Ser Arg Val Arg Leu Tyr
145                 150                 155                 160

Phe Phe Ile Ser Asn Glu Gly Asn Gln Asn Leu Phe Val Val Gln Ala
                165                 170                 175

Ser Leu Trp Leu Tyr Leu Lys Leu Leu Pro Tyr Val Leu Glu Lys Gly
                180                 185                 190

Ser Arg Arg Lys Val Arg Val Lys Val Tyr Phe Gln Glu Gln Gly His
            195                 200                 205

Gly Asp Arg Trp Asn Met Val Glu Lys Arg Val Asp Leu Lys Arg Ser
        210                 215                 220

Gly Trp His Thr Phe Pro Leu Thr Glu Ala Ile Gln Ala Leu Phe Glu
225                 230                 235                 240

Arg Gly Glu Arg Arg Leu Asn Leu Asp Val Gln Cys Asp Ser Cys Gln
                245                 250                 255

Glu Leu Ala Val Val Pro Val Phe Val Asp Pro Gly Glu Glu Ser His
                260                 265                 270

Arg Pro Phe Val Val Val Gln Ala Arg Leu Gly Asp Ser Arg His Arg
        275                 280                 285

Ile Arg Lys Arg Gly Leu Glu Cys Asp Gly Arg Thr Asn Leu Cys Cys
    290                 295                 300

Arg Gln Gln Phe Phe Ile Asp Phe Arg Leu Ile Gly Trp Asn Asp Trp
305                 310                 315                 320

Ile Ile Ala Pro Thr Ser Tyr Tyr Gly Asn Tyr Cys Glu Gly Ser Cys
                325                 330                 335

Pro Ala Tyr Leu Ala Gly Val Pro Gly Ser Ala Ser Ser Phe His Thr
                340                 345                 350

Ala Val Val Asn Gln Tyr Arg Met Arg Gly Leu Asn Pro Gly Thr Val
            355                 360                 365

Asn Ser Cys Cys Ile Pro Thr Lys Leu Ser Thr Met Ser Met Leu Tyr
        370                 375                 380

Phe Asp Asp Glu Tyr Asn Ile Val Lys Arg Asp Val Pro Asn Met Ile
385                 390                 395                 400

Val Glu Glu Cys Gly Cys Ala
                405
```

ANTI-ACTIVIN A ANTIBODIES AND USES THEREOF

FIELD OF THE INVENTION

The present invention relates to antibodies, and antigen-binding fragments thereof, which are specific for Activin A, and methods of use thereof, including methods of using antibodies specific for Activin A in conjunction with a myostatin inhibitor.

BACKGROUND

Activins belong to the transforming growth factor-beta (TGF-β) superfamily and exert a broad range of biological effects on cell proliferation, differentiation, and apoptosis. Activins are homo- or heterodimers of InhibinβA, InhibinβB, InhibinβC and InhibinβE, different combinations of which create the various members of the activin protein group. For example, Activin A is a homodimer of InhibinβA and Activin B is a homodimer of InhibinβB, whereas Activin AB is a heterodimer of InhibinβA and InhibinβB and Activin AC is a heterodimer of InhibinβA and InhibinβC (Tsuchida, K. et al., Cell Commun Signal 7:15 (2009)).

Activin A binds to and activates receptor complexes on the surface of cells known as Activin Type II receptors (Type IIA and Type IIB, also known as ActRIIA and ActRIIB, respectively). The activation of these receptors leads to the phosphorylation of an Activin Type I receptor (e.g., Alk4 or 7), which in turn leads to the phosphorylation of SMAD 2 and 3 proteins, the formation of SMAD complexes (with SMAD4), and the translocation of the SMAD complex to the cell nucleus, where SMAD2 and SMAD3 function to regulate transcription of various genes (Sozzani, S, and Musso, T., Blood 117(19):5013-5015 (2011)).

Numerous other ligands bind to and activate ActRIIB, including GDF8 (myostatin), Activin B, Activin AB, Inhibin A, Inhibin B, GDF3, GDF11, Nodal, BMP2, BMP4, BMP7, BMP9, and BMP10. Blocking the interactions of ActRIIB with its ligands can lead to beneficial physiological effects. For example, GDF8 plays a central role in the development and maintenance of skeletal muscle, acting as a negative regulator of muscle mass (McPherron A C et al. (1997). Nature 387(6628):83-90). Administration of ActRIIB-Fc (i.e., the extracellular portion of the Type IIB receptor, ActRIIB, stabilized by fusion to an IgG Fc domain) leads to significant increases in skeletal muscle mass and improves muscle weight and measurements of muscle strength in mice (Lee S J, et al. (2005) Proc Natl Acad Sci USA 102(50): 18117-18122). The efficacy of ActRIIB-Fc is attenuated but not eliminated in Mstn (myostatin) null mice, demonstrating that other ActRIIB ligand(s) in addition to myostatin can function as negative regulators of muscle growth. Thus, a need exists for additional inhibitors of ActRIIB signaling that can provide clinical benefits.

BRIEF SUMMARY OF THE INVENTION

The present invention provides antibodies that bind inhibin βA and dimers containing inhibin βA, e.g., Activin A, Activin AB, etc. The antibodies of the invention are useful, inter alia, for inhibiting Activin A-mediated signaling, producing beneficial clinical outcomes through the inhibition of Activin A-mediated signaling, e.g., for treating diseases and disorders caused by or related to Activin A activity and/or signaling. The antibodies of the invention also have utility for use in conjunction with inhibitors of other ligands of the ActRIIA and ActRIIB receptors, such as GDF8 inhibitors.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., J Immunol 164:1925-1933 (2000)).

The present invention provides isolated antibodies, or antigen-binding fragments thereof, that specifically bind Activin A with a binding association equilibrium constant ($K_a$) of less than about 500 nM and a dissociation equilibrium constant ($K_D$) of less than about 5 pM as measured in a surface plasmon resonance assay at 25° C. In some embodiments of the invention, the isolated antibodies, or antigen-binding fragments thereof, specifically bind Activin A with a $K_D$ of less than about 4 pM as measured in a surface plasmon resonance assay at 25° C. In some embodiments of the invention, the isolated antibodies, or antigen-binding fragments thereof, specifically bind Activin A with a binding association equilibrium constant ($K_a$) of less than about 500 nM.

The present invention provides isolated antibodies, or antigen-binding fragments thereof, that specifically bind Activin A and block binding of at least one Activin A receptor to Activin A. In some embodiments of the invention, the isolated antibodies, or antigen-binding fragments thereof, block Activin A binding to an Activin A receptor with an $IC_{50}$ value of less than about 80 pM as measured in an in vivo receptor/ligand binding bioassay at 25° C. In some embodiments of the invention, the isolated antibodies, or antigen-binding fragments thereof, block Activin A binding to an Activin A receptor with an $IC_{50}$ value of less than about 60 pM as measured in an in vivo receptor/ligand binding bioassay at 25° C. The present invention also provides isolated antibodies, or antigen-binding fragments thereof, that specifically bind Activin A and block activation of at least one Activin A receptor by Activin A. In some embodiments of the invention, the isolated antibodies, or antigen-binding fragments thereof, do not significantly block binding of Activin A to an Activin Type II receptor. In some embodiments of the invention, the isolated antibodies, or antigen-binding fragments thereof, inhibit binding of Activin A to an Activin A receptor selected from the group consisting of Activin Type IIA receptor (ActRIIA), Activin Type IIB receptor (ActRIIB), and Activin Type I receptor. In some embodiments of the invention, the isolated antibodies, or antigen-binding fragments thereof, inhibit Activin A-mediated activation of SMAD complex signaling.

The present invention provides antibodies, or antigen-binding fragments thereof comprising a heavy chain variable region (HCVR) having an amino acid sequence selected from the group consisting of SEQ ID NO: 2, 18, 34, 50, 66, 82, 98, 106, 114, 122, 130, 138, 154, 162, 170, 178, 186, 194, and 202, or a substantially similar sequence thereof having at least 90%, at least 95%, at least 98% or at least 99% sequence identity.

The present invention also provides an antibody or antigen-binding fragment of an antibody comprising a light chain variable region (LCVR) having an amino acid sequence selected from the group consisting of SEQ ID NO: 10, 26, 42, 58, 74, 90, 146, and 210, or a substantially similar sequence thereof having at least 90%, at least 95%, at least 98% or at least 99% sequence identity.

The present invention also provides an antibody or antigen-binding fragment thereof comprising a HCVR and LCVR (HCVR/LCVR) sequence pair selected from the group consisting of SEQ ID NO: 2/10, 18/26, 34/42, 50/58, 66/74, 82/90, 98/90, 106/90, 114/90, 122/90, 130/90, 138/146, 154/146, 162/146, 170/146, 178/146, 186/146, 194/146, and 202/210.

The present invention also provides an antibody or antigen-binding fragment of an antibody comprising a heavy chain CDR3 (HCDR3) domain having an amino acid sequence selected from the group consisting of SEQ ID NO: 8, 24, 40, 56, 72, 88, 104, 112, 120, 128, 136, 144, 160, 168, 176, 184, 192, 200, and 208, or a substantially similar sequence thereof having at least 90%, at least 95%, at least 98% or at least 99% sequence identity; and a light chain CDR3 (LCDR3) domain having an amino acid sequence selected from the group consisting of SEQ ID NO: 16, 32, 48, 64, 80, 96, 152, and 216, or a substantially similar sequence thereof having at least 90%, at least 95%, at least 98% or at least 99% sequence identity.

In certain embodiments, the antibody or antigen-binding portion of an antibody comprises a HCDR3/LCDR3 amino acid sequence pair selected from the group consisting of SEQ ID NO: 8/16, 24/32, 40/48, 56/64, 72/80, 88/96, 104/96, 112/96, 120/96, 128/96, 136/96, 144/152, 160/152, 168/152, 176/152, 184/152, 192/152, 200/152, and 208/216.

The present invention also provides an antibody or fragment thereof further comprising a heavy chain CDR1 (HCDR1) domain having an amino acid sequence selected from the group consisting of SEQ ID NO: 4, 20, 36, 52, 68, 84, 100, 108, 116, 124, 132, 140, 156, 164, 172, 180, 188, 196, and 204, or a substantially similar sequence thereof having at least 90%, at least 95%, at least 98% or at least 99% sequence identity; a heavy chain CDR2 (HCDR2) domain having an amino acid sequence selected from the group consisting of SEQ ID NO: 6, 22, 38, 54, 70, 86, 102, 110, 118, 126, 134, 142, 158, 166, 174, 182, 190, 198, and 206, or a substantially similar sequence thereof having at least 90%, at least 95%, at least 98% or at least 99% sequence identity; a light chain CDR1 (LCDR1) domain having an amino acid sequence selected from the group consisting of SEQ ID NO: 12, 28, 44, 60, 76, 92, 148, and 212, or a substantially similar sequence thereof having at least 90%, at least 95%, at least 98% or at least 99% sequence identity; and a light chain CDR2 (LCDR2) domain having an amino acid sequence selected from the group consisting of SEQ ID NO: 14, 30, 46, 62, 78, 94, 150, and 214, or a substantially similar sequence thereof having at least 90%, at least 95%, at least 98% or at least 99% sequence identity.

Certain non-limiting, exemplary antibodies and antigen-binding fragments of the invention comprise HCDR1-HCDR2-HCDR3-LCDR1-LCDR2-LCDR3 domains, respectively, having the amino acid sequences selected from the group consisting of: SEQ ID NOs: 4-6-8-12-14-16 (e.g. H4H10423P); 20-22-24-28-30-32 (e.g. H4H10424P); 36-38-40-44-46-48 (e.g. H4H10426P); 52-54-56-60-62-64 (e.g. H4H10429P); 68-70-72-76-78-80 (e.g. H4H10430P); 84-86-88-92-94-96 (e.g. H4H10432P2; 100-102-104-92-94-96 (e.g. H4H10433P2); 108-110-112-92-94-96 (e.g. H4H10436P2); 116-118-120-92-94-96 (e.g. H4H10437P2); 124-126-128-92-94-96 (e.g. H4H10438P2); 132-134-136-92-94-96 (e.g. H4H10440P2); 140-142-144-148-150-152 (e.g. H4H10442P2); 156-158-160-148-150-152 (H4H10445P2); 164-166-168-148-150-152 (H4H10446P2); 172-174-176-148-150-152 (H4H10447P2); 180-182-184-148-150-152 (H4H10448P2); 188-190-192-148-150-152 (H4H10452P2); 196-198-200-148-150-152 (H4H10468P2); and 204-206-208-212-214-216 (H2aM10965N).

In a related embodiment, the invention includes an antibody or antigen-binding fragment of an antibody which specifically binds Activin A, wherein the antibody or fragment comprises the heavy and light chain CDR domains contained within heavy and light chain variable region (HCVR/LCVR) sequences selected from the group consisting of SEQ ID NO: 2/10, 18/26, 34/42, 50/58, 66/74, 82/90, 98/90, 106/90, 114/90, 122/90, 130/90, 138/146, 154/146, 162/146, 170/146, 178/146, 186/146, 194/146, and 202/210. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., J Mol Biol 273:927-948 (1997); and Martin et al., PNAS (USA) 86:9268-9272 (1989). Public databases are also available for identifying CDR sequences within an antibody.

The present invention also provides nucleic acid molecules encoding anti-Activin A antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-Activin A antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-Activin A antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-Activin A antibody listed in Table 1.

The present invention also provides recombinant expression vectors capable of expressing a polypeptide comprising a heavy or light chain variable region of an anti-Activin A antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-Activin A antibodies having a modified carbohydrate content. In some applications, modification to remove undesirable glycosylation sites may be useful. In some applications, modification to alter glycosylation patterns may be useful, e.g., modifying an antibody to lack a fucose moiety present on an oligosaccharide chain, for example, to increase antibody dependent cellular cytotoxicity (ADCC) function (see Shield et al. J Biol Chem 277:26733 (2002)). In other applications, modification of galactosylation can be made in order to modify complement dependent cytotoxicity (CDC). In some applications, antibodies may have modified glycosylation patterns in order to minimize effector function. For example, antibodies may be modified to obtain additionally glycosylated or sialylated antibodies.

In another aspect, the invention provides a pharmaceutical composition comprising a recombinant human antibody or fragment thereof which specifically binds Activin A and a pharmaceutically acceptable carrier. In a related aspect, the invention features a composition which is a combination of an anti-Activin A antibody and a second therapeutic agent. In one embodiment, the second therapeutic agent is any agent that is advantageously combined with an anti-Activin A antibody. Exemplary agents that may be advantageously combined with an anti-Activin A antibody include, without limitation, other agents that inhibit Activin A activity (including other antibodies or antigen-binding fragments thereof, peptide inhibitors, small molecule antagonists, etc.) and/or agents which do not directly bind Activin A but nonetheless interfere with, block or attenuate Activin A-mediated signaling. In one embodiment, the secondary therapeutic agent inhibits, interferes, blocks and/or attenuates the activity of another ligand of the ActRIIA and/or ActRIIB receptor (e.g., GDF8, Activin B, Activin AB, Inhibin A, Inhibin B, GDF3, GDF11, Nodal, BMP2, BMP4, and/or BMP7). In one embodiment, the secondary therapeutic agent is an anti-GDF8 antagonist (e.g., a human anti-GDF8 antibody or antigen-binding fragment thereof). Exemplary anti-GDF8 agents for use with the anti-Activin A antibodies of the invention include a human anti-GDF8 antibody (e.g., an anti-GDF8 antibody comprising any of the HCVR/LCVR or CDR amino acid sequences as set forth in US 2011-0293630 A1 (e.g., H4H1657N2, which is an anti-GDF8 antibody with heavy chain complementarity determining regions (HCDRs) of a HCVR comprising SEQ ID NO:217 (e.g., the CDR1, CDR2, and CDR3 sequences set forth in SEQ ID NO:218, 219, and 220, respectively), and the light chain complementarity determining regions (LCDRs) of a LCVR comprising SEQ ID NO:221 (e.g., the CDR1, CDR2, and CDR3 sequences set forth in SEQ ID NO:222, 223, and 224)). Additional combination therapies and co-formulations involving the anti-Activin A antibodies of the present invention are disclosed elsewhere herein.

In an additional aspect of the invention, an antigen-binding molecule is provided comprising an Activin A-specific binding domain and a GDF8-specific binding domain. In one embodiment of this aspect of the invention, the antigen-binding molecule is a bispecific antibody comprising a first variable domain that specifically binds Activin A and a second variable domain that specifically binds GDF8.

In yet another aspect, the invention provides therapeutic methods for inhibiting Activin A activity using an anti- Activin A antibody or antigen-binding portion of an antibody of the invention, wherein the therapeutic methods comprise administering a therapeutically effective amount of a pharmaceutical composition comprising an antibody or antigen-binding fragment of an antibody of the invention. The disorder treated is any disease or condition which is improved, ameliorated, inhibited or prevented by removal, inhibition or reduction of Activin A activity or signaling. The anti-Activin A antibodies or antibody fragments of the invention may function to block the interaction between Activin A and an Activin Type II receptor (e.g., Activin Type IIA receptor and/or Activin Type IIB receptor); between Activin A and an Activin Type I receptor; between Activin A and both a Type II and a Type I receptor; or otherwise inhibit the signaling activity of Activin A.

The present invention also includes the use of an anti-Activin A antibody or antigen binding portion of an antibody of the invention in the manufacture of a medicament for the treatment of a disease or disorder related to or caused by Activin A activity in a patient. The present invention also provides methods for increasing muscle mass or strength in a subject by administering to the subject an Activin A antibody or antigen-binding fragment thereof. The present invention also provides methods for increasing muscle mass or strength in a subject by administering to the subject an Activin A-specific binding protein and a GDF8-specific binding protein, or by administering to the subject an antigen-binding molecule comprising an Activin A-specific binding domain and a GDF8-specific binding domain.

The invention also includes methods for treating, preventing and/or ameliorating a disease or disorder characterized by decreased muscle mass or strength by administering to a subject in need thereof an Activin A-specific binding protein (e.g., an anti-Activin A antibody). In a related aspect, methods of the invention include the treating, preventing and/or ameliorating a disease or disorder characterized by decreased muscle mass or strength by administering to a subject in need thereof an Activin A-specific binding protein and a GDF8-specific binding protein (e.g., an anti-Activin A antibody and an anti GDF8 antibody). Methods of the invention also include treating, preventing and/or ameliorating a disease or disorder characterized by decreased muscle mass or strength by administering to a subject in need thereof an antigen-binding molecule comprising an Activin A-specific binding domain and a GDF8-specific binding domain. Diseases or disorders characterized by decreased muscle mass or strength that can be treated, prevented and/or ameliorated using methods of the invention include sarcopenia, cachexia (e.g., idiopathic cachexia or cachexia secondary to another condition (e.g., cancer, chronic renal failure, or chronic obstructive pulmonary disease)), muscle injury, muscle wasting and/or atrophy (e.g., caused by or associated with disuse, immobilization, bed rest, injury, medical treatment, surgical intervention (e.g., hip fracture, hip replacement, and knee replacement) and by necessity of mechanical ventilation), cancer, obesity, diabetes, arthritis, multiple sclerosis, muscular dystrophy, amyotrophic lateral sclerosis, Parkinson's disease, osteoporosis, osteoarthritis, osteopenia, and metabolic syndromes (e.g., one or more of diabetes, obesity, nutritional disorders, organ atrophy, chronic obstructive pulmonary disease, and anorexia).

The invention also includes methods for treating, preventing and/or ameliorating diseases or disorders caused by, promoted by, exacerbated by, or aggravated by the activity of a molecule containing inhibin βA (e.g., dimers containing inhibin βA, e.g., Activin A, Activin AB, etc.) by administering to a subject in need thereof a binding protein specific for Activin A (i.e., inhibin βA dimer), e.g., an anti-Activin A antibody or antigen-binding fragment thereof. In one aspect of the invention, methods of the invention include methods of treating, preventing, and/or ameliorating renal fibrosis by administering to a subject in need thereof an anti-Activin A antibody. In particular aspects of the invention, methods of the invention include methods of treating, preventing, and/or ameliorating renal fibrosis caused by chronic kidney disease (e.g., as a consequence of hypertension, diabetes, glomerulonephritis, inherited diseases (such as polycystic kidney disease), malformations of the kidney, autoimmune disease (e.g., lupus), or obstructions (e.g., kidney stones, tumors, enlarged prostate gland), or repeated urinary infections) by administering to a subject in need thereof an anti-Activin A antibody. Additional aspects of the invention include methods of treating, preventing, and/or ameliorating sepsis, chronic heart failure, chronic obstructive pulmonary disease, benign or malignant pheochromocytoma, uterine fibroids/leiomyomata, preeclampsia, keloids, hypertrophic scars, or pulmonary artery hypertension by administering to a subject in need thereof an anti-Activin A antibody. Additional aspects of the invention include methods of treating, preventing, and/or ameliorating cachexia caused by, promoted by, exacerbated by, or aggravated by Activin A activity by administering to a subject in need thereof an anti-Activin A antibody. Additional aspects of the invention include methods of treating, preventing, and/or ameliorating weight loss caused by, promoted by, exacerbated by, or aggravated by Activin A activity by administering to a subject in need thereof an anti-Activin A antibody.

Other embodiments will become apparent from a review of the ensuing detailed description.

BRIEF DESCRIPTION OF THE FIGURES

FIG. 1 is a matrix showing the results of an antibody cross-competition assay in which a first anti-Activin A antibody ("Antibody Sample") was applied to an anti-human FC-coated sensor tip, followed by emersion in a solution of a second anti-Activin A antibody (1 µM) pre-bound to Activin A. Binding responses (numerical values 0.22 to 1.84) for each antibody combination tested are depicted. Binding responses presented in white boxes with black type indicate no competition for binding of Activin A, suggesting distinct binding regions.

DETAILED DESCRIPTION

Figure 2:
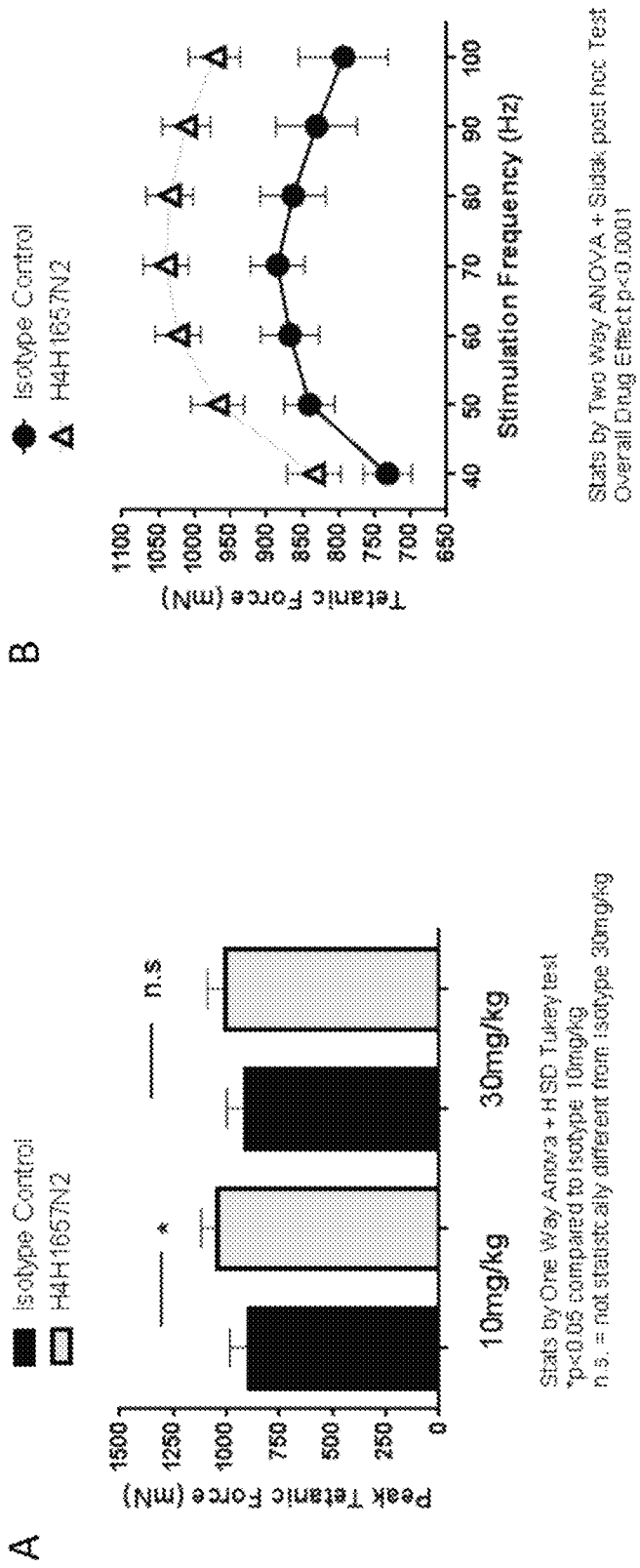
FIG. 2: Panel A shows the effects of 21 days of anti-GDF8 antibody treatment (H4H1657N2, 10 mg/kg or 30 mg/kg) on average peak tetanic force compared to isotype control antibody. Data analyzed using one-way analysis of variance (ANOVA) followed by Tukey's test. *p<0.05 significance over isotype control (n=6, unpaired Student t test); n.s.=not statistically significant compared to isotype 30 mg/kg. Panel B shows the increase in tibialis anterior (TA) muscle peak tetanic force in H4H1657N2-treated mice (10 mg/kg) versus mice treated with isotype control antibodies for three weeks (n=6), when stimulated by electric current over a range of frequencies (40 to 100 Hz). Data are expressed as mean average peak force±SEM.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Antigen-Specific Binding Proteins

The present invention relates to compositions comprising antigen-specific binding proteins. More specifically, the present invention provides a composition comprising an Activin A-specific binding protein.

As used herein, the expression "antigen-specific binding protein" means a protein comprising at least one domain which specifically binds a particular antigen. Exemplary categories of antigen-specific binding proteins include antibodies, antigen-binding portions of antibodies, peptides that specifically interact with a particular antigen (e.g., peptibodies), receptor molecules that specifically interact with a particular antigen, and proteins comprising a ligand-binding portion of a receptor that specifically binds a particular antigen.

The present invention includes antigen-specific binding proteins that specifically bind Activin A, i.e., "Activin A-specific binding proteins". Activins are homo- and heterodimeric molecules comprising beta subunits, i.e., Inhibin βA, inhibin βB, inhibin βC, and/or inhibin βE. The βA subunit has the amino acid sequence of SEQ ID NO:226 and the βB subunit has the amino acid sequence of SEQ ID NO:228. Activin A is a homodimer of two βA subunits; Activin B is a homodimer of two βB subunits; Activin AB is a heterodimer of one βA subunit and one βB subunit; and Activin AC is a heterodimer of one βA subunit and one βC subunit. An Activin A-specific binding protein may be an antigen-specific binding protein that specifically binds the βA subunit. Since the βA subunit is found in Activin A, Activin AB, and Activin AC molecules, an "Activin A-specific binding protein" can be an antigen-specific binding protein that specifically binds Activin A as well as Activin AB and Activin AC (by virtue of its interaction with the βA subunit). Therefore, according to one embodiment of the present invention, an Activin A-specific binding protein specifically binds Activin A; or Activin A and Activin AB; or Activin A and Activin AC; or Activin A, Activin AB and Activin AC, but does not bind other ActRIIB ligands such as Activin B, GDF3, GDF8, BMP2, BMP4, BMP7, BMP9, BMP10, GDF11, Nodal, etc. Thus, in one embodiment of the invention, an Activin A-specific binding protein specifically binds to Activin A but does not bind significantly to Activin B or Activin C. In another embodiment, an Activin A-specific binding protein may also bind to Activin B (by virtue of cross-reaction with the βB subunit, i.e., InhibinβB). In another embodiment, an Activin A-specific binding protein is a binding protein that binds specifically to Activin A but does not bind to any other ligand of ActRIIB. In another embodiment, an Activin A-specific binding protein is a binding protein and binds specifically to Activin A and does not bind to any Bone Morphogenetic Protein (BMP) (e.g., BMP2, BMP4, BMP6, BMP9, BMP10). In another embodiment, an Activin A-specific binding protein is a binding protein that binds specifically to Activin A but does not bind to any other member of the transforming growth factor beta (TGFβ) superfamily.

The present invention also includes antigen-specific binding proteins that specifically bind GDF8, i.e., "GDF8-specific binding proteins". The term "GDF8" (also referred to as "growth and differentiation factor-8" and "myostatin") means the protein having the amino acid sequence of SEQ ID NO:225 (mature protein). According to the present invention, GDF8-specific binding proteins specifically bind GDF8 but do not bind other ActRIIB ligands such as GDF3, BMP2, BMP4, BMP7, BMP9, BMP10, GDF11, Activin A, Activin B, Activin AB, Nodal, etc.

In the context of the present invention, molecules such as ActRIIB-Fc (e.g., "ACE-031"), which comprise the ligand-binding portion of the ActRIIB receptor, are not considered "Activin A-specific binding proteins" or "GDF8-specific binding proteins" because such molecules bind multiple ligands besides GDF8, Activin A and Activin AB.

All references to proteins, polypeptides and protein fragments herein are intended to refer to the human version of the respective protein, polypeptide or protein fragment unless explicitly specified as being from a non-human species.

Antigen-Binding Molecules with Two Different Antigen-Specific Binding Domains

The present invention also includes antigen-binding molecules comprising two different antigen-specific binding domains. In particular, the present invention includes antigen-binding molecules comprising an Activin A-specific binding domain and a GDF8-specific binding domain. The term "antigen-specific binding domain," as used herein, includes polypeptides comprising or consisting of: (i) an antigen-binding fragment of an antibody molecule, (ii) a peptide that specifically interacts with a particular antigen (e.g., a peptibody), and/or (iii) a ligand-binding portion of a receptor that specifically binds a particular antigen. For example, the present invention includes bispecific antibodies with one arm comprising a first heavy chain variable region/light chain variable region (HCVR/LCVR) pair that specifically binds Activin A and another arm comprising a second HCVR/LCVR pair that specifically binds GDF8.

Specific Binding

The term "specifically binds" or the like, as used herein, means that an antigen-specific binding protein, or an antigen-specific binding domain, forms a complex with a particular antigen characterized by a dissociation constant ($K_D$) of 500 pM or less, and does not bind other unrelated antigens under ordinary test conditions. "Unrelated antigens" are proteins, peptides or polypeptides that have less than 95% amino acid identity to one another. Methods for determining whether two molecules specifically bind one another are well known in the art and include, for example, equilibrium dialysis, surface plasmon resonance, and the like. For example, an antigen-specific binding protein or an antigen-specific binding domain, as used in the context of the present invention, includes molecules that bind a particular antigen (e.g., Activin A and/or AB, or GDF8) or a portion thereof with a $K_D$ of less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, less than about 10 pM, less than about 5 pM, less than about 4 pM, less than about 2 pM, less than about 1 pM, less than about 0.5 pM, less than about 0.2 pM, less than about 0.1 pM, or less than about 0.05 pM, as measured in a surface plasmon resonance assay.

As used herein, an antigen-specific binding protein or antigen-specific binding domain "does not bind" to a specified molecule (e.g., "does not bind GDF11", "does not bind BMP9", "does not bind BMP10", etc.) if the protein or binding domain, when tested for binding to the molecule at 25° C. in a surface plasmon resonance assay, exhibits a $K_D$ of greater than 50.0 nM, or fails to exhibit any binding in such an assay or equivalent thereof.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "$K_D$", as used herein, means the equilibrium dissociation constant of a particular protein-protein interaction (e.g., antibody-antigen interaction). Unless indicated otherwise, the $K_D$ values disclosed herein refer to $K_D$ values determined by surface plasmon resonance assay at 25° C.

Antibodies and Antigen-Binding Fragments of Antibodies

As indicated above, an antigen-specific binding protein can comprise or consist of an antibody or antigen-binding fragment of an antibody. Furthermore, in the case of antigen-binding molecules comprising two different antigen-specific binding domains, one or both of the antigen-specific binding domains may comprise or consist of an antigen-binding fragment of an antibody.

As used herein, "an antibody that binds Activin" or an "anti-Activin A antibody" includes antibodies, and antigen-binding fragments thereof, that bind a soluble fragment of the Activin A protein and may also bind to an Activin βA subunit-containing Activin heterodimer.

The term "antibody", as used herein, means any antigen-binding molecule or molecular complex comprising at least one complementarity determining region (CDR) that specifically binds to or interacts with a particular antigen (e.g., Activin A). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-Activin A antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (V) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al., PNAS USA 95:652-656 (1998)). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-Activin A antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al., Nucl Acids Res 20:6287-6295 (1992)) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. Molecular Immunology 30:105 1993)) to levels typically observed using a human IgG1 hinge. The instant invention encompasses antibodies having one or more mutations in the hinge, $C_H$2 or $C_H$3 region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The present invention includes neutralizing and/or blocking anti-Activin A antibodies. A "neutralizing" or "blocking" antibody, as used herein, is intended to refer to an antibody whose binding to Activin A: (i) interferes with the interaction between Activin A and an Activin A receptor (e.g., Activin Type IIA receptor, Activin Type IIB receptor, Activin Type I receptor, etc.); (ii) interferes with the formation of Activin-Activin receptor complexes; and/or (iii) results in inhibition of at least one biological function of Activin A. The inhibition caused by an Activin A neutralizing or blocking antibody need not be complete so long as it is detectable using an appropriate assay. Exemplary assays for detecting Activin A inhibition are described in the working Examples herein.

The anti-Activin A antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-Activin A antibodies comprising variants of any of the HCVR, LCVR, and/or CDR amino acid sequences disclosed herein having one or more conservative substitutions. For example, the present invention includes anti-Activin A antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson, W. R., Methods Mol Biol 24: 307-331 (1994), herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine;

(6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al., Science 256: 1443-1445 (1992), herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (see, e.g., Pearson, W. R., Methods Mol Biol 132: 185-219 (2000), herein incorporated by reference). Another preferred algorithm when comparing a sequence of the invention to a database containing a large number of sequences from different organisms is the computer program BLAST, especially BLASTP or TBLASTN, using default parameters. See, e.g., Altschul et al., J Mol Biol 215:403-410 (1990) and Altschul et al., Nucleic Acids Res 25:3389-402 (1997), each herein incorporated by reference.

Biological Characteristics of the Antibodies

The present invention includes anti-Activin A antibodies and antigen-binding fragments thereof that bind Activin A with high affinity. For example, the present invention includes antibodies and antigen-binding fragments of antibodies that bind Activin A (e.g., at 25° C. or 37° C.) with a $K_D$ of less than about 30 nM as measured by surface plasmon resonance, e.g., using the assay format as defined in Example 3 herein. In certain embodiments, the antibodies or antigen-binding fragments of the present invention bind Activin A with a $K_D$ of less than about 25 nM, less than about 20 nM, less than about 15 nM, less than about 10 nM, less than about 5 nM, less than about 2 nM, less than about 1 nM, less than about 500 pM, less than about 250 pM, less than about 240 pM, less than about 230 pM, less than about 220 pM, less than about 210 pM, less than about 200 pM, less than about 190 pM, less than about 180 pM, less than about 170 pM, less than about 160 pM, less than about 150 pM, less than about 140 pM, less than about 130 pM, less than about 120 pM, less than about 110 pM, less than about 100 pM, less than about 95 pM, less than about 90 pM, less than about 85 pM, less than about 80 pM, less than about 75 pM, less than about 70 pM, less than about 65 pM, less than about 60 pM, less than about 55 pM, less than about 50 pM, less than about 45 pM, less than about 40 pM, less than about 35 pM, less than about 30 pM, less than about 25 pM, less than about 20 pM, less than about 15 pM, less than about 10 pM, less than about 9 pM, less than about 8 pM, less than about 7 pM, less than about 6 pM, less than about 5 pM, less than about 4 pM, or less than about 3 pM, as measured by surface plasmon resonance, e.g., using the assay format as defined in Example 3 herein, or a substantially similar assay.

The present invention also includes anti-Activin A antibodies and antigen-binding fragments thereof that inhibit Activin A-mediated cellular signaling. For example, the present invention includes anti-Activin A antibodies that inhibit the activation of the SMAD complex signal transduction pathway via the binding of Activin A to Activin Type I or II receptors with an $IC_{50}$ value of less than about 4 nM, as measured in a cell-based blocking bioassay, e.g., using the assay format as defined in Example 6 herein, or a substantially similar assay. In certain embodiments, the antibodies or antigen-binding fragments of the present invention inhibit the activation of the SMAD complex signal transduction pathway via the binding of Activin A to Activin Type I or II receptors with an $IC_{50}$ value of less than about 3 nM, less than about 2 nM, less than about 1 nm, less than about 500 pM, less than about 250 pM, less than about 240 pM, less than about 230 pM, less than about 220 pM, less than about 210 pM, less than about 200 pM, less than about 190 pM, less than about 180 pM, less than about 170 pM, less than about 160 pM, less than about 150 pM, less than about 140 pM, less than about 130 pM, less than about 120 pM, less than about 110 pM, less than about 100 pM, less than about 95 pM, less than about 90 pM, less than about 85 pM, less than about 80 pM, less than about 75 pM, less than 70 pM, less than about 65 pM, less than about 60 pM, less than about 55 pM, less than about 50 pM, less than about 49 pM, less than about 48 pM, less than about 47 pM, less than about 46 pM, less than about 45 pM, less than about 44 pM, less than about 43 pM, less than about 42 pM, less than about 41 pM, less than about 40 pM, or less than about 39 pM, as measured in a cell-based blocking bioassay, e.g., using the assay format as defined in Example 6 herein, or a substantially similar assay. In certain embodiments, the antibodies or antigen-binding fragments of the present invention inhibit the signaling activing of Activin B by interfering with the binding of Activin B to Activin Type I or II receptors with an $IC_{50}$ value of less than about 50 nM, less than about 20 nM, less than about 10 nm, less than about 5 nM, or less than about 1 nM, as measured in a cell-based blocking bioassay, e.g., using the assay format as defined in Example 6 herein, or a substantially similar assay. In certain embodiments, the antibodies or antigen-binding fragments of the present invention inhibit the activation of the SMAD complex signal transduction pathway via the binding of Activin AB to Activin Type I or II receptors with an $IC_{50}$ value of less than about 500 pM, less than about 450 pM, less than about 440 pM, less than about 430 pM, less than about 420 pM, less than about 410 pM, less than about 400 pM, less than about 390 pM, less than about 380 pM, less than about 370 pM, less than about 360 pM, less than about 350 pM, less than about 340 pM, less than about 320 pM, less than about 310 pM, less than about 300 pM, less than about 290 pM, less than about 280 pM, less than about 270 pM, less than about 260 pM, less than about 250 pM, less than about 240 pM, less than about 230 pM, less than about 220 pM, less than about 210 pM, less than about 200 pM, less than about 190 pM, less than about 180 pM, less than about 170 pM, less than about 160 pM, less than about 150 pM, or less than about 140 pM, as measured in a cell-based blocking bioassay, e.g., using the assay format as defined in Example 6 herein, or a substantially similar assay. In certain embodiments, the antibodies or antigen-binding fragments of the present invention inhibit the activation of the SMAD complex signal transduction pathway via the binding of Activin AC to Activin Type I or II receptors with an $IC_{50}$ value of less than about 1 nM, less than about 900 pM, less than about 800 pM, less than about 750 pM, less than about 700 pM, less than about 650 pM, less than about 600 pM, or less than about 580 pM, as measured in a cell-based blocking bioassay, e.g., using the assay format as defined in Example 6 herein, or a substantially similar assay.

The antibodies of the present invention may possess one or more of the aforementioned biological characteristics, or any combinations thereof. Other biological characteristics of the antibodies of the present invention will be evident to a person of ordinary skill in the art from a review of the present disclosure including the working Examples herein.

Anti-Activin A Antibodies Comprising Fc Variants

According to certain embodiments of the present invention, anti-Activin A antibodies are provided comprising an Fc domain comprising one or more mutations which enhance or diminish antibody binding to the FcRn receptor, e.g., at acidic pH as compared to neutral pH. For example, the present invention includes anti-Activin A antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-Activin A antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations, and other mutations within the antibody variable domains disclosed herein, are contemplated within the scope of the present invention.

The present invention also includes anti-Activin A antibodies comprising a chimeric heavy chain constant (CH) region, wherein the chimeric CH region comprises segments derived from the CH regions of more than one immunoglobulin isotype. For example, the antibodies of the invention may comprise a chimeric CH region comprising part or all of a CH2 domain derived from a human IgG1, human IgG2 or human IgG4 molecule, combined with part or all of a CH3 domain derived from a human IgG1, human IgG2 or human IgG4 molecule. According to certain embodiments, the antibodies of the invention comprise a chimeric CH region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric CH region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Epitope Mapping and Related Technologies

The present invention includes anti-Activin A antibodies which interact with one or more amino acids found within Activin A (e.g., within the Activin Type II receptor binding site). The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the Activin βA subunit. Alternatively, the epitope may consist of a plurality of non-contiguous amino acids (or amino acid sequences) located within the Activin A dimer.

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide blots analysis (Reineke, Methods Mol Biol 248:443-463 (2004)), and peptide cleavage analysis. In addition, methods such as epitope excision, epitope extraction and chemical modification of antigens can be employed (Tomer, Protein Science 9:487-496 (2000)). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring, Analytical Biochemistry 267(2):252-259 (1999); Engen and Smith, Anal. Chem. 73:256 A-265A (2001).

The present invention further includes anti-Activin A antibodies that bind to the same epitope as any of the specific exemplary antibodies described herein (e.g., H4H10423P, H4H10424P, H4H10426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10448P2, H4H10452P2, H4H10468P2, H2aM10965N, etc.). Likewise, the present invention also includes anti-Activin A antibodies that compete for binding to Activin A with any of the specific exemplary antibodies described herein (e.g., H4H10423P, H4H10424P, H4H10426P, H4H10429P, H4H10430P, H4H10432P2, H4H10433P2, H4H10436P2, H4H10437P2, H4H10438P2, H4H10440P2, H4H10442P2, H4H10445P2, H4H10446P2, H4H10447P2, H4H10448P2, H4H10452P2, H4H10468P2, H2aM10965N, etc.). For example, the present invention includes anti-Activin A antibodies that cross-compete for binding to Activin A with one or more antibodies of "Bin 1" as defined in Example 4 herein (e.g., H4H10423P, H4H10446P2, H4H10468P2 and H4H10442P2). The present invention also includes anti-Activin A antibodies that cross-compete for binding to Activin A with one or more antibodies of "Bin 2" as defined in Example 4 herein (e.g., H4H10429, H4H1430P, H4H10432P2, H4H10436P2, and H4H10440P2).

One can easily determine whether an antibody binds to the same epitope as, or competes for binding with, a reference anti-Activin A antibody by using routine methods known in the art and exemplified herein. For example, to determine if a test antibody binds to the same epitope as a reference anti-Activin A antibody of the invention, the reference antibody is allowed to bind to Activin A (or a βA subunit-containing heterodimer). Next, the ability of a test antibody to bind to Activin A is assessed. If the test antibody is able to bind to Activin A following saturation binding with the reference anti-Activin A antibody, it can be concluded that the test antibody binds to a different epitope than the reference anti-Activin A antibody. On the other hand, if the test antibody is not able to bind to Activin A following saturation binding with the reference anti-Activin A antibody, then the test antibody may bind to the same epitope as the epitope bound by the reference anti-Activin A antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 50:1495-1502 (1990)). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-Activin A antibody, the above-described binding methodology is performed in two orientations: In a first orientation, the reference antibody is allowed to bind to Activin A protein (or a βA subunit-containing heterodimer) under saturating conditions followed by assessment of binding of the test antibody to the Activin A molecule. In a second orientation, the test antibody is allowed to bind to Activin A under saturating conditions followed by assessment of binding of the reference antibody to Activin A. If, in both orientations, only the first (saturating) antibody is capable of binding to Activin A, then it is concluded that the test antibody and the reference antibody compete for binding to Activin A (see, e.g., the assay format described in Example 4 herein, in which a test Activin A antibody is captured onto sensor tips that are then submerged in a solution containing a reference Activin A antibody pre-bound with Activin A). As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Anti-Activin A antibodies of the invention may bind to an epitope on Activin A that is within or near the binding site for an Activin Type II receptor, directly block interaction between Activin A and an Activin Type II receptor, and indirectly block interaction between Activin A and an Activin Type I receptor. Anti-Activin A antibodies of the invention may bind to an epitope on Activin A that is within or near the binding site for the Activin Type I receptor and directly block interaction between Activin A and an Activin Type I receptor. In one embodiment of the invention, an anti-Activin A antibody of the invention that binds to Activin A at or near the Activin Type I receptor binding site does not block interaction between Activin A and an Activin A Type II receptor.

Preparation of Human Antibodies

Methods for generating monoclonal antibodies, including fully human monoclonal antibodies are known in the art. Any such known methods can be used in the context of the present invention to make human antibodies that specifically bind to human Activin A.

Using VELOCIMMUNE™ technology, for example, or any other known method for generating fully human monoclonal antibodies, high affinity chimeric antibodies to human Activin A are initially isolated having a human variable region and a mouse constant region. As in the experimental section below, the antibodies are characterized and selected for desirable characteristics, including affinity, selectivity, epitope, etc. If necessary, mouse constant regions are replaced with a desired human constant region, for example wild-type or modified IgG1 or IgG4, to generate a fully human anti-Activin A antibody. While the constant region selected may vary according to specific use, high affinity antigen-binding and target specificity characteristics reside in the variable region. In certain instances, fully human anti-Activin A antibodies are isolated directly from antigen-positive B cells.

Bioequivalents

The anti-Activin A antibodies and antibody fragments of the present invention encompass proteins having amino acid sequences that vary from those of the described antibodies but that retain the ability to bind human Activin A. Such variant antibodies and antibody fragments comprise one or more additions, deletions, or substitutions of amino acids when compared to parent sequence, but exhibit biological activity that is essentially equivalent to that of the described antibodies. Likewise, the anti-Activin A antibody-encoding DNA sequences of the present invention encompass sequences that comprise one or more additions, deletions, or substitutions of nucleotides when compared to the disclosed sequence, but that encode an anti-Activin A antibody or antibody fragment that is essentially bioequivalent to an anti-Activin A antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-Activin A antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include anti-Activin A antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-Activin A antibodies that bind to human Activin A but not to Activin A from other species. The present invention also includes anti-Activin A antibodies that bind to human Activin A and to Activin A from one or more non-human species. For example, the anti-Activin A antibodies of the invention may bind to human Activin A and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee Activin A. According to certain exemplary embodiments of the present invention, anti-Activin A antibodies are provided which specifically bind human Activin A (e.g., Activin A or a βA subunit-containing heterodimer) and cynomolgus monkey (e.g., *Macaca fascicularis*) Activin A.

Immunoconjugates

The invention encompasses anti-Activin A monoclonal antibodies conjugated to a therapeutic moiety ("immunoconjugate"), such as a cytotoxin, a chemotherapeutic drug, an immunosuppressant or a radioisotope. Cytotoxic agents include any agent that is detrimental to cells. Examples of suitable cytotoxic agents and chemotherapeutic agents for forming immunoconjugates are known in the art (see for example, WO 05/103081).

Multispecific Antibodies

The antibodies of the present invention may be monospecific, bi-specific, or multispecific. Multispecific antibodies may be specific for different epitopes of one target polypeptide or may contain antigen-binding domains specific for more than one target polypeptide. See, e.g., Tutt et al., J Immunol 147:60-69 (1991); Kufer et al., Trends Biotechnol 22:238-244 (2004). The anti-Activin A antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity. For example, the present invention includes bi-specific antibodies wherein one arm of an immunoglobulin is specific for human Activin A or a fragment thereof, and the other arm of the immunoglobulin is specific for a second therapeutic target or is conjugated to a therapeutic moiety. One embodiment of the invention includes bi-specific antibodies wherein one arm of an immunoglobulin is specific for human Activin A or a fragment thereof, and the other arm of the immunoglobulin is specific for GDF8.

An exemplary bi-specific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference (see, e.g., U.S. Pat. No. 8,586,713, incorporated by reference herein in its entirety). In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, V82I, and L105P (by IMGT; Q355R, N384S, K392N, V397M, R409K, E419Q, V422I, and L445P by EU) in the case of IgG4 antibodies. Variations on the bi-specific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mab$^2$ bispecific formats (see, e.g., Klein et al., mAbs 4:6, 1-11 (2012), and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., J Am Chem Soc. 135(1):340-346 (2013)).

Therapeutic Formulation and Administration

The invention provides pharmaceutical compositions comprising the anti-Activin A antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA, J Pharm Sci Technol 52:238-311 (1998).

The dose of antibody administered to a patient may vary depending upon the age and the size of the patient, target disease, conditions, route of administration, and the like. The preferred dose is typically calculated according to body weight or body surface area. When an antibody of the present invention is used for treating a condition or disease associated with Activin A activity in an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-Activin A antibodies may be determined empirically; for example, patient progress can be monitored by periodic assessment, and the dose adjusted accordingly. Moreover, interspecies scaling of dosages can be performed using well-known methods in the art (e.g., Mordenti et al., Pharmaceut Res 8:1351 (1991)).

Various delivery systems are known and can be used to administer the pharmaceutical composition of the invention, e.g., encapsulation in liposomes, microparticles, microcapsules, recombinant cells capable of expressing an antibody or other therapeutic protein of the invention, receptor mediated endocytosis (see, e.g., Wu et al., J Biol Chem 262:4429-4432 (1987)). The antibodies and other therapeutically active components of the present invention may also be delivered by gene therapy techniques. Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, CRC Crit. Ref. Biomed. Eng. 14:201 (1987)). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, Science 249:1527-1533 (1990).

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The antibodies of the invention are useful, inter alia, for the treatment, prevention and/or amelioration of any disease or disorder associated with or mediated by Activin A expression, signaling, or activity, or treatable by blocking the interaction between Activin A and an Activin A receptor (e.g., ActRIIA, ActRIIB, Activin Type I receptor, etc.) or otherwise inhibiting Activin A activity and/or signaling. For example, the present invention provides methods of treating conditions or afflictions which can be cured, alleviated or improved by increasing muscle strength/power and/or muscle mass and/or muscle function in an individual, or by favorably altering metabolism (carbohydrate, lipid and protein processing) by specifically binding Activin A and not binding other ActRIIB ligands, or by specifically binding Activin A and GDF8 and not binding other ActRIIB ligands. For example, the present invention includes methods for increasing muscle strength/power and/or muscle mass and/or muscle function in a subject, or for treating a disease or disorder characterized by decreased muscle mass or strength in a subject, by administering to the subject an Activin A-specific binding protein. The present invention also includes methods for increasing muscle strength/power and/or muscle mass and/or muscle function in a subject, or for treating a disease or disorder characterized by decreased muscle mass or strength in a subject, by administering to the subject an Activin A-specific binding protein and a GDF8-specific binding protein. Any of the Activin A-specific binding proteins and/or GDF8-specific binding proteins disclosed or referred to herein can be used in the context of these aspects of the invention. For example, the therapeutic methods of the present invention include administering to a subject an anti-Activin A antibody and/or an anti-GDF8 antibody.

Thus, in the context of the methods of treatment described herein, the anti-Activin A antibody may be administered as a monotherapy (i.e., as the only therapeutic agent) or in combination with one or more additional therapeutic agents (e.g., an anti-GDF8 antibody), further examples of which are described elsewhere herein.

In methods which comprise administering an Activin A-specific binding protein and a GDF8-specific binding protein to a subject, the Activin A-specific binding protein and the GDF8-specific binding protein may be administered to the subject at the same or substantially the same time, e.g., in a single therapeutic dosage, or in two separate dosages which are administered simultaneously or within less than about 5 minutes of one another. Alternatively, the Activin A-specific binding protein and the GDF8-specific binding protein may be administered to the subject sequentially, e.g., in separate therapeutic dosages separated in time from one another by more than about 5 minutes.

The present invention also includes methods for increasing muscle strength/power and/or muscle mass and/or muscle function in a subject, or for treating a disease or disorder characterized by decreased muscle mass or strength in a subject, by administering to the subject an antigen-binding molecule comprising an Activin A-specific binding domain and a GDF8-specific binding domain. Any of the antigen-binding molecules disclosed or referred to herein can be used in the context of this aspect of the invention. For example, the therapeutic methods of the present invention include administering to a subject a bispecific antibody comprising a first variable domain comprising a HCVR/LCVR pair that specifically binds Activin A and a second variable domain comprising a HCVR/LCVR pair that specifically binds GDF8.

The compositions of the present invention may be administered to a subject along with one or more additional therapeutic agents, including, e.g., growth factor inhibitors, immunosuppressants, anti-inflammatory agents, metabolic inhibitors, enzyme inhibitors, and cytotoxic/cytostatic agents. The additional therapeutic agent(s) may be administered prior to, concurrent with, or after the administration of the Activin A- and GDF8-specific binding proteins of the present invention.

Exemplary diseases, disorders and conditions that can be treated with the compositions of the present invention include, but are not limited to, sarcopenia, cachexia (either idiopathic or secondary to other conditions, e.g., cancer, chronic renal failure, or chronic obstructive pulmonary disease), muscle injury, muscle trauma, muscle wasting and muscle atrophy, e.g., muscle atrophy or wasting caused by or associated with disuse, e.g., muscular, immobilization, bed rest, injury, medical treatment or surgical intervention (e.g., hip fracture, hip replacement, knee replacement, and other joint, tendon, or ligament injuries such as tears in the anterior cruciate ligament (ACL) and/or the medial collateral ligament (MCL), etc.), muscular dystrophy (e.g., Myotonic, Duchenne, Becker, Limb-girdle, Facioscapulohumeral (FSHD, also known as Landouzy-Déjérine disease), Congenital, Oculopharyngeal, Distal, Emery-Dreifuss, etc.), glucocorticoid-induced myopathy, stroke rehabilitation (e.g., rehabilitation for stroke hemiparesis) or by necessity of mechanical ventilation. The compositions of the invention may also be used to treat, prevent or ameliorate diseases such as cancer, obesity, diabetes, arthritis, multiple sclerosis, muscular dystrophy, amyotrophic lateral sclerosis, Parkinson's disease, osteoporosis, osteoarthritis, osteopenia, and metabolic syndromes (including, but not limited to diabetes, obesity, nutritional disorders, organ atrophy, chronic obstructive pulmonary disease, and anorexia). Additional diseases, disorders, and conditions that can be prevented, treated and/or ameliorated using compositions of the present invention include sepsis, chronic heart failure, benign and malignant pheochromocytoma, uterine fibroids/leiomyomata, preeclampsia, keloids and hypertrophic scars, and pulmonary artery hypertension.

Improved Specificity of Binding and Activity

The present invention includes methods for increasing muscle strength/power and/or muscle mass and/or muscle function in a subject, or for treating a disease or disorder characterized by decreased muscle mass or strength in a subject, or for treating a disease or disorder caused by, promoted by, or aggravated by Activin A activity, without causing adverse effects associated with the administration of molecules which bind multiple (e.g., 3 or more) ActRIIB ligands. In other words, methods using anti-Activin A antibodies or antigen binding proteins thereof (e.g., wherein the anti-Activin A antibody only significantly binds to Activin A) may treat a disease or disorder without causing unwanted or adverse effects seen with molecules which bind multiple ActRIIB ligands. For example, the clinical molecule referred to as ACE-031 (Acceleron Pharma, Inc., Cambridge, Mass.) is a multimer consisting of the extracellular portion of ActRIIB fused to an IgG Fc domain (this molecule is also referred to herein as "ActRIIB-Fc"). ActRIIB-Fc binds Activin A as well as other ActRIIB ligands such as, e.g., Activin B, GDF8, GDF11, BMP9, BMP10, and TGFβ, and is known to cause various adverse effects when administered to human patients. Significantly, the present inventors have unexpectedly discovered that specifically inhibiting Activin A and GDF8 (e.g., by administering an anti-Activin A antibody and an anti-GDF8 antibody), while not inhibiting other ActRIIB ligands such as Activin B, GDF11, BMP9, BMP10, and TGFβ, results in an increase in muscle mass that is at least equivalent to that observed by administration of ActRIIB-Fc, without causing the adverse effects associated with binding agents such as ActRIIB-Fc.

Combination Therapies and Formulations

The present invention includes compositions and therapeutic formulations comprising any of the anti-Activin A antibodies described herein in combination with one or more additional therapeutically active components, and methods of treatment comprising administering such combinations to subjects in need thereof. The present invention also includes compositions and therapeutic formulations comprising any of the anti-Activin A antibodies described herein in combination with one or more additional therapeutically active components, and methods of treatment comprising administering such combinations to subjects in need thereof. For example, the anti-Activin A antibodies of the invention may also be administered and/or co-formulated in combination with antivirals, antibiotics, analgesics, corticosteroids, steroids, oxygen, antioxidants, metal chelators, IFN-gamma, and/or NSAIDs. The anti-Activin A antibodies of the invention may also be administered as part of a treatment regimen that also includes radiation treatment and/or conventional chemotherapy (e.g., in the context of methods of treating cancer or inhibiting tumor growth). Any of the aforementioned additional therapeutically active components may be administered in combination with any of the anti-Activin A antibodies of the present invention for the treatment of any disease or disorder in which administration of an anti-Activin A antibody is beneficial, including, e.g., sarcopenia, cachexia, muscle injury, muscle wasting and muscle atrophy. Any of the aforementioned additional therapeutically active components may also be administered in combination with any of the anti-Activin A antibodies of the present invention along with a GDF8 inhibitor (e.g., an anti-GDF8 antibody).

The additional therapeutically active component(s) may be administered to a subject prior to administration of an anti-Activin A antibody of the present invention. For example, a first component may be deemed to be administered "prior to" a second component if the first component is administered 1 week before, 72 hours before, 60 hours before, 48 hours before, 36 hours before, 24 hours before, 12 hours before, 6 hours before, 5 hours before, 4 hours before, 3 hours before, 2 hours before, 1 hour before, 30 minutes before, 15 minutes before, 10 minutes before, 5 minutes before, or less than 1 minute before administration of the second component. In other embodiments, the additional therapeutically active component(s) may be administered to a subject after administration of an anti-Activin A antibody of the present invention. For example, a first component may be deemed to be administered "after" a second component if the first component is administered 1 minute after, 5 minutes after, 10 minutes after, 15 minutes after, 30 minutes after, 1 hour after, 2 hours after, 3 hours after, 4 hours after, 5 hours after, 6 hours after, 12 hours after, 24 hours after, 36 hours after, 48 hours after, 60 hours after, 72 hours after administration of the second component. In yet other embodiments, the additional therapeutically active component(s) may be administered to a subject concurrent with administration of anti-Activin A antibody of the present invention. "Concurrent" administration, for purposes of the present invention, includes, e.g., administration of an anti-Activin A antibody and an additional therapeutically active component to a subject in a single dosage form, or in separate dosage forms administered to the subject within about 30 minutes or less of each other. If administered in separate dosage forms, each dosage form may be administered via the same route (e.g., both the anti-Activin A antibody and the additional therapeutically active component may be administered intravenously, subcutaneously, intravitreally, etc.); alternatively, each dosage form may be administered via a different route (e.g., the anti-Activin A antibody may be administered locally (e.g., intravitreally) and the additional therapeutically active component may be administered systemically). In any event, administering the components in a single dosage from, in separate dosage forms by the same route, or in separate dosage forms by different routes are all considered "concurrent administration," for purposes of the present disclosure. For purposes of the present disclosure, administration of an anti-Activin A antibody "prior to", "concurrent with," or "after" (as those terms are defined herein above) administration of an additional therapeutically active component is considered administration of an anti-Activin A antibody "in combination with" an additional therapeutically active component).

The present invention includes pharmaceutical compositions in which an anti-Activin A antibody of the present invention is co-formulated with one or more of the additional therapeutically active component(s) as described elsewhere herein.

Dosage

The amount of active ingredient (e.g., anti-Activin A antibodies, anti-GDF8 antibodies given in combination with anti-Activin A antibodies, or bispecific antibodies that specifically bind Activin A and GDF8) that can be administered to a subject is, generally, a therapeutically effective amount. As used herein, the phrase "therapeutically effective amount" means a dose of antigen-specific binding proteins and/or antigen-binding molecules that results in a detectable increase in one or more of the following parameters: body weight, muscle mass (e.g., tibialis anterior [TA] muscle mass, gastrocnemius [GA] muscle mass, quadriceps [Quad] muscle mass, etc.), muscle strength/power, and/or muscle function. For example, a "therapeutically effective amount" of an Activin A-specific binding protein and/or a GDF8-specific binding protein includes, e.g., an amount of Activin A-specific binding protein and/or GDF8-specific binding protein that, when administered to a test subject, causes an increase in TA or GA muscle mass of at least 2%, 5%, 10%, 15%, 20%, 25%, 30%, 40%, 50%, 60% or more, compared to control treated subjects, e.g., as illustrated in Example 7, herein.

In the case of antibodies of the present invention (e.g., anti-Activin A antibodies, anti-GDF8 antibodies given in combination with anti-Activin A antibodies, or bispecific antibodies that specifically bind Activin A and GDF8), a therapeutically effective amount can be from about 0.05 mg to about 600 mg; e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, about 700 mg, about 710 mg, about 720 mg, about 730 mg, about 740 mg, about 750 mg, about 760 mg, about 770 mg, about 780 mg, about 790 mg, about 800 mg, about 810 mg, about 820 mg, about 830 mg, about 840 mg, about 850 mg, about 860 mg, about 870 mg, about 880 mg, about 890 mg, about 900 mg, about 910 mg, about 920 mg, about 930 mg, about 940 mg, about 950 mg, about 960 mg, about 970 mg, about 980 mg, about 990 mg, or about 1000 mg, of the respective antibody.

The amount of antibody of the present invention (e.g., anti-Activin A antibodies, anti-GDF8 antibodies given in combination with anti-Activin A antibodies, or bispecific antibodies that specifically bind Activin A and GDF8) contained within the individual doses may be expressed in terms of milligrams of antibody per kilogram of patient body weight (i.e., mg/kg). For example, the anti-Activin A, anti-GDF8 and/or anti-Activin A/anti-GDF8 bispecific antibodies of the present invention may be administered to a patient at a dose of about 0.0001 to about 50 mg/kg of patient body weight (e.g. 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, 10.0 mg/kg, 10.5 mg/kg, 11.0 mg/kg, 11.5 mg/kg, 12.0 mg/kg, 12.5 mg/kg, 13.0 mg/kg, 13.5 mg/kg, 14.0 mg/kg, 14.5 mg/kg, 15.0 mg/kg, 15.5 mg/kg, 16.0 mg/kg, 16.5 mg/kg, 17.0 mg/kg, 17.5 mg/kg, 18.0 mg/kg, 18.5 mg/kg, 19.0 mg/kg, 19.5 mg/kg, 20.0 mg/kg, etc.).

The compositions of the present invention may comprise equal amounts of Activin A-specific binding protein and GDF8-specific binding protein. Alternatively, the amount of Activin A-specific binding protein in the composition may be less than or greater than the amount of GDF8-specific binding protein. A person of ordinary skill in the art, using routine experimentation, will be able to determine the appropriate amounts of the individual components in the compositions of the present invention necessary to produce a desired therapeutic effect.

Administration Regimens

According to certain embodiments of the present invention, multiple doses of an active ingredient (e.g., an anti-Activin A antibody, an anti-GDF8 antibody administered in combination with an anti-Activin A antibody, a pharmaceutical composition comprising a combination of anti-Activin A antibody and any of the additional therapeutically active agents mentioned herein, including, e.g., an anti-GDF8 antibody, or a bispecific antibody that specifically bind Activin A and GDF8) may be administered to a subject over a defined time course. The methods according to this aspect of the invention comprise sequentially administering to a subject multiple doses of an active ingredient of the invention. As used herein, "sequentially administering" means that each dose of an active ingredient is administered to the subject at a different point in time, e.g., on different days separated by a predetermined interval (e.g., hours, days, weeks or months). The present invention includes methods which comprise sequentially administering to the patient a single initial dose of an active ingredient, followed by one or more secondary doses of the active ingredient, and optionally followed by one or more tertiary doses of the active ingredient.

The terms "initial dose," "secondary doses," and "tertiary doses," refer to the temporal sequence of administration of the active ingredient, e.g., anti-Activin A antibody of the invention or of a combination therapy of the invention, e.g., an anti-Activin A antibody and an anti-GDF8 antibody. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the active ingredient, e.g., anti-Activin A antibody, but generally may differ from one another in terms of frequency of administration. In certain embodiments, however, the amount of the active ingredient, e.g., anti-Activin A antibody, contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of the active ingredient, e.g., an anti-Activin A antibody, which is administered to a patient prior to the administration of the very next dose in the sequence with no intervening doses.

The methods according to this aspect of the invention may comprise administering to a patient any number of secondary and/or tertiary doses of an active ingredient of the invention, e.g., an anti-Activin A antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.).

Diagnostic Uses of the Antibodies

The anti-Activin A antibodies of the present invention may also be used to detect and/or measure Activin A, or Activin A-expressing cells in a sample, e.g., for diagnostic purposes. For example, an anti-Activin A antibody, or fragment thereof, may be used to diagnose a condition or disease characterized by aberrant expression (e.g., over-expression, under-expression, lack of expression, etc.) of Activin A. Exemplary diagnostic assays for Activin A may comprise, e.g., contacting a sample, obtained from a patient, with an anti-Activin A antibody of the invention, wherein the anti-Activin A antibody is labeled with a detectable label or reporter molecule. Alternatively, an unlabeled anti-Activin A antibody can be used in diagnostic applications in combination with a secondary antibody which is itself detectably labeled. The detectable label or reporter molecule can be a radioisotope, such as $^{3}H$, $^{14}C$, $^{32}P$, $^{35}S$, or $^{125}I$; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure Activin A in a sample include enzyme-linked immunosorbent assay (ELISA), radioimmunoassay (RIA), and fluorescence-activated cell sorting (FACS).

Samples that can be used in Activin A diagnostic assays according to the present invention include any tissue or fluid sample obtainable from a patient which contains detectable quantities of Activin A protein, or fragments thereof, under normal or pathological conditions. Generally, levels of Activin A in a particular sample obtained from a healthy patient (e.g., a patient not afflicted with a disease or condition associated with abnormal Activin A levels or activity) will be measured to initially establish a baseline, or standard, level of Activin A. This baseline level of Activin A can then be compared against the levels of Activin A measured in samples obtained from individuals suspected of having an Activin A-related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Generation of Human Antibodies to Activin A

An immunogen comprising the Activin A protein (inhibin-βA dimer) was administered directly, with an adjuvant to stimulate the immune response, to a VELOCIMMUNE® mouse comprising DNA encoding human Immunoglobulin heavy and kappa light chain variable regions. The antibody immune response was monitored by a Activin A-specific immunoassay. When a desired immune response was achieved splenocytes were harvested and fused with mouse myeloma cells to preserve their viability and form hybridoma cell lines. The hybridoma cell lines were screened and selected to identify cell lines that produce Activin A-specific antibodies. Using this technique several anti-Activin A chimeric antibodies (i.e., antibodies possessing human variable domains and mouse constant domains) were obtained. An exemplary antibody obtained in this manner is H2aM10965N. The human variable domains from the chimeric antibodies were subsequently cloned onto human constant domains to make fully human anti-Activin A antibodies as described herein.

Anti-Activin A antibodies were also isolated directly from antigen-positive B cells without fusion to myeloma cells, as described in US 2007/0280945A1. Using this method, several fully human anti-Activin A antibodies (i.e., antibodies possessing human variable domains and human constant domains) were obtained; exemplary antibodies generated in this manner were designated as follows: H4H10423P, H4H10429P, H4H10430P, H4H10432P2, H4H10440P2, H4H10442P2, H4H10436P2, and H4H10446P2.

Certain biological properties of the exemplary anti-Activin A antibodies generated in accordance with the methods of this Example are described in detail in the Examples set forth below.

Example 2

Heavy and Light Chain Variable Region Amino Acid Sequences

Table 1 sets forth the heavy and light chain variable region amino acid sequence pairs of selected anti-Activin A antibodies and their corresponding antibody identifiers. The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H10423P | 2 | 4 | 6 | 8 | 10 | 12 | 14 | 16 |
| H4H10424P | 18 | 20 | 22 | 24 | 26 | 28 | 30 | 32 |
| H4H10426P | 34 | 36 | 38 | 40 | 42 | 44 | 46 | 48 |
| H4H10429P | 50 | 52 | 54 | 56 | 58 | 60 | 62 | 64 |
| H4H10430P | 66 | 68 | 70 | 72 | 74 | 76 | 78 | 80 |
| H4H10432P2 | 82 | 84 | 86 | 88 | 90 | 92 | 94 | 96 |
| H4H10433P2 | 98 | 100 | 102 | 104 | 90 | 92 | 94 | 96 |
| H4H10436P2 | 106 | 108 | 110 | 112 | 90 | 92 | 94 | 96 |
| H4H10437P2 | 114 | 116 | 118 | 120 | 90 | 92 | 94 | 96 |
| H4H10438P2 | 122 | 124 | 126 | 128 | 90 | 92 | 94 | 96 |
| H4H10440P2 | 130 | 132 | 134 | 136 | 90 | 92 | 94 | 96 |
| H4H10442P2 | 138 | 140 | 142 | 144 | 146 | 148 | 150 | 152 |
| H4H10445P2 | 154 | 156 | 158 | 160 | 146 | 148 | 150 | 152 |
| H4H10446P2 | 162 | 164 | 166 | 168 | 146 | 148 | 150 | 152 |
| H4H10447P2 | 170 | 172 | 174 | 176 | 146 | 148 | 150 | 152 |
| H4H10448P2 | 178 | 180 | 182 | 184 | 146 | 148 | 150 | 152 |
| H4H10452P2 | 186 | 188 | 190 | 192 | 146 | 148 | 150 | 152 |
| H4H10468P2 | 194 | 196 | 198 | 200 | 146 | 148 | 150 | 152 |
| H2aM10965N | 202 | 204 | 206 | 208 | 210 | 212 | 214 | 216 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H10423P | 1 | 3 | 5 | 7 | 9 | 11 | 13 | 15 |
| H4H10424P | 17 | 19 | 21 | 23 | 25 | 27 | 29 | 31 |
| H4H10426P | 33 | 35 | 37 | 39 | 41 | 43 | 45 | 47 |
| H4H10429P | 49 | 51 | 53 | 55 | 57 | 59 | 61 | 63 |
| H4H10430P | 65 | 67 | 69 | 71 | 73 | 75 | 77 | 79 |
| H4H10432P2 | 81 | 83 | 85 | 87 | 89 | 91 | 93 | 95 |
| H4H10433P2 | 97 | 99 | 101 | 103 | 89 | 91 | 93 | 95 |
| H4H10436P2 | 105 | 107 | 109 | 111 | 89 | 91 | 93 | 95 |
| H4H10437P2 | 113 | 115 | 117 | 119 | 89 | 91 | 93 | 95 |
| H4H10438P2 | 121 | 123 | 125 | 127 | 89 | 91 | 93 | 95 |
| H4H10440P2 | 129 | 131 | 133 | 135 | 89 | 91 | 93 | 95 |
| H4H10442P2 | 137 | 139 | 141 | 143 | 145 | 147 | 149 | 151 |
| H4H10445P2 | 153 | 155 | 157 | 159 | 145 | 147 | 149 | 151 |
| H4H10446P2 | 161 | 163 | 165 | 167 | 145 | 147 | 149 | 151 |
| H4H10447P2 | 169 | 171 | 173 | 175 | 145 | 147 | 149 | 151 |
| H4H10448P2 | 177 | 179 | 181 | 183 | 145 | 147 | 149 | 151 |
| H4H10452P2 | 185 | 187 | 189 | 191 | 145 | 147 | 149 | 151 |
| H4H10468P2 | 193 | 195 | 197 | 199 | 145 | 147 | 149 | 151 |
| H2aM10965N | 201 | 203 | 205 | 207 | 209 | 211 | 213 | 215 |

Antibodies are typically referred to herein according to the following nomenclature: Fc prefix (e.g. "H1M," "H2aM," "H4H"), followed by a numerical identifier (e.g. "10423," "10424," or "10426" as shown in Tables 1 and 2), followed by a "P," "P2" or "N" suffix. Thus, according to this nomenclature, an antibody may be referred to herein as, e.g., "H4H10423P," "H4H10432P2," "H2aM10965N," etc. The H1M, H2M and H4H prefixes on the antibody designations used herein indicate the particular Fc region isotype of the antibody. For example, an "H2aM" antibody has a mouse IgG2a Fc, whereas an "H4H" antibody has a human IgG4 Fc. As will be appreciated by a person of ordinary skill in the art, an antibody having a particular Fc isotype can be converted to an antibody with a different Fc isotype (e.g., an antibody with a mouse IgG2a Fc can be converted to an antibody with a human IgG4, etc.), but in any event, the variable domains (including the CDRs)—which are indicated by the numerical identifiers shown in Table 1—will remain the same, and the binding properties are expected to be identical or substantially similar regardless of the nature of the Fc domain.

Control Constructs Used in the Following Examples

Anti-Activin A control molecules were included in the following Examples for comparative purposes. The control antibody designated herein as Control 1 is a human anti-Activin A antibody with heavy and light chain variable domain sequences of "A1" as set forth in U.S. Pat. No. 8,309,082. Control 2 is an anti-human Activin Receptor Type II B antibody (anti-ActR2B mAb) disclosed as MOR8159 in U.S. Patent Application No. 2012/0237521 A1. Control 3 is a murine anti-Activin A monoclonal antibody from R&D Systems, Minneapolis, Minn. (catalog number MAB3381). Control 4 is an Activin Type IIB receptor-Fc fusion molecule (a soluble Activin RIIB receptor extracellular domain produced with a C-terminal human IgG1 Fc fusion protein (E23-P133 of NP_001097 followed by a Gly-Ser linker followed by a C-terminal human IgG1 Fc fusion), the sequence of which is provided as SEQ ID NO:227.

Example 3

Antibody Binding to Human Activin A as Determined by Surface Plasmon Resonance Binding affinities and kinetic constants for antigen binding to selected purified anti-human Activin A monoclonal antibodies were determined using a real-time surface plasmon resonance biosensor (Biacore T200 or Biacore 4000, GE Healthcare Life Sciences, Piscataway, N.J.) assay at 25° C. and 37° C. Antibodies, expressed as either mouse Fc (prefix H2aM) or human Fc (prefix H4H), were captured on their respective anti-Fc sensor surfaces (mAb capture format). Anti-Activin A antibodies were captured on either a goat anti-mouse IgG polyclonal antibody (GE Healthcare, #BR-1008-38) or a mouse anti-human IgG monoclonal antibody (GE Healthcare, #BR-1008-39) surface created through direct amine coupling to a Biacore CM5 sensor chip. Kinetic experiments were carried out using either HBS-EP (10 mM HEPES, 150 mM NaCl, 3 mM EDTA, 0.05% Surfactant P20, at pH 7.4) or PBS-P (10 mM Sodium Phosphate, 2.7 mM KCl, 137 mM NaCl, 0.02% NaN3, 0.05% Surfactant P20, pH 7.4), as both the running buffer and the sample buffer. Antigen-antibody association rates were measured by injecting various concentrations (4-fold dilutions ranging from 50 to 0.2 nM) of either Activin A (R&D Systems, #338-AC-050/CF), Activin B (R&D Systems, #659-AB-025/CF), Activin AB (R&D Systems, #1006-AB-005), Activin AC (R&D Systems, #4879-AC/CF), or Inhibin E (Novus Biologicals, #H00083729-P01) over the captured antibody surface. Antibody-antigen association was monitored for 240 seconds while dissociation in buffer was monitored for 600 seconds. Kinetic association and dissociation rate constants were determined by processing and fitting the data using Scrubber software version 2.0c. Binding equilibrium dissociation constants ($K_D$) and dissociative half-lives ($t_{1/2}$) were then calculated from the kinetic rate constants as: $K_D$ (M)=$k_d/k_a$ and $t_{1/2}$ (min)=[ln 2/(60*$k_d$)]. Kinetic binding parameters for different anti-Activin A monoclonal antibodies are shown in Tables 3 to 10. (NB=no binding observed under the conditions used; NT=not tested).

TABLE 3

Binding Characteristics of Anti-Activin A Antibodies to Activin A at 25° C.

| Antibody | Amount of mAb Captured (RU ± SE) | Activin A- 20 nM (RU) | $k_a$ (M$^{-1}$s$^{-1}$) | $k_d$ (s$^{-1}$) | $K_D$ (Molar) | $t_{1/2}$ (min) |
|---|---|---|---|---|---|---|
| H4H10423P | 86.2 ± 0.7 | 19.4 | 3.33E+06 | 1.09E−04 | 3.26E−11 | 106.4 |
| H4H10424P | 337 | 82 | 3.14E+06 | 7.19E−04 | 2.29E−10 | 16 |
| H4H10426P | 81 | 23 | 1.18E+07 | 7.00E−04 | 5.95E−11 | 16 |
| H4H10429P | 115.2 ± 1 | 24.9 | 7.82E+06 | 6.39E−05 | 8.17E−12 | 180.8 |
| H4H10430P | 90.3 ± 4.2 | 19.4 | 4.75E+07 | 1.67E−04 | 3.52E−12 | 69 |
| H4H10432P2 | 109.6 ± 1.2 | 20.7 | 1.57E+07 | *5.00E−05* | ≤3.18E−12 | ≥231 |
| H4H10433P2 | 102 | 16 | 1.42E+07 | 5.77E−04 | 4.06E−11 | 20 |
| H4H10436P2 | 113.6 ± 0.6 | 23.2 | 8.85E+06 | 1.68E−04 | 1.90E−11 | 68.7 |
| H4H10437P2 | 167 | 30 | 1.58E+07 | 2.13E−03 | 1.34E−10 | 5 |
| H4H10438P2 | 124 | 25 | 1.20E+07 | 5.88E−04 | 4.92E−11 | 20 |
| H4H10440P2 | 79.2 ± 0.7 | 12.9 | 3.76E+06 | 9.28E−05 | 2.47E−11 | 124.5 |
| H4H10442P2 | 139.3 ± 1 | 31.3 | 1.10E+07 | *5.00E−05* | ≤4.55E−12 | ≥231 |
| H4H10445P2 | 149 | 43 | 2.40E+06 | *5.00E−05* | ≤2.08E−11 | ≥231 |
| H4H10446P2 | 104.6 ± 0.7 | 24.1 | 1.29E+07 | *5.00E−05* | ≤3.88E−12 | ≥231 |
| H4H10447P2 | 164 | 43 | 2.36E+06 | *5.00E−05* | ≤2.12E−11 | ≥231 |
| H4H10448P2 | 244 | 64 | 4.76E+06 | *5.00E−05* | ≤1.05E−11 | ≥231 |
| H4H10452P2 | 191 | 55 | 4.69E+06 | *5.00E−05* | ≤1.07E−11 | ≥231 |
| H4H10468P2 | 93 ± 0.1 | 21.7 | 7.86E+06 | *5.00E−05* | ≤6.36E−12 | ≥231 |
| H2aM10965N | 393 | 76 | 1.48E+06 | 1.10E−03 | 7.45E−10 | 10 |
| Control 1 | 84.7 ± 0.3 | 15.9 | 7.26E+06 | 9.92E−05 | 1.37E−11 | 116.4 |

For $k_d$ values that are italicized, no dissociation of the analyte was observed under these experimental conditions, and the value of $k_d$ was therefore fixed at 5.0E−05 s$^{-1}$

TABLE 4

Binding Characteristics of Anti-Activin A Antibodies to to Activin A at 37° C.

| Antibody | Amount of mAb Captured (RU ± SE) | Activin A- 20 nM (RU) | $k_a$ (M$^{-1}$s$^{-1}$) | kd (s$^{-1}$) | $K_D$ (Molar) | $t_{1/2}$ (min) |
|---|---|---|---|---|---|---|
| H4H10423P | 101 ± 1.4 | 25.2 | 3.95E+06 | *5.00E−05* | ≤1.26E−11 | ≥231 |
| H4H10424P | 231 | 58 | 4.59E+06 | 3.64E−03 | 7.94E−10 | 3 |
| H4H10426P | 71 | 21 | 1.61E+07 | 1.98E−03 | 1.23E−10 | 6 |
| H4H10429P | 150.8 ± 5.3 | 31.4 | 1.33E+07 | *5.00E−05* | ≤3.75E−12 | ≥231 |
| H4H10430P | 109.3 ± 1.3 | 25.0 | 3.80E+07 | 1.51E−04 | 3.97E−12 | 76.5 |
| H4H10432P2 | 141.8 ± 1.6 | 25.1 | 2.30E+07 | *5.00E−05* | ≤2.18E−12 | ≥231 |
| H4H10433P2 | 85 | 12 | 2.00E+07 | 1.07E−03 | 5.37E−11 | 11 |

TABLE 4-continued

Binding Characteristics of Anti-Activin A Antibodies to Activin A at 37° C.

| Antibody | Amount of mAb Captured (RU ± SE) | Activin A- 20 nM (RU) | $k_a$ (M$^{-1}$s$^{-1}$) | kd (s$^{-1}$) | $K_D$ (Molar) | $t_{1/2}$ (min) |
|---|---|---|---|---|---|---|
| H4H10436P2 | 139.8 ± 1.4 | 29.4 | 1.49E+07 | *5.00E−05* | ≤3.35E−12 | ≥231 |
| H4H10437P2 | 115 | 20 | 2.04E+07 | 4.68E−03 | 2.29E−10 | 2 |
| H4H10438P2 | 99 | 18 | 1.87E+07 | 2.38E−03 | 1.27E−10 | 5 |
| H4H10440P2 | 98.6 ± 1.1 | 15.3 | 6.37E+06 | 3.28E−04 | 5.15E−11 | 35.2 |
| H4H10442P2 | 181 ± 2.5 | 40.5 | 1.44E+07 | *5.00E−05* | ≤3.48E−12 | ≥231 |
| H4H10445P2 | 120 | 36 | 4.33E+06 | *5.00E−05* | ≤1.15E−11 | ≥231 |
| H4H10446P2 | 137.2 ± 1.7 | 31.5 | 1.54E+07 | *5.00E−05* | ≤3.25E−12 | ≥231 |
| H4H10447P2 | 126 | 36 | 4.69E+06 | *5.00E−05* | ≤1.07E−11 | ≥231 |
| H4H10448P2 | 175 | 49 | 7.86E+06 | *5.00E−05* | ≤6.36E−12 | ≥231 |
| H4H10452P2 | 146 | 43 | 7.94E+06 | *5.00E−05* | ≤6.30E−12 | ≥231 |
| H4H10468P2 | 98.7 ± 0.7 | 24.5 | 1.22E+07 | *5.00E−05* | ≤4.10E−12 | ≥231 |
| H2aM10965N | 435 | 80 | 2.35E+06 | 4.15E−03 | 1.77E−09 | 3 |
| Control 1 | 93.9 ± 0.7 | 18.0 | 8.99E+06 | *5.00E−05* | ≤5.56E−12 | ≥231 |

For $k_d$ values that are italicized, no dissociation of the analyte was observed under these experimental conditions, and the value of $k_d$ was therefore fixed at 5.0E−05 s$^{-1}$

TABLE 5

Binding Characteristics of Anti-Activin A Antibodies to Activin B at 25° C.

| Antibody | Amount of mAb Captured (RU ± SE) | 50 nM Ag Bound (RU) | $k_a$ (M$^{-1}$s$^{-1}$) | $k_d$ (s$^{-1}$) | $K_D$ (Molar) | $t_{1/2}$ (min) |
|---|---|---|---|---|---|---|
| H4H10423P | 83.1 ± 0.6 | 4.7 | 4.89E+05 | 3.02E−02 | 6.18E−08 | 0.4 |
| H4H10429P | 112.3 ± 0.7 | 26.4 | 3.49E+06 | 1.31E−02 | 3.75E−09 | 0.9 |
| H4H10432P2 | 104.4 ± 1.8 | 5.1 | NB | NB | NB | NB |
| H4H10436P2 | 110.8 ± 3.9 | 32.8 | 9.52E+06 | 5.28E−04 | 5.54E−11 | 21.9 |
| H4H10440P2 | 75.7 ± 0.8 | 18.8 | 1.06E+06 | 1.16E−03 | 1.09E−09 | 10.0 |
| H4H10442P2 | 136 ± 0.7 | 3.4 | NB | NB | NB | NB |
| H4H10430P | 88 ± 0.5 | 3.9 | NB | NB | NB | NB |
| H4H10446P2 | 101.5 ± 0.4 | 3.6 | NB | NB | NB | NB |
| H4H10468P2 | 92.5 ± 0.2 | 6.2 | NB | NB | NB | NB |
| Control 1 | 84.1 ± 0.3 | 6.4 | NB | NB | NB | NB |

TABLE 6

Binding Characteristics of Anti-Activin A Antibodies to Activin B at 37° C.

| Antibody | Amount of mAb Captured (RU ± SE) | 50 nM Ag Bound (RU) | $k_a$ (M$^{-1}$s$^{-1}$) | $k_d$ (s$^{-1}$) | $K_D$ (Molar) | $t_{1/2}$ (min) |
|---|---|---|---|---|---|---|
| H4H10423P | 96 ± 1.2 | 4.4 | NB | NB | NB | NB |
| H4H10429P | 142.8 ± 1.3 | 25.3 | 3.43E+06 | 3.43E−02 | 9.98E−09 | 0.3 |
| H4H10432P2 | 134.1 ± 1.7 | 5.1 | NB | NB | NB | NB |
| H4H10436P2 | 132 ± 1.4 | 38.1 | 9.78E+06 | 1.36E−03 | 1.39E−10 | 8.5 |
| H4H10440P2 | 94 ± 4.5 | 20.9 | 1.28E+06 | 4.19E−03 | 3.29E−09 | 2.8 |
| H4H10442P2 | 173.1 ± 1.4 | 4.4 | NB | NB | NB | NB |
| H4H10430P | 105.8 ± 1.3 | 3.6 | NB | NB | NB | NB |
| H4H10446P2 | 131.4 ± 1.2 | 3.8 | NB | NB | NB | NB |
| H4H10468P2 | 95.5 ± 1 | 3.4 | NB | NB | NB | NB |
| Control 1 | 90.2 ± 0.9 | 2.7 | NB | NB | NB | NB |

TABLE 7

Binding Characteristics of Anti-Activin A Antibodies to Activin AB at 25° C.

| Antibody | Amount of mAb Captured (RU ± SE) | 50 nM Ag Bound (RU) | $k_a$ (M$^{-1}$s$^{-1}$) | $k_d$ (s$^{-1}$) | $K_D$ (Molar) | $t_{1/2}$ (min) |
| --- | --- | --- | --- | --- | --- | --- |
| H4H10423P | 81.3 ± 0.5 | 14.7 | 6.13E+05 | 2.03E−02 | 3.31E−08 | 0.6 |
| H4H10429P | 110.7 ± 0.5 | 40.0 | 4.53E+06 | 1.03E−04 | 2.28E−11 | 111.7 |
| H4H10432P2 | 101.2 ± 1.6 | 38.3 | 4.00E+06 | 2.27E−03 | 5.68E−10 | 5.1 |
| H4H10436P2 | 107.5 ± 0.3 | 28.2 | 7.66E+06 | 2.61E−04 | 3.41E−11 | 44.2 |
| H4H10440P2 | 73.7 ± 0.4 | 15.5 | 2.97E+06 | 5.26E−04 | 1.77E−10 | 22.0 |
| H4H10442P2 | 133.3 ± 0.6 | 34.6 | 5.53E+06 | 1.77E−03 | 3.20E−10 | 6.5 |
| H4H10430P | 86.9 ± 0.5 | 33.0 | 1.17E+07 | 2.17E−04 | 1.85E−11 | 53.3 |
| H4H10446P2 | 99.8 ± 0.4 | 31.9 | 4.99E+06 | 4.06E−03 | 8.15E−10 | 2.8 |
| H4H10468P2 | 92.1 ± 0.2 | 34.7 | 3.76E+06 | 2.09E−03 | 5.56E−10 | 5.5 |
| Control 1 | 83.5 ± 0.6 | 31.1 | 3.44E+06 | 2.83E−04 | 8.22E−11 | 40.9 |

TABLE 8

Binding Characteristics of Anti-Activin A Antibodies to Activin AB at 37° C.

| Antibody | Amount of mAb Captured (RU ± SE) | 50 nM Ag Bound (RU) | $k_a$ (M$^{-1}$s$^{-1}$) | $k_d$ (s$^{-1}$) | $K_D$ (Molar) | $t_{1/2}$ (min) |
| --- | --- | --- | --- | --- | --- | --- |
| H4H10423P | 90.8 ± 1.2 | 21.7 | 8.80E+05 | 2.13E−02 | 2.42E−08 | 0.5 |
| H4H10429P | 137.7 ± 1.2 | 50.0 | 6.47E+06 | 4.88E−04 | 7.55E−11 | 23.6 |
| H4H10432P2 | 127.7 ± 1.3 | 44.4 | 5.40E+06 | 5.92E−03 | 1.10E−09 | 2.0 |
| H4H10436P2 | 126.8 ± 0.8 | 33.9 | 1.03E+07 | 4.58E−04 | 4.43E−11 | 25.2 |
| H4H10440P2 | 88.9 ± 1.7 | 17.7 | 5.20E+06 | 1.63E−03 | 3.14E−10 | 7.1 |
| H4H10442P2 | 166.5 ± 1.7 | 45.9 | 9.17E+06 | 4.25E−03 | 4.64E−10 | 2.7 |
| H4H10430P | 101.6 ± 1.2 | 41.0 | 1.01E+07 | 5.41E−04 | 5.35E−11 | 21.3 |
| H4H10446P2 | 126.6 ± 1.2 | 41.5 | 6.08E+06 | 8.17E−03 | 1.34E−09 | 1.4 |
| H4H10468P2 | 92.2 ± 0.8 | 34.5 | 5.03E+06 | 4.43E−03 | 8.80E−10 | 2.6 |
| Control 1 | 86.4 ± 0.6 | 29.3 | 3.77E+06 | 7.38E−04 | 1.96E−10 | 15.7 |

TABLE 9

Binding Characteristics of Anti-Activin A Antibodies to Activin AC at 25° C.

| Antibody | Amount of mAb Captured (RU ± SE) | 50 nM Ag Bound (RU) | $k_a$ (M$^{-1}$s$^{-1}$) | $k_d$ (s$^{-1}$) | $K_D$ (Molar) | $t_{1/2}$ (min) |
| --- | --- | --- | --- | --- | --- | --- |
| H4H10423P | 79.9 ± 0.4 | −0.8 | NB | NB | NB | NB |
| H4H10429P | 108.9 ± 0.5 | 28.0 | 9.13E+05 | 9.10E−05 | 9.97E−11 | 126.9 |
| H4H10432P2 | 101.6 ± 0.7 | 34.9 | 6.29E+05 | 1.87E−03 | 2.98E−09 | 6.2 |
| H4H10436P2 | 106.7 ± 0.4 | 30.1 | 6.98E+05 | 1.56E−03 | 2.24E−09 | 7.4 |
| H4H10440P2 | 73.5 ± 0.4 | 11.8 | 5.13E+05 | 2.27E−04 | 4.42E−10 | 50.8 |
| H4H10442P2 | 132.5 ± 3.1 | 18.6 | 1.31E+06 | 2.05E−03 | 1.57E−09 | 5.6 |
| H4H10430P | 85.1 ± 0.3 | 23.6 | 1.23E+06 | 1.09E−02 | 8.86E−09 | 1.1 |
| H4H10446P2 | 96.9 ± 0.5 | 12.6 | 1.04E+06 | 1.22E−02 | 1.18E−08 | 0.9 |
| H4H10468P2 | 91.4 ± 0.3 | 17.2 | 7.98E+05 | 5.92E−03 | 7.41E−09 | 2.0 |
| Control 1 | 82.5 ± 0.3 | 22.3 | 5.58E+05 | 2.25E−03 | 4.03E−09 | 5.1 |

TABLE 10

Binding Characteristics of Anti-Activin A Antibodies to Activin AC at 37° C.

| Antibody | Amount of mAb Captured (RU ± SE) | 50 nM Ag Bound (RU) | $k_a$ (M$^{-1}$s$^{-1}$) | $k_d$ (s$^{-1}$) | $K_D$ (Molar) | $t_{1/2}$ (min) |
|---|---|---|---|---|---|---|
| H4H10423P | 85.9 ± 1.1 | 0.0 | NB | NB | NB | NB |
| H4H10429P | 132.6 ± 1.2 | 35.7 | 1.34E+06 | 6.20E−04 | 4.62E−10 | 18.6 |
| H4H10432P2 | 123.8 ± 1.4 | 34.6 | 7.22E+05 | 9.02E−03 | 1.25E−08 | 1.3 |
| H4H10436P2 | 122.9 ± 1.3 | 32.6 | 8.81E+05 | 3.31E−03 | 3.75E−09 | 3.5 |
| H4H10440P2 | 86.6 ± 2.7 | 13.3 | 7.18E+05 | 7.55E−04 | 1.05E−09 | 15.3 |
| H4H10442P2 | 160.1 ± 1.5 | 21.4 | 1.46E+06 | 5.99E−03 | 4.10E−09 | 1.9 |
| H4H10430P | 96.8 ± 1 | 25.3 | 1.20E+06 | 2.00E−02 | 1.67E−08 | 0.6 |
| H4H10446P2 | 120.3 ± 1 | 14.4 | 9.59E+05 | 2.16E−02 | 2.25E−08 | 0.5 |
| H4H10468P2 | 88.4 ± 0.8 | 10.7 | 7.19E+05 | 1.24E−02 | 1.73E−08 | 0.9 |
| Control 1 | 83.2 ± 0.9 | 15.6 | 6.51E+05 | 6.52E−03 | 1.00E−08 | 1.8 |

As shown in Tables 3 and 4, anti-Activin A antibodies of the invention bound to Activin A with $K_D$ values ranging from less than 3.18 pM (i.e., ≤3.18E−12) to 745 pM (i.e., 7.45E−10) at 25° C. and with $K_D$ values ranging from less than 2.18 pM (i.e., ≤2.18E−12) to 1.77 nM (1.77E−09) at 37° C. As shown in Tables 5 and 6, several of the anti-Activin A antibodies (i.e., H4H10432P2, H4H10442P2, H4H10430P2, H4H10446P2, and H4H10468P2) demonstrated no measurable binding to Activin B at 25° C. or 37° C. Some of the antibodies demonstrated measurable binding to Activin AB with $K_D$ values ranging from approximately 18.5 pM (i.e., 1.85E−11) to 33.1 nM (i.e., 3.31E−08) at 25° C. (Table 7) and from approximately 44.3 pM (i.e., 4.43E−11) to 24.2 nM (i.e., 2.42E−08) at 37° C. (Table 8). Some of the antibodies demonstrated measurable binding to Activin AC with $K_D$ values ranging from approximately 99.7 pM (i.e., 9.97E−11) to 11.8 nM (i.e., 1.18E−08) at 25° C. (Table 9) and from approximately 462 pM (i.e., 4.62E−10) to 22.5 nM (i.e., 2.25E−08) at 37° C. (Table 10). Furthermore, none of the tested anti-Activin A antibodies of the invention demonstrated measurable binding to Inhibin E (data not shown).

Example 4

Antibody Binding to TGF-Beta Family Members as Determined by Surface Plasmon Resonance Activin A mAbs were tested for binding cross-reactivity to a panel of TGF-beta family members. For the binding experiment, a Biacore 4000 instrument was used. The antibodies H4H10429P, H4H10430P, H4H10436P2, H4H10442P2, H4H10446P2; Control 4 (the ActR2B soluble ecto domain protein produced with a C-terminal human IgG1 Fc tag (ActR2B-hFc; SEQ ID NO:227)); and an isotype control antibody were captured on a Biacore CM4 biosensor chip that was first derivatized by amine coupling with a monoclonal mouse anti-human Fc antibody (GE, Catalog# BR-1008-39). All Biacore binding studies were performed in HBS-T running buffer (0.01 M HEPES pH 7.4, 0.5 M NaCl, 3 mM EDTA, 0.5 mg/ml bovine serum albumin, 0.05% v/v Surfactant P20). Human TGF-beta family member ligands were purchased from R&D systems (Activin A, #338-AC; Activin B, #659-AB; Activin AB, #1066-AB; Activin AC, #4879-AC; BPM2, #355-BM; hBMP4, #314-BP; hBMP6, #507-BP; hBMP7, #354-BP; hBMP9, #3209-BP; hBMP10, #2926-BP; hGDF8, #788-G8; hGDF11, #1958-GD). All binding measurements were performed at 37° C. Capture levels ranging from 60-200 resonance units (RUs) were obtained for each of the antibodies or the soluble receptor. Over the captured antibody surface was injected the TGF-beta family ligands through concentrations ranging from 3.1 nM to 200 nM. Binding values for the 200 nM analyte injections are shown in Table 11.

TABLE 11

Binding of anti-Activin A monoclonal antibodies to human TGF-β family ligands at 37° C.

| TGF-beta family ligand tested | Binding response (resonance units) for 200 nM of TGF-beta family ligand injected over captured antibody sensor surface | | | | | | | |
|---|---|---|---|---|---|---|---|---|
| | H4H10429P | H4H10430P | H4H10436P2 | H4H10442P2 | H4H10446P2 | H4H8925C | Control 4 (ActR2B-hFc) (Positive Control) | Isotype Control mAb |
| Activin A | 56.8 | 69.1 | 56.5 | 63.9 | 53.2 | 67.6 | 70.9 | −0.1 |
| Activin B | 51.5 | 0.4 | 60.1 | −1.8 | 2.6 | 0.3 | 68.0 | 1.9 |
| Activin AB | 76.5 | 95.0 | 54.3 | 65.2 | 66.7 | 102.0 | 59.5 | −0.1 |
| Activin AC | 43.1 | 34.8 | 55.6 | 14.2 | 15.2 | 32.5 | 59.4 | −0.1 |
| hBMP2 | 3.6 | −1.7 | 14.9 | −2.3 | 3.3 | −4.0 | 36.9 | −1.0 |
| hBMP4 | 1.1 | −0.6 | 19.3 | −0.7 | 0.8 | −0.5 | 26.4 | 0.4 |
| hBMP6 | 4.6 | 5.7 | 4.0 | 1.1 | 5.3 | 4.8 | 86.3 | 5.1 |
| hBMP7 | 9.2 | 6.4 | 13.6 | 1.5 | 5.7 | 4.5 | 64.2 | 4.3 |
| hBMP9 | 33.4 | −0.6 | 11.7 | 0.0 | −0.3 | −0.1 | 32.3 | −1.0 |
| hBMP10 | 32.4 | 0.3 | 22.5 | −0.7 | 0.5 | 0.0 | 34.2 | 0.3 |

TABLE 11-continued

Binding of anti-Activin A monoclonal antibodies to human TGF-β family ligands at 37° C.

| TGF-beta family ligand tested | Binding response (resonance units) for 200 nM of TGF-beta family ligand injected over captured antibody sensor surface | | | | | | | |
|---|---|---|---|---|---|---|---|---|
| | H4H10429P | H4H10430P | H4H10436P2 | H4H10442P2 | H4H10446P2 | H4H8925C | Control 4 (ActR2B-hFc) (Positive Control) | Isotype Control mAb |
| GDF8 | −0.4 | −0.1 | −0.5 | 0.5 | 0.7 | −0.1 | 25.8 | 0.5 |
| GDF11 | 1.6 | 3.0 | 0.0 | 1.0 | 1.8 | 3.3 | 24.2 | 3.0 |

The observed binding responses of the captured activin A antibodies to the injected TGF-beta family ligands at 200 nM could be compared to the binding responses of a negative control antibody (Isotype Control mAb), which provides a measure of background-level non-specific binding, and to the binding responses of ActR2B-hFc, which was observed to bind to the entire panel of TGF-beta family members tested and therefore serves as a positive control ligand-binding protein (Table 11). From this comparison, it was found that several of the antibodies (e.g., H4H10430, H4H10442, H4H20446) bound to Activin A, Activin AB, Activin AC but not appreciably to Activin B or to the BMP or GDF ligands. It was also found that some of the antibodies bound with broader cross-reactivity to additional TGF-beta family ligands. For example, H4H10429P bound appreciably to Activin A, Activin B, Activin AB, Activin AC and also to BMP9 and BMP10. H4H10436P2 showed appreciable binding to Activin A, Activin B, Activin AB, Activin AC, BMP2, BMP4, BMP7, BMP9, and BMP10. From these data it is shown that antibodies with different binding specificities to TGF-beta family ligands can be obtained after immunizing mice with the Activin A ligand.

Example 5

Cross-Competition Analysis of Anti-Activin A Antibodies

Figure 1:
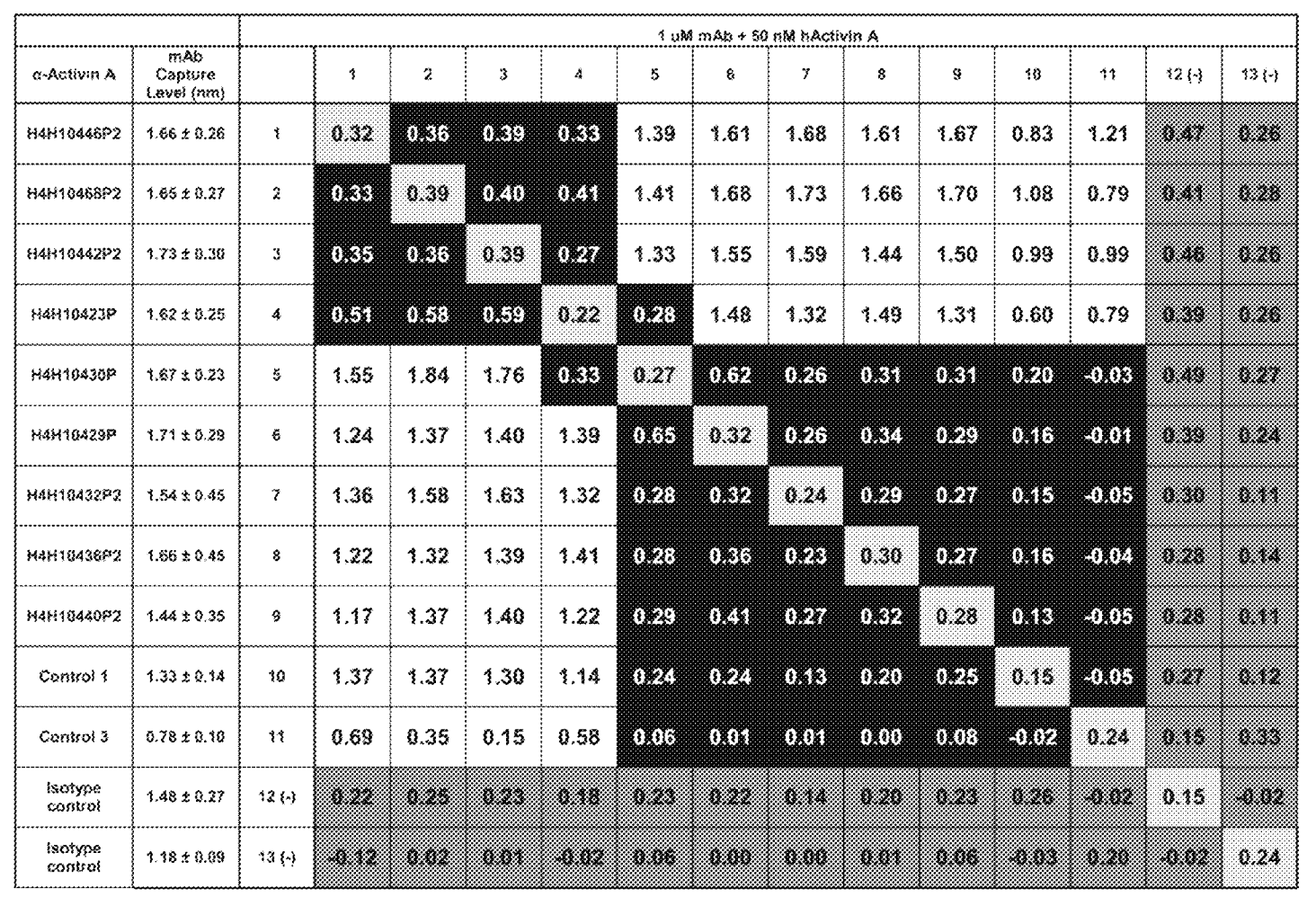

A cross-competition assay was conducted to assess the ability of a panel of 9 antibodies (H4H10446P2, H4H10468P2, H4H10442P2, H4H10423P, H4H10430P, H4H10429P, H4H10432P2, H4H10436P2 and H4H10440P2) to compete with one another for binding to human Activin A. Two isotype control antibodies and two control Activin A antibodies, Control 1 (a human anti-Activin A antibody with heavy and light chain variable domain sequences of "A1" as set forth in U.S. Pat. No. 8,309,082) and Control 3 (MAB3381, available from R&D Systems, Inc., Minneapolis, Minn.) were also included in the assays. All assays were performed at 25° C. with a microtiter plate shaking rate of 1000 rpm in Octet HBST buffer (0.01 M HEPES pH7.4, 0.15M NaCl, 3 mM EDTA, 0.05% v/v Surfactant P20, 0.1 mg/mL BSA) according to manufacturer's instructions (ForteBio Corp., Menlo Park, Calif.). Briefly, an amount of anti-Activin A antibody giving a binding response of approximately 1.8 nm was captured onto anti-human Fc antibody coated Octet sensor tips (Fortebio, #18-0015) by dipping the tips for 5 minutes in a 10 μg/mL solutions of each anti-Activin A antibody. Any remaining anti-hFc binding sites on the tips were blocked by incubating the tips in a 50 ug/mL solution of irrelevant antibody for 5 minutes. Sensor tips were then submerged into wells containing a solution of 50 nM Activin A (R&D Systems, #338-AC/CF) pre-bound with 1 μM of a second anti-Activin A antibody. Binding of the second Activin A antibody/Activin A solution to the Activin A antibody coated sensor tip was monitored for 5 minutes at 1000 rpm. The response of the mAb/Activin A complex binding to the anti-Activin A coated sensor tip was compared and competitive/non-competitive behavior of different anti-Activin A monoclonal antibodies was determined. Results are illustrated in FIG. 1.

In FIG. 1, competitive binding responses are shown in black or light gray shading and indicate that the corresponding antibody pairs compete with one another for binding to Activin A. Light gray boxes with black font represent binding response for self-competition between the same antibodies. Black boxes with white font represent antibodies that compete for Activin A binding in both directions, independent of the order of binding. Dark grey boxes with black font represent readings for isotype control (i.e., non-binding) antibodies, indicating a lack of binding of isotype control antibodies to anti-Activin A antibody-Activin A complexes (when isotype control antibodies are bound to the Octet sensor tip) or the lack of binding of isotype control antibodies to Activin A (when isotype control antibodies are used as the second antibody in wells with Activin A). White boxes with black font represent no competition between antibodies, which suggests the antibodies have distinct binding epitopes on Activin A.

Four antibodies, H4H10446P2, H4H10468P2, H4H10442P2, and H4H10423P, bi-directionally compete with each other for binding to Activin A. Additionally, these four antibodies do not compete with Control 1 or Control 3 for binding. Three of these four Activin A antibodies, H4H10446P2, H4H10468P2, and H4H10442P2, do not cross compete with any other Activin A antibodies. One of the four antibodies (H4H10423P) also bidirectionally competes with H4H10430P for binding to Activin A. Five antibodies, H4H10430P, H4H10429, H4H10432P2, H4H10436P2, and H4H10440P2, bi-directionally compete with each other for binding to Activin A, as well as with Control 1 and Control 3. Four of these five antibodies (i.e., H4H10429, H4H10432P2, H4H10436P2, and H4H10440P2) do not cross compete with any other Activin A antibodies, whereas H4H10423P also cross-competes with H4H10430P, as noted above.

The results of this Example indicate that the anti-Activin A antibodies of the invention can be grouped into two distinct "bins" based on epitope binding characteristics: Bin 1 includes H4H10423P, H4H10446P2, H4H10468P2 and H4H10442P2. Bin 2 includes H4H10429, H4H1430P, H4H10432P2, H4H10436P2, and H4H10440P2. Further, one antibody from each bin, i.e., H4H10423P and H4H1430P, cross-compete with each other. The results of this Example suggest that the antibodies of Bin 1 bind to distinct regions on Activin A than the antibodies of Bin 2.

Example 6

Inhibition of Activin A-Mediated Receptor Activation and SMAD Complex Signaling with Anti-Activin A Antibodies To further characterize anti-Activin A antibodies of the present invention, a bioassay was developed to detect the activation of the activin Type IIA and IIB receptors (ActRIIA and ActRIIB, respectively) and the subsequent phosphorylation and activation of an Activin Type I receptor. The interaction between ActRIIA and ActRIIB and activin leads to the induction of diverse cellular processes including growth regulation, metastatis of cancer cells and differentiation of embryonic stem cells (Tsuchida, K. et al., Cell Commun Signal 7:15 (2009)). Phosphorylation and activation of the Type I receptor leads to phosphorylation of SMAD 2 and 3 proteins which form activated SMAD complexes leading to transcriptional regulation of genes.

To detect the activation of the SMAD complex signal transduction pathway via activin binding to activin Type II receptors, a human A204 rhabdomyosarcoma cell line (ATCC, # HTB-82) was transfected with a Smad 2/3-luciferase reporter plasmid (CAGAx12-Luc; Dennler, 1998) to create the A204/CAGAx12-Luc cell line. A204/CAGAx12-Luc cells were maintained in McCoy's 5A (Irvine Scientific, #9090) supplemented with 10% fetal bovine serum (FBS), penicillin/streptomycin/glutamine and 250 µg/mL of G418. For the bioassay, A204/CAGAx12-Luc cells were seeded onto 96-well assay plates at 10,000 cells/well in low serum media, 0.5% FBS and OPTIMEM (Invitrogen, #31985-070), and incubated at 37° C. and 5% $CO_2$ overnight. To determine the ligand dose response, Activin A (R&D Systems, #338-AC), Activin B (R&D Systems, #659-AB), Activin AB (R&D Systems, #1066-AB) and Activin AC (R&D Systems, #4879-AC/CF) were serially diluted at 1:3 from 100 to 0.002 nM and added to cells starting along with a control containing no Activin. Activin A, Activin B, Activin AB, and Activin AC were observed to activate the A204/CAGAx12-Luc cell line with $EC_{50}$ values of 99 pM, 47 pM, 19 pM, and 4.4 nM, respectively. To measure inhibition, antibodies were serially diluted at 1:3 starting from 100 to 0.002 nM, 1000 to 0.02 nM, or 300 to 0.005 nM including control samples containing either an appropriate isotype control antibody or no antibody added to cells with a constant concentration of 100 pM Activin A, 50 pM Activin B, 30 pM Activin AB or 4 nM Activin AC. Also used as a positive blocking control in this assay was Control 4 (ActRIIB-hFc; SEQ ID No:227). After 5.5 hours of incubation in 37° C. and 5% $CO_2$, OneGlo substrate (Promega, # E6051) was added and then luciferase activity was detected using a Victor X (Perkin Elmer) instrument. The results were analyzed using nonlinear regression (4-parameter logistics) with Prism 5 software (GraphPad).

As shown in Table 12, anti-Activin A antibodies of the invention blocked 100 pM of Activin A with $IC_{50}$ values ranging from 39 pM to 3.5 nM, while Control 1 blocked with an $IC_{50}$ value of 83 pM. A subset of the anti-Activin A antibodies of the invention were tested for blocking Activin B, AB, and AC. Four of the 9 antibodies tested blocked 50 pM of Activin B with $IC_{50}$ values ranging from 130 pM to 100 nM. Five antibodies of the invention that were tested for Activin B blockade only blocked at high antibody concentrations, while Control 1 did not show any measurable Activin B blockade. Eight antibodies of the invention tested blocked 30 pM of Activin AB with $IC_{50}$ values ranging from 100 pM to 8.2 nM, while Control 4 blocked with an $IC_{50}$ value of 540 pM. One antibody, H4H10423P, only demonstrated weak blockade of Activin AB. Seven of the 8 antibodies tested blocked 4 nM of Activin AC with $IC_{50}$ values ranging from 580 pM to 6.5 nM, while Control 4 blocked with an $IC_{50}$ value of 1.1 nM. One antibody, H4H10423P, did not demonstrate any blockade of Activin AC. Both mouse IgG (mIgG isotype control) and human IgG (hIgG isotype control) negative controls did not block ligand activation of the receptors.

TABLE 12

Inhibition of Activin A, Activin B, Activin AB, and Activin AC by anti-Activin A antibodies ($IC_{50}$ [M])

| Constant: Antibody | Activin A | Activin B | Activin AB | Activin AC |
|---|---|---|---|---|
| H4H10423P | 2.0E−10 | | Weak Blocker | Non-Blocker |
| H4H10424P | 7.6E−10 | | | |
| H4H10426P | 2.3E−10 | | | |
| H4H10429P | 1.6E−10 | 7.9E−08 | 2.9E−10 | 5.8E−10 |
| H4H10430P | 6.1E−11 | Block at High Conc. | 1.0E−10 | 9.3E−10 |
| H4H10432P2 | 1.1E−10 | Block at High Conc. | 8.0E−10 | 2.8E−09 |
| H4H10433P2 | 1.5E−10 | 1.0E−07 | | |
| H4H10436P2 | 2.0E−10 | 1.3E−10 | 1.4E−10 | 1.3E−09 |
| H4H10437P2 | 2.9E−10 | Block at High Conc. | | |
| H4H10438P2 | 2.6E−10 | | | |
| H4H10440P2 | 2.8E−10 | 5.2E−09 | 4.3E−10 | 7.5E−10 |
| H4H10442P2 | 5.6E−11 | | 2.2E−09 | 6.5E−09 |
| H4H10445P2 | 5.3E−11 | | | |
| H4H10446P2 | 4.7E−11 | Block at High Conc. | 8.2E−09 | 5.6E−09 |
| H4H10447P2 | 7.8E−11 | | | |
| H4H10448P2 | 4.6E−11 | | | |
| H4H10452P2 | 5.8E−11 | | | |
| H4H10468P2 | 3.9E−11 | Block at High Conc. | 2.3E−09 | 3.4E−09 |
| H2aM10965N mIgG isotype control | 3.5E−09 Non-Blocker | | | |
| hIgG isotype control | Non-Blocker | Non-Blocker | Non-Blocker | Non-Blocker |
| Control 1 | 8.3E−11 | Non-Blocker | 5.4E−10 | 1.1E−09 |

The bioassay using A204/CAGAx12-Luc cells could also be stimulated by GDF8 (R&D Systems, Cat #788-G8/CF) and GDF11 (R&D Systems, Cat #1958-GD-010/CF). To test for functional inhibition of these ligands with activin A antibodies, the assay was performed using conditions described above but substituting GDF8 or GDF11 for the activating ligand, which resulted in EC50 values of 188 pM and 84 pM, respectively. In this assay, activation by a constant concentration of 0.50 nM GDF8 or 0.40 nM GDF11 was completely blocked by Control 4 with $IC_{50}$ values of 298 pM and 214 pM, respectively. Using these same constant concentrations of ligands, no inhibition of either GDF8 or GDF11 was observed by the activin A antibodies, H4H10446P2 and H4H10430P, when tested at up to 100 nM of the antibodies. On a separate day, the activin A antibodies H4H10429P and H4H10436P2 were tested for inhibition in this assay in the presence of constant concentrations of 250 pM GDF8 or 250 pM GDF11, and no inhibition was observed after incubation of the cells with up to 150 nM of the tested activin A antibodies; GDF8 and GDF11 alone in this assay exhibited EC50 values of 124 pM and 166 pM, respectively. These data demonstrate that the Activin A antibodies H4H10446P2, H4H10430P, H4H10429P and H4H10436P2 do not functionally inhibit GDF8 or GDF11.

Example 7

Stimulation of Skeletal Muscle Hypertrophy Using Activin A Antibodies

Skeletal muscle hypertrophy induced by administration of a myostatin-specific antagonist, the anti-GDF8 antibody H4H1657N2 (see US 2011-0293630 A1, hereby incorporated by reference in its entirety), or a combination of H4H1657N2 and different anti-Activin A antibodies, was evaluated in CB17 SCID mice. The extent of hypertrophy was measured relative to treatment with an isotype-matched control antibody. Also included in these studies was treatment with the extracellular domain of human ActRIIB, produced with a C-terminal human IgG1 Fc domain (Control 4, SEQ ID No: 227). Control 4 has been previously shown to induce muscle hypertrophy in vivo and also to bind and block the activity of multiple TGF-beta family member ligands (Souza, T A et al. Mol Endocrinol 22:2689-702 (2008); Lee, S J et al. Proc Natl Acad Sci U.S.A. 102(50): 18117-22 (2005)).

A total of eight anti-Activin A antibodies of the invention and Control 1 were tested in combination with H4H1657N2 or alone in eight studies, in comparison to isotype control, Control 4, H4H1657N2 alone, or Control 2 (an anti-Activin RIIB antibody having VH/VL of the antibody MOR08159 described in US 2010/0272734 A1) treatment groups. For the studies, male CB17 SCID mice (Taconic, #CB17SC-M) of approximately 10 weeks of age were divided evenly according to body weight into 6 groups of 5 mice. Groups of mice were treated in each study as described in Table 13.

TABLE 13

Antibodies and controls tested in in vivo muscle hypertrophy studies

| Study # | Samples Tested | Dosage 1 | Dosing interval of dosage 1 | Dosage 2 | Dosing interval of dosage 2 |
|---|---|---|---|---|---|
| 1 | Isotype Control | 10 mg/kg | days 0, 3, and 7 | 8 mg/kg | day 14 |
|  | H4H1657N2 | 10 mg/kg | days 0, 3, and 7 | 8 mg/kg | day 14 |
|  | Control 4 | 10 mg/kg | days 0, 3, and 7 | 8 mg/kg | day 14 |
|  | H4H10423P + H4H1657N2 | 10 mg/kg + 10 mg/kg | days 0, 3, and 7 | 8 mg/kg + 8 mg/kg | day 14 |
|  | H4H10432P2 + H4H1657N2 | 10 mg/kg + 10 mg/kg | days 0, 3, and 7 | 8 mg/kg + 8 mg/kg | day 14 |
|  | H4H10442P2 + H4H1657N2 | 10 mg/kg + 10 mg/kg | days 0, 3, and 7 | 8 mg/kg + 8 mg/kg | day 14 |
| 2 | Isotype Control | 10 mg/kg | days 0, 3, and 7 | 8 mg/kg | day 14 |
|  | H4H1657N2 | 10 mg/kg | days 0, 3, and 7 | 8 mg/kg | day 14 |
|  | Control 4 | 10 mg/kg | days 0, 3, and 7 | 8 mg/kg | day 14 |
|  | H4H10429P + H4H1657N2 | 10 mg/kg + 10 mg/kg | days 0, 3, and 7 | 8 mg/kg + 8 mg/kg | day 14 |
|  | H4H10436P2 + H4H1657N2 | 10 mg/kg + 10 mg/kg | days 0, 3, and 7 | 8 mg/kg + 8 mg/kg | day 14 |
|  | H4H10440P2 + H4H1657N2 | 10 mg/kg + 10 mg/kg | days 0, 3, and 7 | 8 mg/kg + 8 mg/kg | day 14 |
| 3 | Isotype Control | 10 mg/kg | days 0, 3, 7, and 14 | N/A |  |
|  | H4H1657N2 | 10 mg/kg | days 0, 3, 7, and 14 |  |  |
|  | Control 4 | 10 mg/kg | days 0, 3, 7, and 14 |  |  |
|  | H4H10446P2 + H4H1657N2 | 10 mg/kg + 10 mg/kg | days 0, 3, 7, and 14 |  |  |
|  | H4H10430P + H4H1657N2 | 10 mg/kg + 10 mg/kg | days 0, 3, 7, and 14 |  |  |
| 4 | Isotype Control | 25 mg/kg | days 0, 3, 7, and 14 | N/A |  |
|  | H4H1657N2 | 10 mg/kg | days 0, 3, 7, and 14 |  |  |
|  | H4H10430P | 10 mg/kg | days 0, 3, 7, and 14 |  |  |
|  | H4H10430P + H4H1657N2 | 2 mg/kg + 10 mg/kg | days 0, 3, 7, and 14 |  |  |
|  | H4H10430P + H4H1657N2 | 10 mg/kg + 10 mg/kg | days 0, 3, 7, and 14 |  |  |
|  | H4H10430P + H4H1657N2 | 25 mg/kg + 10 mg/kg | days 0, 3, 7, and 14 |  |  |
| 5 | Isotype Control | 25 mg/kg | days 0, 3, 7, and 14 | N/A |  |
|  | H4H1657N2 | 10 mg/kg | days 0, 3, 7, and 14 |  |  |
|  | H4H10446P2 | 10 mg/kg | days 0, 3, 7, and 14 |  |  |
|  | H4H10446P2 + H4H1657N2 | 2 mg/kg + 10 mg/kg | days 0, 3, 7, and 14 |  |  |
|  | H4H10446P2 + H4H1657N2 | 10 mg/kg + 10 mg/kg | days 0, 3, 7, and 14 |  |  |
|  | H4H10446P2 + H4H1657N2 | 25 mg/kg + 10 mg/kg | days 0, 3, 7, and 14 |  |  |
| 6 | Isotype Control | 10 mg/kg | days 0, 3, 7, 14, and 21 | N/A |  |
|  | H4H1657N2 | 10 mg/kg | days 0, 3, 7, 14, and 21 |  |  |
|  | Control 4 | 10 mg/kg | days 0, 3, 7, 14, and 21 |  |  |
|  | Control 1 | 10 mg/kg | days 0, 3, 7, 14, and 21 |  |  |
|  | Control 1 + H4H1657N2 | 10 mg/kg + 10 mg/kg | days 0, 3, 7, 14, and 21 |  |  |
| 7 | Isotype Control | 10 mg/kg | days 0, 3, 7, and 14 | N/A |  |
|  | Control 4 | 10 mg/kg | days 0, 3, 7, and 14 |  |  |
|  | Control 2 | 25 mg/kg | days 0, 3, 7, and 14 |  |  |
|  | H4H10430P + H4H1657N2 | 10 mg/kg + 10 mg/kg | days 0, 3, 7, and 14 |  |  |
|  | H4H10446P2 + H4H1657N2 | 10 mg/kg + 10 mg/kg | days 0, 3, 7, and 14 |  |  |
| 8 | Isotype Control | 25 mg/kg | days 0, 3, 7, and 14 | N/A |  |
|  | H4H1657N2 | 10 mg/kg | days 0, 3, 7, and 14 |  |  |
|  | Control 4 | 25 mg/kg | days 0, 3, 7, and 14 |  |  |
|  | Control 2 | 25 mg/kg | days 0, 3, 7, and 14 |  |  |
|  | H4H10423P + H4H1657N2 | 25 mg/kg + 10 mg/kg | days 0, 3, 7, and 14 |  |  |
|  | H4H10430P + H4H1657N2 | 25 mg/kg + 10 mg/kg | days 0, 3, 7, and 14 |  |  |

For studies 1-5, 7, and 8, antibodies and Control 4 were administered subcutaneously at a dose of 10 mg/kg of each protein twice during the first week of the experiment (days 0 and 3) and once at a dose of 10 mg/kg of each protein during the second week (day 7). A final dose of antibody or Control 4 during the third week (day 14) was administered subcutaneously at 8 mg/kg for studies #1 and #2 or at 10 mg/kg for studies #3-#8 (Table 13). On day 21, mice were euthanized and total body weight for each mouse was measured. For study 6, antibodies were administered for previous studies 1-5 but the treatment was extended to day 28 with an additional injection at day 21. The tibialis anterior (TA) and gastrocnemius (GA) muscles from each mouse were dissected and weighed. Tissue weights were normalized to the starting body weight, and the mean percent change in weight over the mean weight of the isotype control antibody treatment group was calculated. Results summarized in Tables 14-21 are expressed as mean percent increase over isotype control±standard error of the mean.

As shown in Table 15, in the second study, Control 4 induced hypertrophy in all muscles examined, with increases of 43.47±2.37% in average TA weight and 29.24±2.22% in GA average muscle weight as compared with the isotype control treated mice. In this study, treatment with H4H1657N2 alone also induced increases in TA and GA average muscle weights (16.7±2.73% and 18.54±3.48%, respectively) as compared with the isotype control treated mice, but these average increases were less than those observed for the Control 4 treatment group. The combination treatments H4H1657N2/H4H10429P and H4H1657N2/H4H10436P2 induced increases in average TA (34.14±2.55% and 29.31±1.59%, respectively) and average GA (26.24±3.11% and 26.55±2.41%, respectively), increases that were between the increases observed for either H4H1657N2 or Control 4 alone. The combination H4H1657N2/H4H10440P2 did not induce increases in TA or GA average weights as great as those induced by the other two combinations in this study or by the Control 4 treatment.

TABLE 14

Percent change in body and muscle weights compared to isotype control treatment, Study 1

|  | Isotype Control | H4H1657N2 | Control 4 | H4H10423P + H4H1657N2 | H4H10432P2 + H4H1657N2 | H4H10442P2 + H4H1657N2 |
|---|---|---|---|---|---|---|
| Dose | 10 mg/kg | 10 mg/kg | 10 mg/kg | 10 mg/kg + 10 mg/kg | 10 mg/kg + 10 mg/kg | 10 mg/kg + 10 mg/kg |
| Body Weight | 0.00 ± 0.91 | 10.99 ± 0.48 | 18.45 ± 0.89 | 13.36 ± 1.10 | 12.84 ± 0.98 | 12.09 ± 0.78 |
| TA Muscle | 0.00 ± 1.15 | 19.54 ± 2.67 | 45.80 ± 1.47 | 32.03 ± 2.12 | 24.83 ± 2.95 | 40.76 ± 2.59 |
| GA Muscle | 0.00 ± 0.89 | 26.46 ± 3.63 | 31.91 ± 1.40 | 27.58 ± 1.61 | 26.39 ± 1.87 | 30.62 ± 2.32 |

As shown in Table 14, in the first study, Control 4 induced significant hypertrophy in all muscles examined, with increases of 45.80±1.47% in TA, and 31.91±1.4% in GA weights as compared to the isotype control treated mice. Treatment with H4H1657N2 alone also induced hypertrophy in TA (19.54±2.67% increase) and GA (26.46±3.63% increase) muscle weights, but it was less efficacious than Control 4. The combination of H4H1657N2+H4H10442P2 induced similar increases in average TA (40.76±2.59%) and GA (30.62±2.32%) muscle weights as compared to mice treated with Control 4. The combination treatments H4H1657N2/H4H10423P and H4H1657N2/H4H10432P2 did not induce increases in average TA weights as great as those induced by the H4H16757N2/H4H10442P or the Control 4 treatments.

TABLE 15

Percent change in body and muscle weights compared to isotype control treatment, Study 2

|  | Isotype Control | H4H1657N2 | Control 4 | H4H10429P + H4H1657N2 | H4H10436P2 + H4H1657N2 | H4H10440P2 + H4H1657N2 |
|---|---|---|---|---|---|---|
| Dose | 10 mg/kg | 10 mg/kg | 10 mg/kg | 10 mg/kg + 10 mg/kg | 10 mg/kg + 10 mg/kg | 10 mg/kg + 10 mg/kg |
| Body Weight | 0.00 ± 2.53 | 4.12 ± 2.19 | 11.22 ± 1.71 | 7.17 ± 1.57 | 7.89 ± 0.37 | 1.89 ± 1.39 |
| TA Muscle | 0.00 ± 3.59 | 16.70 ± 2.73 | 43.47 ± 2.37 | 34.14 ± 2.55 | 29.31 ± 1.59 | 14.55 ± 2.22 |
| GA Muscle | 0.00 ± 3.54 | 18.54 ± 3.48 | 29.24 ± 2.22 | 26.24 ± 3.11 | 26.55 ± 2.41 | 15.65 ± 2.66 |

TABLE 16

Percent change in body and muscle weights compared to isotype control treatment, Study 3

|  | Isotype Control | H4H1657N2 | Control 4 | H4H10446P2 + H4H1657N2 | H4H10430P + H4H1657N2 |
|---|---|---|---|---|---|
| Dose | 10 mg/kg | 10 mg/kg | 10 mg/kg | 10 mg/kg + 10 mg/kg | 10 mg/kg + 10 mg/kg |
| Body Weight | 0.00 ± 2.00 | 1.43 ± 1.14 | 18.92 ± 3.53 | 10.90 ± 2.51 | 8.88 ± 1.58 |
| TA Muscle | 0.00 ± 2.13 | 14.19 ± 3.19 | 39.90 ± 3.58 | 40.01 ± 3.67 | 28.30 ± 3.27 |
| GA Muscle | 0.00 ± 1.62 | 15.73 ± 0.58 | 34.01 ± 2.87 | 31.29 ± 2.60 | 21.55 ± 2.30 |

As shown in Table 16, in the third study, Control 4 induced hypertrophy in all muscles examined, with increases of 39.90±3.58% in average TA muscle weight, and 34.01±2.87% in average GA muscle weight as compared with the isotype control-treated mice. Treatment with H4H1657N2 alone also induced increases in TA (14.19±3.19%) and GA average muscle weight (15.73±0.58%) as compared with the isotype control treated mice, but these average increases were less than those observed for the Control 4 treatment group. The combination treatment H4H1657N2/H4H10446P2 induced similar increases in TA (40.01±3.67%) and GA (31.29±2.60%) average muscle weights as for mice treated with Control 4. The combination treatment with H4H1657N2/H4H10430P induced increases in TA (28.30±3.27%) and GA (21.55±2.30%) average muscle weights that were between those observed for H4H1657N2 alone and the H4H1657N2/H4H10446P2 combination treatment.

were not statistically significant. The combination treatment of H4H1657N2 and H4H10430P at 10 mg/kg and 2 mg/kg, respectively, induced increases in TA (39.02±3.55%) and GA (27.57±1.26%) average muscle weights that were greater in TA muscle than those observed for H4H1657N2 or H4H10430P alone. The combination treatment of H4H1657N2 and H4H10430P at 10 mg/kg and 10 mg/kg, respectively, induced increases in TA (40.20±2.48%) and GA (22.46±5.03%) average muscle weights that were greater in TA muscle than those observed for H4H1657N2 or H4H10430P alone. The combination treatment of H4H1657N2 and H4H10430P at 10 mg/kg and 25 mg/kg, respectively, induced increases in TA (44.92±5.70%) and GA (30.22±2.97%) average muscle weights that were greater in TA muscle than those observed for H4H1657N2 or H4H10430P alone.

TABLE 17

Percent change in body and muscle weights compared to isotype control treatment, Study 4

|  | Isotype Control | H4H1657N2 | H4H10430P | H4H10430P + H4H1657N2 | H4H10430P + H4H1657N2 | H4H10430P + H4H1657N2 |
|---|---|---|---|---|---|---|
| Dose | 25 mg/kg | 10 mg/kg | 10 mg/kg | 2 mg/kg + 10 mg/kg | 10 mg/kg + 10 mg/kg | 25 mg/kg + 10 mg/kg |
| Body Weight | 0.00 ± 0.57 | 9.89 ± 0.98 | 4.20 ± 1.00 | 14.53 ± 0.80 | 12.61 ± 1.81 | 13.78 ± 1.58 |
| TA Muscle | 0.00 ± 3.04 | 21.05 ± 2.64 | 7.83 ± 2.74 | 39.02 ± 3.55 | 40.20 ± 2.48 | 44.92 ± 5.70 |
| GA Muscle | 0.00 ± 2.71 | 22.85 ± 2.28 | 8.86 ± 1.24 | 27.57 ± 1.26 | 22.46 ± 5.03 | 30.22 ± 2.97 |

As shown in Table 17, in the fourth study, H4H1657N2 induced hypertrophy in the muscles examined, with increase of 21.05±2.64% in average TA muscle weight and 22.85±2.28% in average GA muscle weight as compared with the isotype control treated mice. In this study, treatment with H4H10430P alone slightly increased muscle weights as compared to the isotype control treated mice but the values

TABLE 18

Percent change in body and muscle weights compared to isotype control treatment, Study 5

|  | Isotype Control | H4H1657N2 | H4H10446P2 | H4H10446P2 + H4H1657N2 | H4H10446P2 + H4H1657N2 | H4H10446P2 + H4H1657N2 |
|---|---|---|---|---|---|---|
| Dose | 25 mg/kg | 10 mg/kg | 10 mg/kg | 2 mg/kg + 10 mg/kg | 10 mg/kg + 10 mg/kg | 25 mg/kg + 10 mg/kg |
| Body Weight | 0.00 ± 1.23 | 10.94 ± 1.03 | 0.29 ± 1.33 | 14.26 ± 1.45 | 12.61 ± 1.26 | 16.31 ± 2.04 |
| TA Muscle | 0.00 ± 2.20 | 25.40 ± 1.35 | 3.70 ± 1.67 | 51.29 ± 4.20 | 49.64 ± 4.08 | 49.79 ± 5.46 |
| GA Muscle | 0.00 ± 2.92 | 22.82 ± 1.97 | 2.70 ± 1.06 | 39.24 ± 3.08 | 35.56 ± 3.39 | 35.14 ± 3.49 |

As shown in Table 18, in the fifth study, H4H1657N2 induced hypertrophy in the muscles examined, with increase of 25.4±1.35% in average TA muscle weight and 22.82±1.97% in average GA muscle weight as compared with the isotype control treated mice. In this study, treatment with H4H10446P2 alone induced a low level of muscle hypertrophy with increase of 3.70±1.67% in average TA muscle weight and 2.70±1.06% in average GA muscle weight as compared with the isotype control treated mice. The combination treatment of H4H1657N2 and H4H10446P2 at 10 mg/kg and 2 mg/kg, respectively, induced increases in TA (51.29±4.20%) and GA (39.24±3.08%) average muscle weights that were greater than those observed for H4H1657N2 or H4H10446P2 alone. The combination treatment of H4H1657N2 and H4H10446P2, each at a 10 mg/kg dose, induced increases in TA (49.64±4.08%) and GA (35.56±3.39%) average muscle weights that were greater than those observed for H4H1657N2 or H4H10446P2 alone. The combination treatment of H4H1657N2 and H4H10446P2 at 10 mg/kg and 25 mg/kg, respectively, induced increases in TA (49.79±5.46%) and GA (35.14±3.49%) average muscle weights that were greater than those observed for H4H1657N2 or H4H10446P2 alone.

As shown in Table 20, in the seventh study, Control 4-induced hypertrophy in all muscles examined, with increases of 34.43±5.92% in average TA weight and 14.86±3.65% in GA average muscle weight as compared with the isotype control treated mice. In this study, treatment with Control 2 alone induced hypertrophy in the muscles examined, with increases of 36.75±3.88% in average TA weight and 26.41±3.16% in GA average muscle weight as compared with the isotype control treated mice. The combination treatment H4H1657N2 and H4H10430P at 10 mg/kg and 10 mg/kg, respectively, induced increases in TA (33.13±2.02%) and GA (22.82±1.34%) average muscle weights that were between increases observed for ActRIIB-Fc alone and Control 2 alone. The combination treatment H4H1657N2 and H4H10446P2 at 10 mg/kg and 10 mg/kg, respectively, induced increases in TA (41.28±2.76%) and GA (29.21±2.62%) average muscle weights.

TABLE 19

Percent change in body and muscle weights compared to isotype control treatment, Study 6

|  | Isotype Control | Control 4 | H4H1657N2 | Control 1 | Control 1 1 + H4H1657N2 |
|---|---|---|---|---|---|
| Dose | 10 mg/kg | 10 mg/kg | 10 mg/kg | 10 mg/kg | 10 mg/kg + 10 mg/kg |
| Body Weight | 0.00 ± 0.51 | 17.04 ± 2.90 | 8.92 ± 1.26 | 3.52 ± 0.86 | 15.84 ± 0.75 |
| TA Muscle | 0.00 ± 2.15 | 47.34 ± 2.63 | 17.21 ± 2.97 | 4.54 ± 2.25 | 30.06 ± 5.51 |
| GA Muscle | 0.00 ± 1.71 | 32.17 ± 3.81 | 21.57 ± 1.90 | 2.72 ± 1.30 | 30.72 ± 3.64 |

As shown in Table 19, in the sixth study, Control 4 induced hypertrophy in all muscles examined, with increases of 47.34±2.63% in average TA weight and 32.17±3.81% in GA average muscle weight as compared with the isotype control treated mice. In this study, treatment with H4H1657N2 alone also induced increases in TA and GA average muscle weights 17.21±2.97% and 21.57±1.90%, respectively, as compared with the isotype control treated mice, but these average increases were less than those observed for the Control 4 treatment group. In this study, treatment with Control 1 alone induced a low level of muscle hypertrophy with increase of 4.54±2.25% in average TA muscle weight and 2.72+1.30% in average GA muscle weight as compared with the isotype control treated mice. The combination treatment of H4H1657N2 and Control 1 at 10 mg/kg and 10 mg/kg, respectively, induced increases in TA (30.06±5.51%) and GA (30.72±3.64%) average muscle weights that were greater than those observed for H4H1657N2 or Control 1 alone.

TABLE 20

Percent change in body and muscle weights compared to isotype control treatment, Study 7

|  | Isotype Control | Control 4 | Control2 | H4H10430P + H4H1657N2 | H4H10446P2 + H4H1657N2 |
|---|---|---|---|---|---|
| Dose | 10 mg/kg | 10 mg/kg | 25 mg/kg | 10 mg/kg + 10 mg/kg | 10 mg/kg + 10 mg/kg |
| Body Weight | 0.00 ± 0.90 | 8.17 ± 3.30 | 19.18 ± 1.75 | 10.55 ± 1.48 | 11.67 ± 0.98 |
| TA Muscle | 0.00 ± 2.30 | 34.43 ± 5.92 | 36.75 ± 3.88 | 33.13 ± 2.02 | 41.28 ± 2.76 |
| GA Muscle | 0.00 ± 2.01 | 14.86 ± 3.65 | 26.41 ± 3.16 | 22.82 ± 1.34 | 29.21 ± 2.62 |

TABLE 21

Percent change in body and muscle weights compared to isotype control treatment, Study 8

|  | Isotype Control | Control 4 | H4H1657N2 | Control 2 | H4H10423P + H4H1657N2 | H4H10430P + H4H1657N2 |
|---|---|---|---|---|---|---|
| Dose | 25 mg/kg | 25 mg/kg | 10 mg/kg | 25 mg/kg | 25 mg/kg + 10 mg/kg | 25 mg/kg + 10 mg/kg |
| Body Weight | 0.00 ± 0.64 | 19.81 ± 0.90 | 8.64 ± 1.30 | 21.56 ± 1.29 | 10.45 ± 1.40 | 15.45 ± 1.18 |
| TA Muscle | 0.00 ± 2.72 | 53.74 ± 5.31 | 18.44 ± 2.30 | 39.90 ± 1.69 | 36.33 ± 3.67 | 43.83 ± 1.56 |
| GA Muscle | 0.00 ± 0.76 | 39.39 ± 4.56 | 21.17 ± 1.72 | 25.87 ± 2.72 | 28.18 ± 3.11 | 31.24 ± 1.90 |

As shown in Table 21, in the eighth study, Control 4 induced hypertrophy in all muscles examined, with increases of 53.74±5.31% in average TA weight and 39.39±4.56% in GA average muscle weight as compared with the isotype control treated mice. In this study, treatment with H4H1657N2 alone also induced increases in TA and GA average muscle weights of 18.44±2.30% and 21.17±1.72%, respectively, as compared with the isotype control treated mice, but these average increases were less than those observed for the Control 4 treatment group. In this study, treatment with Control 2 alone induced hypertrophy in the muscles examined, with increases of 39.90±1.69% in average TA weight and 25.87±2.72% in GA average muscle weight as compared with the isotype control treated mice. The combination treatment H4H1657N2 and H4H10423P at 10 mg/kg and 25 mg/kg, respectively, induced increases in TA (36.33±3.67%) and GA (28.18±3.11%) average muscle weights as compared with the isotype control treated mice. The combination treatment H4H1657N2 and H4H10430P at 10 mg/kg and 25 mg/kg, respectively, induced increases in TA (43.83±1.56%) and GA (31.24±1.90%) average muscle weights that were between increases observed for Control 4 alone and Control 2 alone.

These studies show that administration of anti-Activin A antibodies with a myostatin inhibitor can further increase skeletal muscle hypertrophy to a significantly greater degree than treatment with a myostatin inhibitor alone at the doses and injection frequencies tested.

Example 8

Blocking of Activin A Binding Using Activin A Antibodies

The ability of selected anti-Activin A antibodies to block the interaction of Activin A with its receptors, ActRIIB and ActRIIA, as well as its endogenous antagonist, Follistatin, was determined using a Biacore 3000 instrument. For this experiment, Control 4 (human ActRIIB expressed with a C-terminal human Fc tag (SEQ ID:227)), human ActRIIA expressed with a C-terminal human Fc tag (hActRIIA-Fc; R&D Systems, #340-R2-100), or Follistatin-288 (R&D Systems, #5836-FS-025) were amine-coupled to a Biacore CM5 sensor surface. Activin A (R&D Systems, #338-AC) at a fixed concentration of 5 nM either alone or mixed with Activin A antibodies, hActRIIA-Fc, hActRIIB-Fc, or isotype control antibody at a final concentration of 60 nM (12-fold molar excess over Activin A) was incubated at room temperature for 1 hour. The antibody-Activin A mixtures were then injected over the amine-coupled Control 4, hActRIIA-Fc, or Follistatin-288 surfaces at a flow rate of 20 uL/min. The binding signal (RU) was measured at 150 seconds after the start of the injection, and this signal was subtracted by the measured RU value for a negative control reference surface to determine the specific binding signal. The percentage of free Activin A binding over the receptor or antagonist surfaces in the presence of each anti-Activin A antibody was calculated as the ratio of the observed specific binding signal divided by the specific binding signal from 5 nM Activin A in the presence of no antibody.

TABLE 22

Blocking of Activin A Binding to Follistatin by anti-Activin A Antibodies

| mAb/protein concentration (nM) | Follistatin-288 surface (3000RU captured)-Normalized to Activin A (% bound RU w/no inhibitor) | | | | | |
|---|---|---|---|---|---|---|
| | H4H10442P2 | H4H10446P2 | H4H10430P | H4H10440P2 | H4H10429P | H4H10436P2 |
| 0 | 100 | 100 | 100 | 100 | 100 | 100 |
| 0.94 | 73 | 77 | 79 | 76 | 97 | 78 |
| 1.88 | 46 | 54 | 59 | 57 | 80 | 61 |
| 3.75 | 6 | 7 | 15 | 17 | 20 | 16 |
| 7.5 | 3 | 3 | 1 | 4 | 1 | 1 |
| 15 | 3 | 3 | 1 | 2 | 1 | 1 |
| 30 | 3 | 3 | 1 | 1 | 2 | 2 |
| 60 | 3 | 3 | 1 | 0 | 3 | 2 |

| mAb/protein concentration (nM) | Follistatin-288 surface (3000RU captured)-Normalized to Activin A (% bound RU w/no inhibitor) | | | | | |
|---|---|---|---|---|---|---|
| | H4H10423P | Control 1 | Control 3 | hActRIIA-hFc | Control 4 (hActRIIB-hFc) | isotype (—) control |
| 0 | 100 | 100 | 100 | 100 | 100 | 100 |
| 0.94 | 120 | 83 | 172 | 156 | 169 | 100 |
| 1.88 | 122 | 68 | 170 | 148 | 163 | 102 |
| 3.75 | 103 | 27 | 145 | 138 | 151 | 97 |
| 7.5 | 97 | 0 | 33 | 116 | 120 | 102 |
| 15 | 96 | 1 | 5 | 60 | 43 | 102 |

TABLE 22-continued

Blocking of Activin A Binding to Follistatin by anti-Activin A Antibodies

| 30 | 94 | 1 | 7 | 11 | 1 | 104 |
| 60 | 93 | 2 | 9 | 13 | 1 | 103 |

As shown in Table 22, 6 of the 7 anti-Activin A antibodies of the invention tested and both Control 1 and Control 3 blocked the binding of Actin A to Follistatin-288. One antibody of the invention, H4H10423P, did not prevent binding of Activin A to Follistatin-288. Control 4 and hActRIIA-Fc blocked the binding of Activin A to Follistatin-288 at higher concentrations.

blocked the binding of hActRIIA-Fc to Activin A. Three antibodies of the invention, H4H10442P2, H4H10446P2, and H4H10423P, did not prevent binding of Activin A to hActRIIA-Fc. Control 4 and hActRIIA-Fc blocked the binding of Activin A to hActRIIA-Fc.

TABLE 23

Blocking of Activin A Binding to hActRIIA-Fc by anti-Activin A Antibodies

| g mAb/protein concentration (nM) | hActRIIA-hFc surface (8000RU captured)-Normalized to Activin A (% bound RU w/no inhibitor) | | | | | |
|---|---|---|---|---|---|---|
| | H4H10442P2 | H4H10446P2 | H4H10430P | H4H10440P2 | H4H10429P | H4H10436P2 |
| 0.00 | 100 | 100 | 100 | 100 | 100 | 100 |
| 0.94 | 114 | 111 | 81 | 75 | 87 | 75 |
| 1.88 | 114 | 115 | 62 | 52 | 66 | 55 |
| 3.75 | 95 | 85 | 19 | 17 | 19 | 16 |
| 7.50 | 105 | 94 | 3 | 6 | 1 | 2 |
| 15 | 113 | 108 | 2 | 4 | 1 | 2 |
| 30 | 117 | 98 | 2 | 3 | 1 | 2 |
| 60 | 118 | 118 | 2 | 3 | 1 | 2 |

| g mAb/protein concentration (nM) | hActRIIA-hFc surface (8000RU captured)-Normalized to Activin A (% bound RU w/no inhibitor) | | | | | |
|---|---|---|---|---|---|---|
| | H4H10423P | Control 1 | Control 3 | hActRIIA-hFc | Control 4 (hActRIIB-hFc) | isotype (—) control |
| 0.00 | 100 | 100 | 100 | 100 | 100 | 100 |
| 0.94 | 112 | 82 | 207 | 236 | 276 | 109 |
| 1.88 | 114 | 66 | 190 | 222 | 266 | 112 |
| 3.75 | 111 | 28 | 139 | 188 | 231 | 110 |
| 7.50 | 110 | 1 | 32 | 128 | 160 | 115 |
| 15 | 112 | 1 | 1 | 50 | 51 | 116 |
| 30 | 114 | 1 | 1 | 5 | 2 | 118 |
| 60 | 116 | 2 | 0 | 3 | 1 | 119 |

As shown in Table 23, 4 of the 7 anti-Activin A antibodies of the invention tested and both Control 1 and Control 3

TABLE 24

Blocking of Activin A Binding to hActRIIB-Fc by anti-Activin A Antibodies

| mAb/protein concentration (nM) | hActRIIB-hFc (Control 4) surface (4000RU captured)-Normalized to Activin A (% bound RU w/no inhibitor) | | | | | |
|---|---|---|---|---|---|---|
| | H4H10442P2 | H4H10446P2 | H4H10430P | H4H10440P2 | H4H10429P | H4H10436P2 |
| 0.00 | 100 | 100 | 100 | 100 | 100 | 100 |
| 0.94 | 110 | 107 | 80 | 79 | 87 | 80 |
| 1.88 | 106 | 105 | 62 | 58 | 67 | 60 |
| 3.75 | 88 | 76 | 20 | 19 | 19 | 19 |
| 7.50 | 103 | 95 | 4 | 7 | 2 | 3 |
| 15 | 115 | 115 | 3 | 4 | 2 | 2 |
| 30 | 122 | 89 | 3 | 4 | 2 | 3 |
| 60 | 124 | 129 | 3 | 4 | 3 | 4 |

| mAb/protein concentration (nM) | hActRIIB-hFc (Control 4) surface (4000RU captured)-Normalized to Activin A (% bound RU w/no inhibitor) | | | | | |
|---|---|---|---|---|---|---|
| | H4H10423P | Control 1 | Control 3 | hActRIIA-hFc | Control 4 (hActRIIB-hFc) | isotype (—) control |
| 0.00 | 100 | 100 | 100 | 100 | 100 | 100 |
| 0.94 | 93 | 85 | 135 | 131 | 149 | 105 |

TABLE 24-continued

Blocking of Activin A Binding to hActRIIB-Fc by anti-Activin A Antibodies

| 1.88 | 78 | 69 | 133 | 129 | 148 | 105 |
| 3.75 | 47 | 31 | 120 | 127 | 144 | 104 |
| 7.50 | 42 | 2  | 33  | 113 | 130 | 107 |
| 15   | 42 | 2  | 2   | 56  | 51  | 110 |
| 30   | 41 | 2  | 1   | 5   | 3   | 111 |
| 60   | 41 | 3  | 2   | 5   | 2   | 115 |

As shown in Table 24, 4 of the 7 anti-Activin A antibodies of the invention tested and both Control 1 and Control 3 blocked the binding of Activin A to hActRIIB-Fc. Two antibodies of the invention, H4H10442P2 and H4H10446P2, did not prevent binding of Activin A to hActRIIB-Fc. One antibody of the invention, H4H10423P, demonstrated the ability to partial block the binding of Activin A to hActRIIB-Fc at higher concentrations of antibody tested. Both hActRIIB-Fc and hActRIIA-Fc blocked the binding of Activin A to hActRIIB-Fc.

Example 9

Effects of H4H1657N2 on Muscle Mass and Exercise Performance

The effects of the anti-GDF8 antibody H4H1657N2 on muscle mass and exercise performance was evaluated in aged male C57BL/6 mice (19 months old).

Mice were randomized into four groups (n=6-8/group), a sedentary or exercise group receiving subcutaneous doses of H4H1657N2 or an isotype control antibody (10 mg/kg) twice weekly for 21 days (6 injections). Mice in the exercise group were placed on an exercise regimen involving one training session a day, consisting of 20 minutes on an Exer 6M treadmill (Columbus Instruments, Columbus, Ohio) at 10 m/min with a 5° incline, five days a week for three consecutive weeks. At the end of three weeks of treatment, endurance was measured in all four groups using a treadmill exhaustion test. The data were analyzed with two-way ANOVA followed by Tukey HSD test. Muscle weights were reported as normalized weights (i.e., muscle weights were normalized to the body weights measured at the start of the experiment). Results for quadriceps muscle are provided in Table 25 as average % change for each group (±standard error of the mean) compared to the isotype control antibody group.

TABLE 25

Quadracept Muscle Weight Change

|  | Isotype Control (Sedentary) | H4H1657N2 (Sedentary) | Isotype Control + Exercise | H4H1657N2 + Exercise |
| --- | --- | --- | --- | --- |
| Quad Weight | 0.00 ± 2.72 | 15.77 ± 2.73 | 9.85 ± 3.57 | 17.66 ± 3.24 |

% Change from isotype control.
Means ± SEM are shown.

As seen in Table 25, H4H1657N2 treatment resulted in significant increases in the mass of quadriceps muscles ($p<0.01$ significance over isotype control for both H4H1657N2 groups). Increases in hindlimb muscle group weights (TA, GA,) were seen in exercised (17.4%, 12.5%, respectively) and sedentary (14.1%, 11.6%, respectively) aged mice, compared with an isotype control antibody. A slight increase in muscle weight was observed between exercised and sedentary aged mice that received isotype control antibody, but it was not statistically significant (Table 25).

The effects of H4H1657N2 treatment on exercise endurance was also examined in 19 month old male C57BL/6 mice (Table 26).

TABLE 26

Endurance Testing

|  | Isotype Control (Sedentary) | H4H1657N2 (Sedentary) | Isotype Control + Exercise | H4H1657N2 + Exercise |
| --- | --- | --- | --- | --- |
| Time Ran until Exhaustion (min) | 27.94 ± 4.12 | 28.54 ± 6.10 | 50.26 ± 8.56 | 73.23 ± 4.68 |
| Distance Ran until Exhaustion (m) | 428.42 ± 71.91 | 535.99 ± 155.61 | 930.06 ± 179.78 | 1366.65 ± 95.91 |

In exercised aged mice, H4H1657N2 also induced significant increases in endurance, as measured by treadmill running time (73.2 min versus 50.2 min) and distance (1.33 km versus 0.93 km), compared with the isotype control group (Table 26). However, in sedentary mice, H4H1657N2 did not significantly increase endurance compared with the isotype control group.

As in the muscle weight study, H4H1657N2 induced significant increases in endurance, as measured by treadmill running time and distance, in the exercised mice only, but not in the sedentary mice. These results show that H4H1657N2 increases physical performance outcomes when combined with exercise training.

Example 10

Effects of H4H1657N2 on Skeletal Muscle Mass and Isometric Force in Mice

The ability of H4H1657N2 to induce skeletal muscle hypertrophy was assessed in vivo in 9 week old male C57BL/6 mice.

Repeated subcutaneous doses of H4H1657N2 or an isotype control antibody, at either 10 or 30 mg/kg, were administered twice weekly for 3 weeks (n=6). H4H1657N2 treatment for 21 days produced increases in body weight of 4.7±2.3% (n.s.) and 7.1±1.5% (n.s.), respectively, compared to mice receiving isotype control administered at equal doses. Individual muscle weights were increased as follows compared to isotype control (10 mg/kg & 30 mg/kg): Tibialis anterior (19.4±4.9% & 20.6±1.5%), Gastrocnemius: (14.9±2.9% & 25.3±1.9%*), and Quadriceps (17.7±3.6%* & 26.2±3.8%**). (All stats by One Way ANOVA with Tukey's post hoc test [* $p<0.05$;  $p<0.01$; * $p<0.001$; n.s.=not statistically different].)

The increase in Tibialis anterior (TA) muscle mass was accompanied by an increase in ex vivo isometric force, indicating the ability to maintain both muscle function and mass. Mice previously treated with repeated subcutaneous doses of H4H1657N2 or isotype control antibody (at 10 mg/kg administered twice weekly for 3 weeks, n=6 per group) were individually anesthetized and maintained under Isoflurane gas while the TA muscle was excised placed in a oxygenated lactated ringers bath constantly maintained at 25° C. The superior end of the TA was firmly tied to a submerged stanchion in the bath while the distal tendon was tied to 305C lever arm (Cambridge Systems). Optimal length was determined by slightly stretching the TA and then testing the force produced by a 1 Hz stimulation at a minimal voltage. TA muscles were repeatedly stretched and stimulated until there was a decline in force and then relaxed to the previous position. Voltage was then incrementally increased in a series of 1 HZ stimulations to achieve maximal force output. Once optimal length and voltage had been determined, TA muscles were stimulated for 400 milliseconds at increasing frequencies (40-100 Hz) to determine maximum tetanic force. TA muscles were given 2 minute rest periods between each tetanic stimulation.

TA muscles from mice treated with an isotype control antibody at 10 mg/kg and 30 mg/kg dose for 21 days generated an average peak tetanic force of 892.6±37 and 906.1±37.8, respectively. TA muscles from mice treated with H4H1657N2 generated an average peak tetanic force of 1041.3±31.7 and 1003.3±35.7 mN, respectively. These force values represent increase of 16.7%* (10 mg/kg) and 10.7% n.s (30 mg/kg) in average peak tetanic force compared to isotype control (FIG. 2A). The overall drug effect of H4H1657N2 treatment on peak tetanic force was statistically different from isotype control at both 10 mg/kg and 30 mg/kg doses (10 mg/kg dose shown in FIG. 2B). (FIG. 2A: statistical analysis by One Way ANOVA with Tukey's post hoc test [* $p<0.05$; n.s.=not statistically different]. FIG. 2B: statistical analysis by Two way ANOVA and Sidaks post hoc test [$p>0.0001$].)

Example 11

H4H1657N2 Improves the Recovery from Hind Limb Suspension (HLS)-Induced Atrophy The effect of H4H1657N2 on skeletal muscle mass during the recovery phase from 7 days of hindlimb suspension (HLS) induced atrophy was assessed in one-year old C57BL/6 male mice.

At day 0, eighteen mice were suspended by the tail so that both hind legs could not touch the ground for the duration of 7 days. Mice were housed in special cages with free access to food and water. Concurrently, one additional group of six mice was left in normal caging and served as a control (Non-HLS control). At day 7, the suspended mice were taken down and randomized by percentage of body weight lost during HLS into three groups (n=6 each). At day 7, the muscle weights from the Non-HLS control group and one HLS group (HLS group) were taken to assess the percentage of atrophy in response to HLS. The two remaining HLS groups (n=6 each) were allowed to recover for 8 days (i.e., day 7 through day 15 of the experiment) in normal caging and treated subcutaneously with 10 mg/kg doses of either H4H1657N2 or an isotype control on days 7 and 10 (i.e., after zero days and 3 days of recovery) (HLS+7Rec+H4H1657N2 and HLS+7rec+Isotype Control, respectively). At day 15 (i.e., after 8 days of recovery), muscle weights were taken to assess the percentage of recovery after HLS-induced atrophy.

Figure 3:
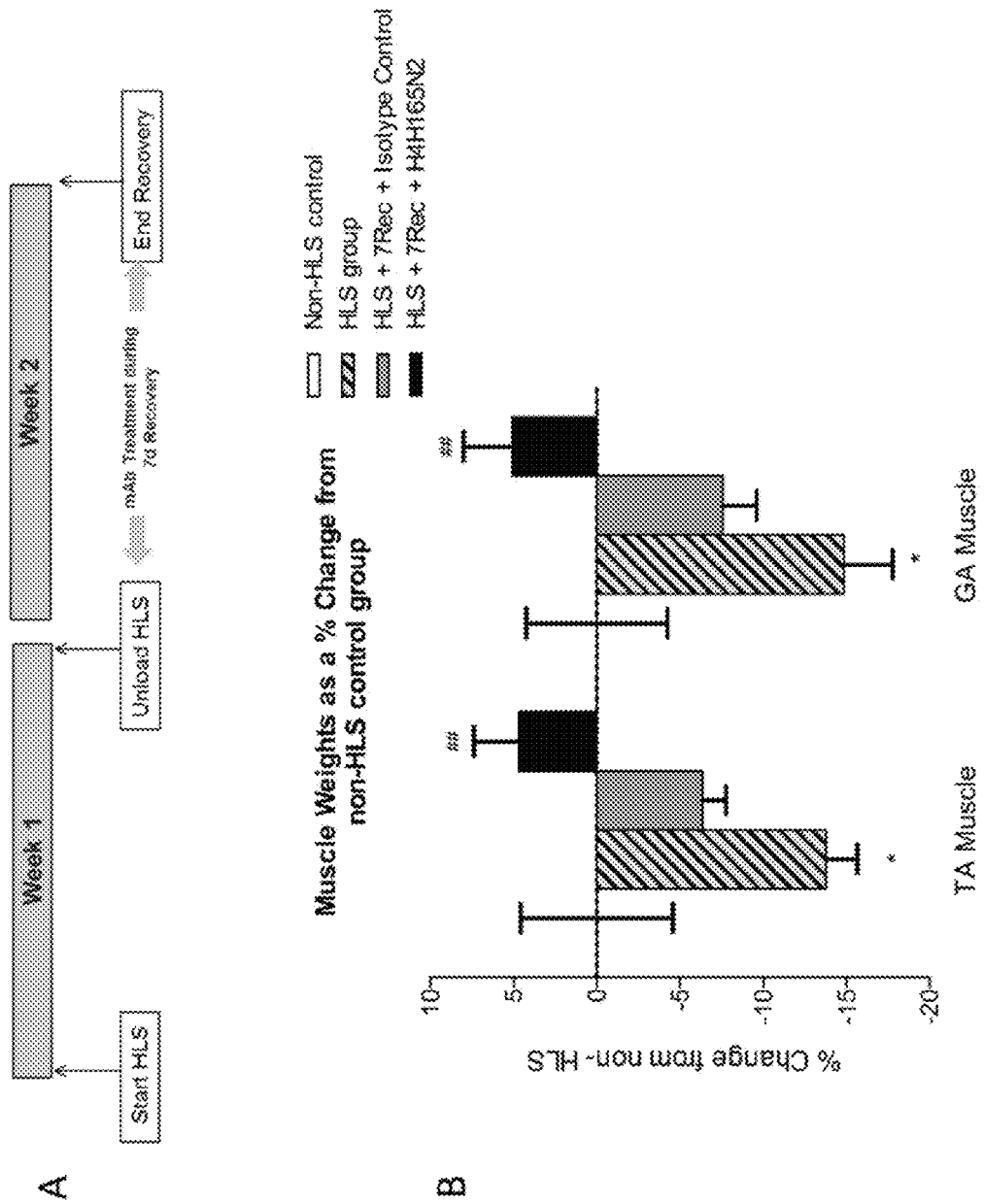
FIG. 3: Panel A shows the design of an experiment to evaluate the effects of H4H1657N2 during the recovery phase from hind limb suspension-induced muscle atrophy. Panel B shows the percentage change in TA and Gastrocnemius (GA) muscle weights for H4H1657N2-treated and isotype control antibody-treated mice post-recovery after 7 days of hind limb suspension (HLS+7Rec) versus mice without a recovery period after 7 days of hind limb suspension (HLS) and control mice (non-HLS control). Values are expressed as the mean percentage change over control non-HLS values±SEM. Data analyzed using one-way analysis of variance (ANOVA) followed by Tukey's test. *=p<0.05 significance over Non-HLS group. #=p<0.05 significance over HLS group.

As seen in FIG. 3B, seven days of HLS resulted in significant loss of mass in both tibialis anterior (TA) and gastrocnemius (GA) (HLS group), as compared to the Non-HLS control group (−13.7%* and −14.8%* respectively). After 8 days of recovery, the HLS+7rec+Isotype Control group maintained losses in TA and GA muscle mass (−6.3% and −7.5%) as compared to the Non-HLS control group, whereas the HLS+7Rec+H4H1657N2 group showed gains in mass (4.7% and 5%) as compared to the Non-HLS group.

When comparing the two recovery groups (i.e., HLS+7Rec+H4H1657N2 versus HLS+7rec+Isotype Control), the effects of H4H1657N2 on TA and GA mass were not statistically different from the effects seen with the isotype control antibody. However, while the HLS+7rec+Isotype Control group's muscle mass was not statistically different from the HLS group or the Non-HLS control group, the HLS+7Rec+H4H1657N2 group had statistically larger TA and GA mass when compared to the HLS group. (All stats by One Way ANOVA with Tukey's post hoc test [* $p<0.05$ vs. No HLS; ## $p<0.01$ vs. HLS.)

Example 12

Inhibition of BMP Receptor Type I and II Activation by Anti-Activin A Antibodies and ActRIIB-Fc Bone morphogenetic proteins (BMPs) belong to the TGF-β superfamily and are involved in regulation of many physiological processes by activating receptor complexes on the cell surface that are composed of BMP receptor types I and II. Activation of receptors leads to phosphorylation of SMAD proteins and transcriptional activation of ligand-responsive genes.

A bioassay was developed to detect the regulation of BMP signaling in W-20-17 cells, a mouse bone marrow stromal cell line previously shown to be responsive to BMP2. The cells were engineered to stably express a luciferase reporter (i.e., BMP-responsive element (BRE(2X)-luciferase-IRES-GFP)), and sorted for high expression of GFP. The resultant stable cell line is referred to as W-20-17/BRE-luc and was maintained in 10% FBS, DMEM, Pen/Strep, and 200 μg/ml G418. These cells were used to measure BMP activation and the inhibition of this activation by anti-Activin A antibodies and ActRIIB-hFc (Control 4, SEQ ID No:227).

The ability of four anti-Activin A antibodies and ActRIIB-hFc to inhibit BMP signaling was evaluated using the W-20-17/BRE-luc cell line. For the bioassay, W-20-17/BRE-luc cells are seeded onto 96-well assay plates at 10,000 cells/well and incubated at 37° C. and 5% CO2 overnight. The next day, BMP2, BMP4, BMP6, BMP9 or BMP10 were serially diluted at 1:3 and added to cells from 100 nM to 0.002 nM (including no BMP control for dose responses). For inhibition of BMPs by anti-Activin A antibodies or ActRIIB-hFc, antibodies or ActRIIB-hFc were serially diluted at 1:3 from 1000 nM to 0.02 nM (including no antibody, control antibody, or negative control for ActRIIB-hFc (i.e., an irrelevant protein tagged with hFc, "Control Protein")) and added to cells along with 100 pM BMP2, 100 pM BMP4, 10 nM BMP6, 800 pM BMP9 or 4 nM BMP10, as indicated. Luciferase activity was detected after 5.5 hrs of incubation in 37° C. and 5% CO2 with Victor X (Perkin Elmer) and the results were analyzed using nonlinear regression (4-parameter logistics) with Prism 5 software (GraphPad).

As shown in Table 27 below, H4H10446P2 and H4H10430P did not inhibit of any of the BMPs tested, whereas the other Activin A antibodies tested (H4H10429 and H4H10436P2) and ActRIIB-hFc all showed some inhibition of some of the BMPs. H4H10429P showed inhibition of BMP9 and BMP10 with $IC_{50}$ values of 8.1 nM and 3.5 nM, respectively, but did not inhibit BMP2, BMP4 and BMP6. H4H10436P2 showed weak inhibition of BMP2 and BMP4 at highest concentrations of the antibody and inhibition of BMP10 with an $IC_{50}$ value of >100 nM, but did not show any inhibition of BMP6 and BMP9. ActRIIB-hFc showed inhibition of BMP9 and BMP10 with $IC_{50}$ values of 2 nM and 1 nM but did not inhibit BMP2, BMP4, and BMP6. Neither of the control molecules (i.e., an isotype control antibody (Control mAb) and irrelevant protein tagged with hFc (Control Protein)), were seen to inhibit any of the BMPs, whereas BMP2, BMP4, BMP6, BMP9, or BMP10 alone (i.e., without antibodies or hFc-tagged proteins) activated the W-20-17/BRE-luc cells with $EC_{50}$ values of 34 pM, 63 pM, 4.5 nM, 260 pM, and 2.5 nM, respectively.

TABLE 27

Inhibition by anti-Activin A antibodies and ActRIIb-hFc of BMPs in W-20-17/BRE-luc cells

| Ligands | BMP2 | BMP4 | BMP6 | BMP9 | BMP10 |
|---|---|---|---|---|---|
| EC50 [M] | 3.4E−11 | 6.3E−11 | 4.5E−09 | 2.6E−10 | 2.5E−09 |
| Constant BMP | 100 pM | 100 pM | 10 nM | 800 pM | 4 nM |
| Antibodies | IC50 [M] | IC50 [M] | IC50 [M] | IC50 [M] | IC50 [M] |
| H4H10446P2 | No Inhibition | No Inhibition | No Inhibition | No Inhibition | No Inhibition |
| H4H10430P | No Inhibition | No Inhibition | No Inhibition | No Inhibition | No Inhibition |
| H4H10429P | No Inhibition | No Inhibition | No Inhibition | 8.1E−09 | 3.5E−09 |
| H4H10436P2 | Weak (31% inhibition at 1 uM) | Weak (51% inhibition at 1 uM) | No Inhibition | No Inhibition | >1.0E−07 |
| ActRIIB-hFc | No Inhibition | No Inhibition | No Inhibition | 2.0E−09 | 1.0E−09 |
| Control mAb | No Inhibition | No Inhibition | No Inhibition | No Inhibition | No Inhibition |
| Control Protein | No Inhibition | No Inhibition | No Inhibition | No Inhibition | No Inhibition |

Example 13

Treatment with Anti-Activin a Antibody H4H10446P2 Reduces Renal Fibrosis in Vivo The effect of a specific anti-activin A antibody of the invention, H4H10446P2, on renal fibrosis was determined in an unilateral ureteral obstruction (UUO) mouse model of renal fibrosis. The UUO model was developed by complete ligation of the left ureter while keeping the right kidney function intact. Briefly, UUO was performed in mice under Ketamine/Xylazine anesthesia, whereby the left ureter was accessed via flank incision, and two ligatures were placed on the proximal one-third of the ureter using 5-0 silk thread at 5 mm apart. Sham surgeries were done in a similar fashion without placing any ligatures on the ureter. In this model, severe fibrosis develops in the kidney within 14 days following UUO, which has been assessed by measuring kidney collagen by directly measuring the amount of hydroxyproline in the sample, which is referred to as the hydroxyproline method. Hydroxyproline is a specific component of collagens, and represents approximately 14.4% of the amino acid composition of collagen in most mammalian tissues (Cochrane et al., J Am Soc Nephrol 16:3623-30 (2005)). To measure collagen content via the hydroxyproline method, first frozen kidney samples were dried overnight using a vacuum chamber. Dried kidney tissue samples were then homogenized in an ice-cold NaCl/NaHCO$_3$ solution and were then hydrolyzed using 6 M HCl. The samples were subsequently dried using a vacuum centrifuge, and then were rehydrated using 0.1 M HCl. The hydroxyproline in the rehydrated samples was oxidized with 300 mM Chloramine T (Sigma, #857319) and Ehrlich's reagent [3.5M p-dimethylaminobenzaldehyde (FW: 149.19, Sigma, #39070) in 60% perchloric acid (Sigma, #311413)] was then added to develop the color. Finally, using a spectrophotometer, absorbance of the samples was measured at 558 nm and this was compared to hydroxyproline standards (Sigma, # H5534) of known concentration, to determine the kidney hydroxyproline content. The measured hydroxyproline value was then multiplied by a factor of 6.94 to determine the collagen value. Fourteen days following UUO, dry kidney weight decreases as a result of parenchymal damage. Sham (n=10) or UUO (n=20) surgeries were performed on 16-week old male C57BL/6 mice (Taconic farms, Inc.). Mice, which underwent UUO surgery, were then divided into two groups. Each UUO group received a subcutaneous injection of either H4H10446P2 (40 mg/kg, n=10) or an isotype control antibody (40 mg/kg, n=10), which does not bind to any known mouse protein, starting a day before the surgeries, and on 1, 3, 6, 8, 10, and 13 days after the surgery. The mice that underwent the sham surgery received vehicle (sterile PBS) during this time using the same schedule as the UUO groups. All the mice were sacrificed on day 14 following surgery. The kidney weights were measured, and the kidneys were flash-frozen using liquid nitrogen, and kept at −80° C. until the collagen content was measured. Kidney collagen content was measured using the hydroxyproline method, and then expressed as either total kidney collagen (μg) or kidney collagen normalized to kidney weight (μg/mg of dry weight). Statistical analysis was done using One-Way ANOVA with Turkey's multiple comparison test. The results including summarizes total kidney collagen, normalized kidney collagen, and dry kidney weights for each treatment group were expressed as mean±SEM in Table 28 below.

Example 14

Figure 4:
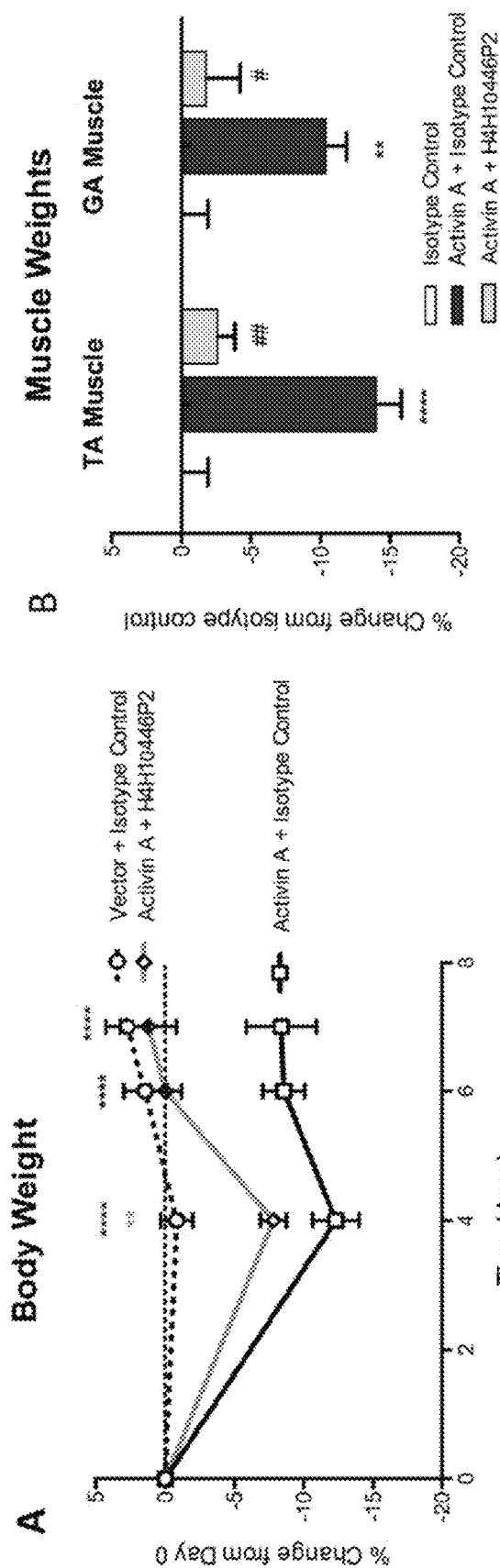
FIG. 4: Panel A shows the effects of the administration of the anti-Activin A antibody H4H10446P2 on body weight of mice overexpressing Activin A (versus isotype control). Data was analyzed using two-way analysis of variance (Repeated Measures ANOVA+Boneferroni Multiple Comparison Test) followed by Tukey's test. *=p<0.05 vs Isotype Control; #=p<0.05 vs Activin A+Isotype Control. Panel B shows the effects of anti-Activin A antibody H4H10446P2 on tibialis anterior (TA) and Gastrocnemius (GA) muscle weights in mice overexpressing Activin A (versus isotype control). Data analyzed using one-way analysis of variance (ANOVA) followed by Tukey's test. *=p<0.05 over Vector+Isotype Control; #=p<0.05 over Activin A+Isotype Control.

Effects of H4H10446P2 on Body Weight and Muscle Mass in Mice Overexpressing Activin A To assess the efficacy of H4H10446P2 in neutralizing elevated levels of Activin A in mice, Activin A was overexpressed in C57BL/6 mice (10 weeks-old) by hydrodynamic delivery (HDD) of a DNA construct encoding full-length Activin A. Mice were randomized into three groups (n=5-6/group); one was injected with a mixture of saline/2.5 μg of a DNA construct control in presence of an isotype control antibody, and two groups were injected with a mixture of saline/2.5 μg of a DNA construct containing Activin A in presence of an isotype control antibody or H4H10446P2. DNA constructs were injected on day 0, and antibodies were administered on days 0 and 4 at 2.5 mg/kg (2 injections) for 7 days. Muscle weights were reported as normalized weights (i.e., muscle weights were normalized to the body weights measured at the start of the experiment). Results for body weights are shown as average change from starting body weights. Results for tibialis anterior (TA) and gastrocnemius (GA) muscles are shown in FIG. 4 as average percent change for each group (±standard error of the mean) compared to the HDD delivery of a construct control+ isotype control antibody group. The data were analyzed with one or two-way ANOVA followed by Tukey HSD test.

As seen in FIG. 4, seven days after HDD, delivery of Activin A in mice treated with an isotype control antibody

TABLE 28

Total Kidney collagen, Normalized Kidney Collagen, and Dry Kidney Weight in each group (mean ± SEM)

| Treatment Group | Total Kidney Collagen (μg) | Normalized Kidney Collagen (μg/mg of tissue dry weight) | Dry Kidney Weight (g) |
| --- | --- | --- | --- |
| Sham + Vehicle | 429.6 ± 25.93 | 8.16 ± 0.29 | 0.0524 ± 0.002 |
| UUO + Isotype Control | 980.7 ± 50.48 | 25.07 ± 0.86 | 0.0396 ± 0.0027 |
| UUO + H4H10446P2 | 730.7 ± 48.02 | 17.48 ± 0.79 | 0.0422 ± 0.0029 |

As shown in Table 28, both total kidney collagen and kidney collagen normalized to kidney weight was significantly increased in UUO mice compared to sham-operated mice. UUO mice treated with H4H10446P2 exhibited significant reduction in both total kidney collagen and kidney collagen normalized to kidney weight (approximately 45% reduction in fibrotic collagen) compared to isotype control antibody treated UUO mice, indicating the anti-activin A antibody lead to decreased fibrosis in the kidney. UUO mice treated with H4H10446P2 exhibited an increase in dry kidney weight compared to the isotype control antibody treated UUO mice, indicating preservation of parenchyma in the anti-activin A antibody treated mice.

resulted in significant decreases in body weights (−10.81±2.46%) and the mass of tibialis and gastrocnemius muscles (of −13.96±1.85% and of −10.34±1.51%, respectively) ($p<0.01$ significance over isotype control). Delivery of Activin A in mice treated with H4H10446P2 resulted in a significant attenuation of body weights (−1.49±1.98%) and the mass of tibialis and gastrocnemius muscles at the end of seven days of treatment (of −2.57±1.26% and of −1.77±2.42%, respectively).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. An isolated antibody or antigen-binding fragment thereof that specifically binds Activin A with a binding dissociation equilibrium constant ($K_D$) of less than about 5 pM as measured in a surface plasmon resonance assay at 25° C., wherein the antibody or antigen-binding fragment comprises: (a) the complementarity determining regions (CDRs) of a HCVR having the amino acid sequence of SEQ ID NO: 162; and (b) the CDRs of a LCVR having the amino acid sequence of SEQ ID NO: 146.

2. The isolated antibody or antigen-binding fragment thereof of claim 1, wherein the isolated antibody or antigen-binding fragment thereof specifically binds Activin A with a $K_D$ of less than about 4 pM as measured in a surface plasmon resonance assay at 25° C.

3. The isolated antibody or antigen-binding fragment thereof of claim 1 or 2, wherein the antibody or antigen-binding fragment thereof blocks binding of at least one Activin A receptor to Activin A.

4. The isolated antibody or antigen-binding fragment thereof of claim 3, wherein the antibody or antigen-binding fragment thereof blocks Activin A binding to an Activin A receptor with an $IC_{50}$ value of less than about 80 pM as measured in an in vivo receptor/ligand binding bioassay at 25° C.

5. The isolated antibody or antigen-binding fragment thereof of claim 4, wherein the antibody or antigen-binding fragment thereof blocks Activin A binding to an Activin A receptor with an $IC_{50}$ value of less than about 60 pM as measured in an in vivo receptor/ligand binding bioassay at 25° C.

6. The isolated antibody or antigen-binding fragment thereof of claim 1 or 2, wherein the antibody or antigen-binding fragment thereof blocks activation of at least one Activin A receptor by Activin A, wherein the Activin A receptor is selected from the group consisting of Activin Type IIA receptor (ActRIIA), Activin Type IIB receptor (ActRIIB), and Activin Type I receptor.

7. The isolated antibody or antigen-binding fragment thereof of claim 6, wherein the antibody or antigen-binding fragment thereof does not significantly block binding of Activin A to an Activin Type II receptor.

8. The isolated antibody or antigen-binding fragment thereof of claim 1, wherein the isolated antibody or antigen-binding fragment thereof specifically binds Activin A with a binding association equilibrium constant ($K_a$) of less than about 500 nM.

9. The isolated antibody or antigen-binding fragment thereof of claim 1, wherein the antibody or antigen-binding fragment thereof inhibits binding of Activin A to an Activin A receptor selected from the group consisting of Activin Type IIA receptor (ActRIIA), Activin Type IIB receptor (ActRIIB), and Activin Type I receptor.

10. The isolated antibody or antigen-binding fragment thereof of claim 1, wherein the antibody or antigen-binding fragment thereof inhibits Activin A-mediated activation of SMAD complex signaling.

11. The isolated antibody or antigen-binding fragment thereof of claim 1, wherein the antibody or antigen-binding fragment thereof competes for binding to Activin A with a reference antibody comprising a heavy chain variable region (HCVR)/light chain variable region (LCVR) sequence pair selected from the group consisting of SEQ ID NOs: 2/10, 138/146, 162/146, and 194/146.

12. A pharmaceutical composition comprising the antibody or antigen-binding fragment of claim 1, and a pharmaceutically acceptable carrier or diluent.

13. A pharmaceutical composition comprising the antibody or antigen-binding fragment of claim 1, a GDF8 antagonist, and a pharmaceutically acceptable carrier or diluent.

14. The pharmaceutical composition of claim 13, wherein GDF8 antagonist is selected from the group consisting of a GDF8-inhibiting fusion protein, an anti-GDF8 antibody, and an antigen-binding fragment of an anti-GDF8 antibody.

15. The pharmaceutical composition of claim 14, wherein the anti-GDF8 antibody, or antigen-binding fragment of an anti-GDF8 antibody, comprises the heavy chain complementarity determining regions (HCDRs) of a HCVR comprising SEQ ID NO:217, and the light chain complementarity determining regions (LCDRs) of a LCVR comprising SEQ ID NO:221.

16. A method for increasing muscle mass or strength in a subject, the method comprising administering to the subject the pharmaceutical composition of claim 13.

17. The pharmaceutical composition of claim 14, wherein the GDF8 antagonist is an anti-GDF8 antibody or antigen-binding fragment thereof comprising:
a) three HCDRs comprising SEQ ID NO:218, SEQ ID NO:219, and SEQ ID NO:220, and
b) three LCDRs comprising SEQ ID NO:222, SEQ ID NO:223, and SEQ ID NO:224.

18. A method for increasing muscle mass or strength in a subject, the method comprising administering to the subject the pharmaceutical composition of claim 12.

19. The method of claim 18, further comprising the administration of a GDF8 antagonist, wherein the GDF8 antagonist is an anti-GDF8 antibody or antigen-binding fragment thereof.

20. The method of claim 19, wherein the GDF8 antagonist is an anti-GDF8 antibody or antigen-binding fragment thereof comprising the heavy chain complementarity determining regions (HCDRs) of a HCVR comprising SEQ ID NO:217, and the light chain complementarity determining regions (LCDRs) of a LCVR comprising SEQ ID NO:221.

21. The method of claim 19, wherein the GDF8 antagonist is an anti-GDF8 antibody or antigen-binding fragment thereof comprising:
a) three HCDRs comprising SEQ ID NO:218, SEQ ID NO:219, and SEQ ID NO:220, and
b) three LCDRs comprising SEQ ID NO:222, SEQ ID NO:223, and SEQ ID NO:224.

22. An isolated antibody or antigen-binding fragment thereof that specifically binds Activin A, wherein the antibody or antigen-binding fragment comprises: (a) the complementarity determining regions (CDRs) of a HCVR having the amino acid sequence of SEQ ID NO: 162; and (b) the CDRs of a LCVR having the amino acid sequence of SEQ ID NO: 146.

23. The isolated antibody or antigen-binding fragment thereof of claim 22, wherein the antibody or antigen-binding fragment comprises the heavy and light chain CDRs of a HCVR/LCVR amino acid sequence pair of: SEQ ID NOs: 162/146.

24. The isolated antibody or antigen-binding fragment thereof of claim 23, wherein the antibody or antigen-binding fragment thereof comprises HCDR1-HCDR2-HCDR3-LCDR1-LCDR2-LCDR3 domains, respectively, of: SEQ ID NOs: 164-166-168-148-150-152.

25. An isolated antibody or antigen-binding fragment thereof that specifically binds Activin A, wherein the antibody or antigen-binding fragment comprises: (a) a HCVR having the amino acid sequence of SEQ ID NO: 162; and (b) a LCVR having the amino acid sequence of SEQ ID NO: 146.

26. A method for increasing muscle mass or strength in a subject, the method comprising administering to the subject an antigen-binding molecule comprising an Activin A-specific binding domain and a GDF8-specific binding domain, wherein the Activin A-specific binding domain comprises: (a) the complementarity determining regions (CDRs) of a HCVR having the amino acid sequence of SEQ ID NO: 162; and (b) the CDRs of a LCVR having the amino acid sequence of SEQ ID NO: 146.

27. The method of claim 26, wherein the Activin A-specific binding domain comprises a HCVR and a LCVR.

28. The method of claim 27, wherein the HCVR comprises:
(a) the CDRs of a HCVR having the amino acid sequence of SEQ ID NO: 162; and
(b) the CDRs of a LCVR having the amino acid sequence of SEQ ID NO: 146.

29. The method of claim 26, wherein the GDF8-specific binding domain comprises a HCVR and a LCVR.

30. The method of claim 29, wherein the HCVR comprises three heavy chain complementarity determining regions (HCDRs) comprising SEQ ID NO:218, SEQ ID NO:219, and SEQ ID NO:220, and wherein the LCVR comprises three light chain complementarity determining regions (LCDRs) comprising SEQ ID NO:222, SEQ ID NO:223, and SEQ ID NO:224.

31. The method of claim 26, wherein the Activin A-specific binding domain comprises a heavy chain variable region (HCVR) and a light chain variable region (LCVR), and wherein the GDF8-specific binding domain comprises a heavy chain variable region (HCVR) and a light chain variable region (LCVR).

32. The method of claim 26, wherein the antigen-binding molecule is a bispecific antibody.

33. A method for increasing muscle mass or strength in a subject with a disease or disorder characterized by decreased muscle mass or strength, the method comprising administering to a subject in need thereof an Activin A-specific binding protein, wherein the Activin A-specific binding protein comprises: (a) the complementarity determining regions (CDRs) of a HCVR having the amino acid sequence of SEQ ID NO: 162; and (b) the CDRs of a LCVR having the amino acid sequence of SEQ ID NO: 146.

34. A method for increasing muscle mass or strength in a subject with a disease or disorder characterized by decreased muscle mass or strength, the method comprising administering to a subject in need thereof an Activin A-specific binding protein and a GDF8-specific binding protein, wherein the Activin A-specific binding domain comprises: (a) the complementarity determining regions (CDRs) of a HCVR having the amino acid sequence of SEQ ID NO: 162; and (b) the CDRs of a LCVR having the amino acid sequence of SEQ ID NO: 146.

35. The method of claim 34, wherein the disease or disorder characterized by decreased muscle mass or strength is selected from the group consisting of sarcopenia, cachexia, muscle injury, muscle wasting/atrophy, cancer, obesity, diabetes, arthritis, multiple sclerosis, muscular dystrophy, amyotrophic lateral sclerosis, Parkinson's disease, osteoporosis, osteoarthritis, osteopenia, and a metabolic syndrome.

36. The method of claim 35, wherein the cachexia is idiopathic or is cachexia secondary to another condition.

37. The method of claim 36, wherein the condition is cancer, chronic renal failure, or chronic obstructive pulmonary disease.

38. The method of claim 35, wherein the muscle wasting/atrophy is caused by or associated with a condition selected from the group consisting of disuse, immobilization, bed rest, injury, medical treatment, surgical intervention and mechanical ventilation.

39. The method of claim 38, wherein the surgical intervention is selected from the group consisting of hip fracture, hip replacement, and knee replacement.

40. The method of claim 35, wherein the metabolic syndrome includes a disease or disorder selected from the group consisting of diabetes, obesity, nutritional disorders, organ atrophy, chronic obstructive pulmonary disease, and anorexia.

41. A method for increasing muscle mass or strength in a subject with a disease or disorder characterized by decreased muscle mass or strength, the method comprising administering to a subject in need thereof an antigen-binding molecule comprising an Activin A-specific binding domain and a GDF8-specific binding domain, wherein the Activin A-specific binding domain comprises: (a) the complementarity determining regions (CDRs) of a HCVR having the amino acid sequence of SEQ ID NO: 162; and (b) the CDRs of a LCVR having the amino acid sequence of SEQ ID NO: 146.

42. A method for treating or ameliorating a disease or disorder that is caused by, promoted by, exacerbated by, or aggravated by Activin A activity, the method comprising administering to a subject in need thereof an Activin A antibody or antigen-binding fragment thereof, wherein the antibody or antigen-binding fragment comprises: (a) the complementarity determining regions (CDRs) of a HCVR having the amino acid sequence of SEQ ID NO: 162; and (b) the CDRs of a LCVR having the amino acid sequence of SEQ ID NO: 146.

43. The method of claim 42, wherein the disease or disorder is renal fibrosis.

44. The method of claim 42, wherein the disease or disorder is cachexia.

* * * * *